(12) United States Patent
Smith et al.

(10) Patent No.: US 10,017,750 B2
(45) Date of Patent: *Jul. 10, 2018

(54) MODIFIED POLYMERASES FOR IMPROVED INCORPORATION OF NUCLEOTIDE ANALOGUES

(71) Applicant: Illumina Cambridge Limited, Nr Saffron Walden (GB)

(72) Inventors: Geoffrey Paul Smith, Nr Saffron Walden (GB); David Mark Dunstan Bailey, Cambridge (GB); Raquel Maria Sanches-Kuiper, Nr Saffron Walden (GB); Harold Swerdlow, Cambridge (GB); David James Earnshaw, Cambridgeshire (GB)

(73) Assignee: ILLUMINA CAMBRIDGE LIMITED, Nr Saffron Walden (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/247,561

(22) Filed: Aug. 25, 2016

(65) Prior Publication Data

US 2016/0362664 A1 Dec. 15, 2016

Related U.S. Application Data

(63) Continuation of application No. 14/476,387, filed on Sep. 3, 2014, now Pat. No. 9,447,389, which is a continuation of application No. 13/856,556, filed on Apr. 4, 2013, now Pat. No. 8,852,910, which is a continuation of application No. 10/571,706, filed as application No. PCT/GB2004/003891 on Sep. 10, 2004, now Pat. No. 8,460,910.

(30) Foreign Application Priority Data

Sep. 11, 2003 (GB) .................................. 0321306.3

(51) Int. Cl.
*C12N 9/12* (2006.01)
*C12Q 1/6869* (2018.01)

(52) U.S. Cl.
CPC ......... *C12N 9/1252* (2013.01); *C12Q 1/6869* (2013.01); *C12Y 207/07007* (2013.01)

(58) Field of Classification Search
None
See application file for complete search history.

(56) References Cited

U.S. PATENT DOCUMENTS 8,268,605 B2 9/2012 Sorge et al.
2002/0132249 A1 9/2002 Patel et al.

FOREIGN PATENT DOCUMENTS

| EP | 0701000 A2 | 3/1996 |
|---|---|---|
| EP | 0701000 B1 | 1/2001 |
| WO | WO 97/39150 A1 | 10/1997 |
| WO | WO 01/23411 A2 | 4/2001 |
| WO | WO 01/32887 A1 | 5/2001 |
| WO | WO 02/101358 A2 | 12/2002 |
| WO | WO 03/54139 A2 | 7/2003 |
| WO | WO 2004/018497 A2 | 3/2004 |
| WO | WO 2004/039947 A2 | 5/2004 |

OTHER PUBLICATIONS

"Notice of Reasons for Rejection, dated Jun. 22, 2010, in Japanese Application P 2006-525 897 (JP national phase of PCT/GB04/003891, which is this application)".
Arezi et al., "Efficient and High Fidelity Incorporation of Dye-terminators by a Novel Archaeal DNA Polymerase Mutant", *J. Mol. Biol*, Sep. 2002; 322(4):719-729.
Bonnin et al., "A Single Tyrosine Prevents Insertion of Ribonucleotides in the Eukaryotic-type φ29 DNA Polymerase", *J. Mol. Biol.* Jul. 1999; 290(1):241-251.
Canard et al., "DNA polymerase fluorescent substrates with reversible 3'-tags", *Gene*, Oct. 1994; 148(1):1-6.
Dong et al., "Mutational Studies of Human DNA Polymerase alpha. Serine 867 in the second most conserved region among alpha-like DNA polymerases is involved in primer binding and mispair primer extension", *The Journal of Biological Chemistry*, Nov. 1993; 268(32):24175-24182.
Dong et al., "Mutational studies of human DNA polymerase alpha: Identification of residues critical for deoxynucleotide binding and misinsertion fidelity of DNA synthesis", *The Journal of Biological Chemistry*, Nov. 1993; 268(32):24163-24174.
Doublie et al., "Crystal structure of a bacteriophage T7 DNA replication complex at 2.2 Å resolution", *Nature*, Jan. 1998; 391:251-258.
Evans et al., "Improving dideoxynucleotide-triphosphate utilisation by the hyper-thermophilic DNA polymerase from the archaeon *Pyrococcus furiosus*", *Nucleic Acids Res.*, Mar. 2000; 28(5):1059-1066.
Franklin et al., "Structure of the Replicating Complex of a Pol α Family DNA Polymerase", *Cell*, Jun. 2001; 105(5):657-667.
Froud, "Notice of Opposition to a European patent", EP Patent No. 2325304B1' dated Feb. 7, 2013, 4.
Froud, "Opposition Brief", dated Feb. 11, 2013, 10.
Gardner et al., "Acrylic and dideoxy terminator preferences denote divergent sugar recognition by archaeon and Taq DNA polymerases", *Nucleic Acids Res.*, Jan. 2002; 30(2):605-613.
Gardner et al., "Determinants of nucleotide sugar recognition in an archaeon DNA polymerase", *Nucleic Acids Res.*, Jun. 1999; 27(12):2545-2553.
Hopfner et al., "Crystal structure of a thermostable type B DNA polymerase from *Thermococcus gorgonarius*", Mar. 1999, *Proc. Natl. Acad. Sci. USA*; 96:3600-3605.

(Continued)

*Primary Examiner* — Richard G Hutson
(74) *Attorney, Agent, or Firm* — Mueting, Raasch & Gebhardt, P.A.

(57) ABSTRACT

The invention relates to modified polymerase enzymes which exhibit improved incorporation of nucleotide analogs bearing substituents at the 3' position of the sugar moiety that are larger in size than the naturally occurring 3' hydroxyl group. Also described are methods of using the polymerases to incorporate nucleotides into polynucleotides, particularly in the context of DNA sequencing.

21 Claims, 2 Drawing Sheets

(56) References Cited

OTHER PUBLICATIONS

Joyce et al., "Function and Structure Relationships in DNA Polymerases", *Annu. Rev. Biochem.*, 1994; 63:777-822.

Kilger, Opposition Brief, dated Feb. 6, 2013, 33.

Kilger, "Notice of Opposition to a European patent", EP Patent No. EP2325304, dated Feb. 6, 2013, 7.

Liu et al., "Identification of Conserved Residues Contributing to the Activities of Adenovirus DNA Polymerase", *J. Virol.*, Dec. 2000; 74(24):11681-11689.

Lutz et al., "Recognition of a Non-standard Base Pair by thermostable DNA Polymerases", *Bioorganic & Medicinal Chemistry Letters*, Jun. 1998; 8(10):1149-1152.

Metzker et al., "Termination of DNA synthesis by novel 3'-modified-deoxyribonucleoside 5'-triphosphases", *Nucleic Acids Res.*, Oct. 1994; 22(20): 4259-4267.

Morrison et al., "Combinatorial alanine-scanning", *Current Opinion in Chemical Biology*, 2001, 5:302-307.

Ngo et al., "The Protein Folding Problem and Tertiary Structure Prediction", 1994, Merz et al (ed.), Birkhauser, Boston, MA, 433 and 492-495.

Pavlov et al., "In Vivo consequences of putative active site mutations in yeast DNA polymerase alpha, epsilon, delta, and zeta", *Genetics*, Sep. 2001; 159(1):47-64.

Rodriguez et al., "Crystal structure of a pol alpha family DNA polymerase from the hyperthermophilic archaeon *Thermococcus* sp. 9°N-7", *Journal of Molecular Biology*, Jun. 2000; 299 (2): 447-462.

Southworth et al., "Cloning of thermostable DNA polymerases from hyperthermophilic marine Archaea with emphasis on *Thermococcus* sp. 9 degrees N-7 and mutations affecting 3'-5' Exonuclease activity", *Proc. Natl. Acad. Sci. USA.*, May 1996; 93(11):5281-5285.

St. Clair et al., "3'-Azido-3"-Deoxythymidine Triphosphate as an Inhibitor and Substrate of Purified Human Immunodeficiency Virus Reverse Transcriptase", *Antimicrob. Agents Chemother.*, Dec. 1987; 31(12): 1972-1977.

Stachelhaus et al., "The specificity-conferring code of adenylation domains in nonribosomal peptide synthetases", *Chem. Biol.*, Aug. 1999; 6(8):493-505.

Steitz, "DNA Polymerases: Structural Diversity and Common Mechanisms", *J. Biol. Chem.*, Jun. 1999; 274(25):17395-17398.

Suzuki et al., "Random mutagenesis of Thermus aquaticus DNA polymerase I: Concordance of immutable sites in vivo with the crystal structure", *Proc. Natl. Acad. Sci.*, Sep. 1996; 93(18):9670-9675.

Tomic-Canic et al., "A Simple Method for Site-Specific Mutagenesis that Leaves the Rest of the Template Unaltered", *Methods Mol. Biol.*, 1996; 57:259-267.

Tunitskaya et al., "Structural-functional Analysis of Bacteriophage T7 RNA Polymerase", *Biochemistry (Mosc.)*, Oct. 2002; 67(10):1124-1135.

Welch et al., "Syntheses of Nucleosides Designed for Combinatorial DNA Sequencing", *Chemistry, European Journal*, Mar. 1999; 5 (3): 951-960.

Yang et al., "A conserved Tyr residue is required for sugar selectivity in a Pol alpha DNA polymerase", *Biochemistry*, Aug. 2002; 41(32):10256-10261.

SEQUENCE LISTING

```
<160> NUMBER OF SEQ ID NOS: 36

<210> SEQ ID NO 1
<211> LENGTH: 25
<212> TYPE: DNA
<213> ORGANISM: Artificial sequence
<220> FEATURE:
```

<223> OTHER INFORMATION: Oligonucleotide primer

<400> SEQUENCE: 1
cactcatgat tagatctcgt gcagc					25

<210> SEQ ID NO 2
<211> LENGTH: 58
<212> TYPE: DNA
<213> ORGANISM: Artificial sequence
<220> FEATURE:
<223> OTHER INFORMATION: Oligonucleotide primer

<400> SEQUENCE: 2
cactcatgat tagatctcgt gcagcccatg gtgattctcg ataccgacta catcaccg					58

<210> SEQ ID NO 3
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 3
cgagcggaag tctaaataca caat					24

<210> SEQ ID NO 4
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 4
attgtgtatt tagacttccg ctcg					24

<210> SEQ ID NO 5
<211> LENGTH: 54
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (25)..(26)
<223> OTHER INFORMATION: n is a, c, g or t
<220> FEATURE:
<221> NAME/KEY: misc_feature
<222> LOCATION: (27)..(27)
<223> OTHER INFORMATION: k is g or t/u
<220> FEATURE:
<221> NAME/KEY: misc_feature
<222> LOCATION: (28)..(29)
<223> OTHER INFORMATION: n is a, c, g or t
<220> FEATURE:
<221> NAME/KEY: misc_feature
<222> LOCATION: (30)..(30)
<223> OTHER INFORMATION: k is g or t/u
<220> FEATURE:
<221> NAME/KEY: misc_feature
<222> LOCATION: (31)..(32)
<223> OTHER INFORMATION: n is a, c, g or t
<220> FEATURE:
<221> NAME/KEY: misc_feature
<222> LOCATION: (33)..(33)
<223> OTHER INFORMATION: k is g or t/u

<400> SEQUENCE: 5
attgtgtatt tagacttccg ctcgnnknnk nnktcgatca tcataaccca caac					54

```
<210> SEQ ID NO 6
<211> LENGTH: 55
<212> TYPE: DNA
<213> ORGANISM: Artificial sequence
<220> FEATURE:
<223> OTHER INFORMATION: Oligonucleotide sequence
<220> FEATURE:
<221> NAME/KEY: misc_feature
<222> LOCATION: (25)..(25)
<223> OTHER INFORMATION: m is a or c
<220> FEATURE:
<221> NAME/KEY: misc_feature
<222> LOCATION: (26)..(27)
<223> OTHER INFORMATION: n is a, c, g or t
<220> FEATURE:
<221> NAME/KEY: misc_feature
<222> LOCATION: (28)..(28)
<223> OTHER INFORMATION: m is a or c
<220> FEATURE:
<221> NAME/KEY: misc_feature
<222> LOCATION: (29)..(30)
<223> OTHER INFORMATION: n is a, c, g or t
<220> FEATURE:
<221> NAME/KEY: misc_feature
<222> LOCATION: (31)..(31)
<223> OTHER INFORMATION: m is a or c
<220> FEATURE:
<221> NAME/KEY: misc_feature
<222> LOCATION: (32)..(33)
<223> OTHER INFORMATION: n is a, c, g or t

<400> SEQUENCE: 6
gtagaagctg ttggcgagga tcttmnnmnn mnnctgcctg taatcgagga gtttc       55

<210> SEQ ID NO 7
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 7
gtagaagctg ttggcgagga tctt                                         24

<210> SEQ ID NO 8
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 8
aagatcctcg ccaacagctt ctac                                         24

<210> SEQ ID NO 9
<211> LENGTH: 63
<212> TYPE: DNA
<213> ORGANISM: Artificial sequence
<220> FEATURE:
<223> OTHER INFORMATION: Oligonucleotide primer

<400> SEQUENCE: 9
gtcgtagtcg gatgctaact accaggatcc tcaatgcttc ttccccttca ccttcagcca  60
cgc                                                                63

<210> SEQ ID NO 10
<211> LENGTH: 26
<212> TYPE: DNA
<213> ORGANISM: Artificial sequence
<220> FEATURE:
```

<210> SEQ ID NO 11
<211> LENGTH: 2328
<212> TYPE: DNA
<213> ORGANISM: Artificial sequence
<220> FEATURE:
<223> OTHER INFORMATION: 9oN polymerase variant (exo-) with L408V/Y409A/P410L R484I/A485S/I486N mutations
<220> FEATURE:
<221> NAME/KEY: CDS
<222> LOCATION: (1)..(2328)
<223> OTHER INFORMATION: coding sequence

<400> SEQUENCE: 11

```
atg att ctc gat acc gac tac atc acc gag aac ggg aag ccc gtg ata      48
Met Ile Leu Asp Thr Asp Tyr Ile Thr Glu Asn Gly Lys Pro Val Ile
1               5                   10                  15 agg gtc ttc aag aag gag aac ggc gag ttt aaa atc gag tac gac aga      96
Arg Val Phe Lys Lys Glu Asn Gly Glu Phe Lys Ile Glu Tyr Asp Arg
                20                  25                  30 acc ttc gag ccc tac ttc tac gcc ctt ctg aag gac gat tct gcg ata     144
Thr Phe Glu Pro Tyr Phe Tyr Ala Leu Leu Lys Asp Asp Ser Ala Ile
            35                  40                  45 gag gac gtc aag aag gta acc gca aag agg cac gga acg gtt gtc aag     192
Glu Asp Val Lys Lys Val Thr Ala Lys Arg His Gly Thr Val Val Lys
        50                  55                  60 gtg aag cgc gcc gag aag gtg cag aag aag ttc ctc ggc agg ccg ata     240
Val Lys Arg Ala Glu Lys Val Gln Lys Lys Phe Leu Gly Arg Pro Ile
65                  70                  75                  80 gag gtc tgg aag ctc tac ttc aac cat cct cag gac gtc ccg gcg att     288
Glu Val Trp Lys Leu Tyr Phe Asn His Pro Gln Asp Val Pro Ala Ile
                85                  90                  95 cga gac agg ata cgc gcc cac ccc gct gtc gtt gac atc tac gag tac     336
Arg Asp Arg Ile Arg Ala His Pro Ala Val Val Asp Ile Tyr Glu Tyr
                100                 105                 110 gac ata ccc ttc gcc aag cgc tac ctc atc gac aag ggc ctg att ccg     384
Asp Ile Pro Phe Ala Lys Arg Tyr Leu Ile Asp Lys Gly Leu Ile Pro
            115                 120                 125 atg gag ggc gac gag gag ctt acg atg ctc gcc ttc gcg atc gca acc     432
Met Glu Gly Asp Glu Glu Leu Thr Met Leu Ala Phe Ala Ile Ala Thr
        130                 135                 140 ctc tat cac gag ggc gag gag ttc gga acc ggg ccg att ctc atg ata     480
Leu Tyr His Glu Gly Glu Glu Phe Gly Thr Gly Pro Ile Leu Met Ile
145                 150                 155                 160 agc tac gcc gac ggg agc gag gcg agg gtg ata acc tgg aag aag att     528
Ser Tyr Ala Asp Gly Ser Glu Ala Arg Val Ile Thr Trp Lys Lys Ile
                165                 170                 175 gac ctt ccg tac gtt gac gtc gtc tcg acc gag aag gag atg att aag     576
Asp Leu Pro Tyr Val Asp Val Val Ser Thr Glu Lys Glu Met Ile Lys
                180                 185                 190 cgc ttc ctc cgc gtc gtc agg gag aag gac ccc gac gtg ctc atc acc     624
Arg Phe Leu Arg Val Val Arg Glu Lys Asp Pro Asp Val Leu Ile Thr
            195                 200                 205 tac aac ggc gac aac ttc gac ttc gcc tac ctg aag aag cgc tgt gag     672
Tyr Asn Gly Asp Asn Phe Asp Phe Ala Tyr Leu Lys Lys Arg Cys Glu
        210                 215                 220 gaa ctc gga ata aag ttc aca ctc ggc agg gac ggg agc gag ccg aag     720
Glu Leu Gly Ile Lys Phe Thr Leu Gly Arg Asp Gly Ser Glu Pro Lys
```

-continued

|  | 225 |  |  |  | 230 |  |  |  | 235 |  |  |  | 240 |  |  |  |
| --- | --- | --- | --- | --- | --- | --- | --- | --- | --- | --- | --- | --- | --- | --- | --- | --- |
| ata | cag | cga | atg | ggc | gac | cgc | ttt | gcc | gtt | gag | gtg | aag | ggc | agg | att | 768 |
| Ile | Gln | Arg | Met | Gly | Asp | Arg | Phe | Ala | Val | Glu | Val | Lys | Gly | Arg | Ile |  |
|  |  |  |  | 245 |  |  |  |  | 250 |  |  |  |  | 255 |  |  |
| cac | ttc | gac | ctc | tac | ccc | gtc | ata | agg | cgc | acg | ata | aac | ctc | ccg | acc | 816 |
| His | Phe | Asp | Leu | Tyr | Pro | Val | Ile | Arg | Arg | Thr | Ile | Asn | Leu | Pro | Thr |  |
|  |  |  | 260 |  |  |  |  | 265 |  |  |  |  | 270 |  |  |  |
| tac | acc | ctt | gag | gcc | gtt | tac | gag | gcc | gtc | ttt | gga | aag | ccc | aag | gag | 864 |
| Tyr | Thr | Leu | Glu | Ala | Val | Tyr | Glu | Ala | Val | Phe | Gly | Lys | Pro | Lys | Glu |  |
|  |  | 275 |  |  |  |  | 280 |  |  |  |  | 285 |  |  |  |  |
| aag | gtt | tac | gca | gag | gag | ata | gcg | cag | gcc | tgg | gag | agc | ggg | gag | ggc | 912 |
| Lys | Val | Tyr | Ala | Glu | Glu | Ile | Ala | Gln | Ala | Trp | Glu | Ser | Gly | Glu | Gly |  |
|  | 290 |  |  |  |  | 295 |  |  |  |  | 300 |  |  |  |  |  |
| ctt | gaa | agg | gtt | gca | aga | tac | tcg | atg | gag | gac | gct | aag | gtg | acc | tac | 960 |
| Leu | Glu | Arg | Val | Ala | Arg | Tyr | Ser | Met | Glu | Asp | Ala | Lys | Val | Thr | Tyr |  |
| 305 |  |  |  |  | 310 |  |  |  |  | 315 |  |  |  |  | 320 |  |
| gag | ctg | gga | agg | gag | ttc | ttc | ccg | atg | gag | gcc | cag | ctt | tcg | agg | ctt | 1008 |
| Glu | Leu | Gly | Arg | Glu | Phe | Phe | Pro | Met | Glu | Ala | Gln | Leu | Ser | Arg | Leu |  |
|  |  |  |  | 325 |  |  |  |  | 330 |  |  |  |  | 335 |  |  |
| ata | ggc | cag | agc | ctc | tgg | gac | gtc | tcg | cgc | tcg | agc | acc | gga | aat | ttg | 1056 |
| Ile | Gly | Gln | Ser | Leu | Trp | Asp | Val | Ser | Arg | Ser | Ser | Thr | Gly | Asn | Leu |  |
|  |  |  | 340 |  |  |  |  | 345 |  |  |  |  | 350 |  |  |  |
| gtg | gag | tgg | ttc | ctc | ctg | cgg | aag | gcc | tac | aag | agg | aac | gag | ctc | gcc | 1104 |
| Val | Glu | Trp | Phe | Leu | Leu | Arg | Lys | Ala | Tyr | Lys | Arg | Asn | Glu | Leu | Ala |  |
|  |  | 355 |  |  |  |  | 360 |  |  |  |  | 365 |  |  |  |  |
| cca | aac | aag | ccc | gac | gag | agg | gag | ctc | gcg | aga | cgg | cgc | ggg | ggc | tac | 1152 |
| Pro | Asn | Lys | Pro | Asp | Glu | Arg | Glu | Leu | Ala | Arg | Arg | Arg | Gly | Gly | Tyr |  |
|  | 370 |  |  |  |  | 375 |  |  |  |  | 380 |  |  |  |  |  |
| gct | ggc | ggg | tac | gtt | aag | gaa | cca | gag | cgg | gga | ttg | tgg | gac | aac | att | 1200 |
| Ala | Gly | Gly | Tyr | Val | Lys | Glu | Pro | Glu | Arg | Gly | Leu | Trp | Asp | Asn | Ile |  |
| 385 |  |  |  |  | 390 |  |  |  |  | 395 |  |  |  |  | 400 |  |
| gtg | tat | tta | gac | ttc | cgc | tcg | gtt | gcg | ttg | tcg | atc | atc | ata | acc | cac | 1248 |
| Val | Tyr | Leu | Asp | Phe | Arg | Ser | Val | Ala | Leu | Ser | Ile | Ile | Ile | Thr | His |  |
|  |  |  |  | 405 |  |  |  |  | 410 |  |  |  |  | 415 |  |  |
| aac | gtc | tcg | ccg | gat | acc | ctc | aac | cgc | gag | ggc | tgt | aaa | gag | tac | gac | 1296 |
| Asn | Val | Ser | Pro | Asp | Thr | Leu | Asn | Arg | Glu | Gly | Cys | Lys | Glu | Tyr | Asp |  |
|  |  |  | 420 |  |  |  |  | 425 |  |  |  |  | 430 |  |  |  |
| gtc | gcc | cct | gag | gtt | gga | cac | aag | ttc | tgc | aag | gac | ttc | ccc | ggc | ttc | 1344 |
| Val | Ala | Pro | Glu | Val | Gly | His | Lys | Phe | Cys | Lys | Asp | Phe | Pro | Gly | Phe |  |
|  |  | 435 |  |  |  |  | 440 |  |  |  |  | 445 |  |  |  |  |
| ata | cca | agc | ctc | ctg | gga | gat | ttg | ctc | gag | gag | agg | cag | aag | ata | aag | 1392 |
| Ile | Pro | Ser | Leu | Leu | Gly | Asp | Leu | Leu | Glu | Glu | Arg | Gln | Lys | Ile | Lys |  |
|  | 450 |  |  |  |  | 455 |  |  |  |  | 460 |  |  |  |  |  |
| cgg | aag | atg | aag | gca | acg | gtt | gac | ccg | ctg | gag | aag | aaa | ctc | ctc | gat | 1440 |
| Arg | Lys | Met | Lys | Ala | Thr | Val | Asp | Pro | Leu | Glu | Lys | Lys | Leu | Leu | Asp |  |
| 465 |  |  |  |  | 470 |  |  |  |  | 475 |  |  |  |  | 480 |  |
| tac | agg | cag | att | tcg | aat | aag | atc | ctc | gcc | aac | agc | ttc | tac | ggc | tac | 1488 |
| Tyr | Arg | Gln | Ile | Ser | Asn | Lys | Ile | Leu | Ala | Asn | Ser | Phe | Tyr | Gly | Tyr |  |
|  |  |  |  | 485 |  |  |  |  | 490 |  |  |  |  | 495 |  |  |
| tac | ggc | tac | gcc | aag | gcc | cgg | tgg | tac | tgc | aag | gag | tgc | gcc | gag | agc | 1536 |
| Tyr | Gly | Tyr | Ala | Lys | Ala | Arg | Trp | Tyr | Cys | Lys | Glu | Cys | Ala | Glu | Ser |  |
|  |  |  | 500 |  |  |  |  | 505 |  |  |  |  | 510 |  |  |  |
| gtt | acg | gcc | tgg | gga | agg | gag | tat | ata | gaa | atg | gtt | atc | cgg | gaa | ctc | 1584 |
| Val | Thr | Ala | Trp | Gly | Arg | Glu | Tyr | Ile | Glu | Met | Val | Ile | Arg | Glu | Leu |  |
|  |  | 515 |  |  |  |  | 520 |  |  |  |  | 525 |  |  |  |  |
| gaa | gaa | aaa | ttc | ggt | ttt | aaa | gtt | ctc | tat | gcc | gat | aca | gac | ggt | ctc | 1632 |
| Glu | Glu | Lys | Phe | Gly | Phe | Lys | Val | Leu | Tyr | Ala | Asp | Thr | Asp | Gly | Leu |  |
|  | 530 |  |  |  |  | 535 |  |  |  |  | 540 |  |  |  |  |  |
| cat | gct | acc | att | ccc | gga | gca | gac | gct | gaa | aca | gtc | aag | aaa | aaa | gca | 1680 |

```
His Ala Thr Ile Pro Gly Ala Asp Ala Glu Thr Val Lys Lys Lys Ala
545                 550                 555                 560 aag gag ttc tta aaa tac att aat cca aaa ctg ccc ggc ctg ctc gaa      1728
Lys Glu Phe Leu Lys Tyr Ile Asn Pro Lys Leu Pro Gly Leu Leu Glu
                565                 570                 575 ctt gag tac gag ggc ttc tac gtg agg ggc ttc ttc gtc acg aag aag      1776
Leu Glu Tyr Glu Gly Phe Tyr Val Arg Gly Phe Phe Val Thr Lys Lys
            580                 585                 590 aag tac gct gtg ata gac gag gag ggc aag ata acc acg agg ggt ctt      1824
Lys Tyr Ala Val Ile Asp Glu Glu Gly Lys Ile Thr Thr Arg Gly Leu
        595                 600                 605 gag att gtg agg cgc gac tgg agc gag ata gcg aag gag acc cag gcc      1872
Glu Ile Val Arg Arg Asp Trp Ser Glu Ile Ala Lys Glu Thr Gln Ala
    610                 615                 620 agg gtc tta gag gcg ata ctc aag cac ggt gac gtc gag gag gcc gtt      1920
Arg Val Leu Glu Ala Ile Leu Lys His Gly Asp Val Glu Glu Ala Val
625                 630                 635                 640 agg ata gtc aag gaa gtg acg gaa aag ctg agc aag tat gag gtc ccg      1968
Arg Ile Val Lys Glu Val Thr Glu Lys Leu Ser Lys Tyr Glu Val Pro
                645                 650                 655 ccc gag aag ctg gta atc cac gag cag ata acg cgc gat ttg agg gat      2016
Pro Glu Lys Leu Val Ile His Glu Gln Ile Thr Arg Asp Leu Arg Asp
            660                 665                 670 tac aaa gcc acc ggc ccg cac gtt gcc gtt gcg aag agg ctc gcg gcg      2064
Tyr Lys Ala Thr Gly Pro His Val Ala Val Ala Lys Arg Leu Ala Ala
        675                 680                 685 cgt gga gtg aaa atc cgg ccc ggc acg gtg ata agc tac atc gtc cta      2112
Arg Gly Val Lys Ile Arg Pro Gly Thr Val Ile Ser Tyr Ile Val Leu
    690                 695                 700 aag ggc tct gga agg ata ggc gac agg gcg att cca gct gat gag ttc      2160
Lys Gly Ser Gly Arg Ile Gly Asp Arg Ala Ile Pro Ala Asp Glu Phe
705                 710                 715                 720 gac ccg acg aag cac cgc tac gat gcg gaa tac tac atc gag aac cag      2208
Asp Pro Thr Lys His Arg Tyr Asp Ala Glu Tyr Tyr Ile Glu Asn Gln
                725                 730                 735 gtt ctc ccg gcg gtg gag agg att cta aaa gcc ttc ggc tat cgg aag      2256
Val Leu Pro Ala Val Glu Arg Ile Leu Lys Ala Phe Gly Tyr Arg Lys
            740                 745                 750 gag gat ttg cgc tac cag aag acg aag cag gtc ggc ttg ggc gcg tgg      2304
Glu Asp Leu Arg Tyr Gln Lys Thr Lys Gln Val Gly Leu Gly Ala Trp
        755                 760                 765 ctg aag gtg aag ggg aag aag tga                                      2328
Leu Lys Val Lys Gly Lys Lys
    770                 775

<210> SEQ ID NO 12
<211> LENGTH: 775
<212> TYPE: PRT
<213> ORGANISM: Artificial sequence
<220> FEATURE:
<223> OTHER INFORMATION: 9oN polymerase variant (exo-) with
      L408V/Y409A/P410L R484I/A485S/I486N mutations

<400> SEQUENCE: 12

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45
```

```
Glu Asp Val Lys Lys Val Thr Ala Lys Arg His Gly Thr Val Val Lys
     50                  55                  60

Val Lys Arg Ala Glu Lys Val Gln Lys Lys Phe Leu Gly Arg Pro Ile
 65              70                  75                      80

Glu Val Trp Lys Leu Tyr Phe Asn His Pro Gln Asp Val Pro Ala Ile
                 85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
        130                 135                 140

Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Val Ala Leu Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
```

```
                    465                 470                 475                 480
Tyr Arg Gln Ile Ser Asn Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
            515                 520                 525
Glu Glu Lys Phe Gly Phe Lys Val Leu Tyr Ala Asp Thr Asp Gly Leu
            530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
                580                 585                 590
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
            610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
                660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
            690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
                740                 745                 750
Glu Asp Leu Arg Tyr Gln Lys Thr Lys Gln Val Gly Leu Gly Ala Trp
            755                 760                 765
Leu Lys Val Lys Gly Lys Lys
    770                 775

<210> SEQ ID NO 13
<211> LENGTH: 2328
<212> TYPE: DNA
<213> ORGANISM: Thermococcus sp.
<220> FEATURE:
<221> NAME/KEY: CDS
<222> LOCATION: (1)..(2328)
<223> OTHER INFORMATION: coding sequence

<400> SEQUENCE: 13 atg att ctc gat acc gac tac atc acc gag aac ggg aag ccc gtg ata    48
Met Ile Leu Asp Thr Asp Tyr Ile Thr Glu Asn Gly Lys Pro Val Ile
1               5                   10                  15 agg gtc ttc aag aag gag aac ggc gag ttt aaa atc gag tac gac aga    96
Arg Val Phe Lys Lys Glu Asn Gly Glu Phe Lys Ile Glu Tyr Asp Arg
            20                  25                  30
```

| | | |
|---|---|---|
| acc ttc gag ccc tac ttc tac gcc ctt ctg aag gac gat tct gcg ata<br>Thr Phe Glu Pro Tyr Phe Tyr Ala Leu Leu Lys Asp Asp Ser Ala Ile<br>35               40               45 | 144 |
| gag gac gtc aag aag gta acc gca aag agg cac gga acg gtt gtc aag<br>Glu Asp Val Lys Lys Val Thr Ala Lys Arg His Gly Thr Val Val Lys<br>50               55               60 | 192 |
| gtg aag cgc gcc gag aag gtg cag aag aag ttc ctc ggc agg ccg ata<br>Val Lys Arg Ala Glu Lys Val Gln Lys Lys Phe Leu Gly Arg Pro Ile<br>65                  70              75               80 | 240 |
| gag gtc tgg aag ctc tac ttc aac cat cct cag gac gtc ccg gcg att<br>Glu Val Trp Lys Leu Tyr Phe Asn His Pro Gln Asp Val Pro Ala Ile<br>               85               90               95 | 288 |
| cga gac agg ata cgc gcc cac ccc gct gtc gtt gac atc tac gag tac<br>Arg Asp Arg Ile Arg Ala His Pro Ala Val Val Asp Ile Tyr Glu Tyr<br>              100             105            110 | 336 |
| gac ata ccc ttc gcc aag cgc tac ctc atc gac aag ggc ctg att ccg<br>Asp Ile Pro Phe Ala Lys Arg Tyr Leu Ile Asp Lys Gly Leu Ile Pro<br>             115            120            125 | 384 |
| atg gag ggc gac gag gag ctt acg atg ctc gcc ttc gcg atc gca acc<br>Met Glu Gly Asp Glu Glu Leu Thr Met Leu Ala Phe Ala Ile Ala Thr<br>130                 135            140 | 432 |
| ctc tat cac gag ggc gag gag ttc gga acc ggg ccg att ctc atg ata<br>Leu Tyr His Glu Gly Glu Glu Phe Gly Thr Gly Pro Ile Leu Met Ile<br>145                150            155            160 | 480 |
| agc tac gcc gac ggg agc gag gcg agg gtg ata acc tgg aag aag att<br>Ser Tyr Ala Asp Gly Ser Glu Ala Arg Val Ile Thr Trp Lys Lys Ile<br>                  165             170            175 | 528 |
| gac ctt ccg tac gtt gac gtc gtc tcg acc gag aag gag atg att aag<br>Asp Leu Pro Tyr Val Asp Val Val Ser Thr Glu Lys Glu Met Ile Lys<br>             180            185            190 | 576 |
| cgc ttc ctc cgc gtc gtc agg gag aag gac ccc gac gtg ctc atc acc<br>Arg Phe Leu Arg Val Val Arg Glu Lys Asp Pro Asp Val Leu Ile Thr<br>             195            200           205 | 624 |
| tac aac ggc gac aac ttc gac ttc gcc tac ctg aag aag cgc tgt gag<br>Tyr Asn Gly Asp Asn Phe Asp Phe Ala Tyr Leu Lys Lys Arg Cys Glu<br>210                 215            220 | 672 |
| gaa ctc gga ata aag ttc aca ctc ggc agg gac ggg agc gag ccg aag<br>Glu Leu Gly Ile Lys Phe Thr Leu Gly Arg Asp Gly Ser Glu Pro Lys<br>225                 230            235            240 | 720 |
| ata cag cga atg ggc gac cgc ttt gcc gtt gag gtg aag ggc agg att<br>Ile Gln Arg Met Gly Asp Arg Phe Ala Val Glu Val Lys Gly Arg Ile<br>                  245             250            255 | 768 |
| cac ttc gac ctc tac ccc gtc ata agg cgc acg ata aac ctc ccg acc<br>His Phe Asp Leu Tyr Pro Val Ile Arg Arg Thr Ile Asn Leu Pro Thr<br>             260            265            270 | 816 |
| tac acc ctt gag gcc gtt tac gag gcc gtc ttt gga aag ccc aag gag<br>Tyr Thr Leu Glu Ala Val Tyr Glu Ala Val Phe Gly Lys Pro Lys Glu<br>275                 280            285 | 864 |
| aag gtt tac gca gag gag ata gcg cag gcc tgg gag agc ggg gag ggc<br>Lys Val Tyr Ala Glu Glu Ile Ala Gln Ala Trp Glu Ser Gly Glu Gly<br>290                 295            300 | 912 |
| ctt gaa agg gtt gca aga tac tcg atg gag gac gct aag gtg acc tac<br>Leu Glu Arg Val Ala Arg Tyr Ser Met Glu Asp Ala Lys Val Thr Tyr<br>305                 310            315            320 | 960 |
| gag ctg gga agg gag ttc ttc ccg atg gag gcc cag ctt tcg agg ctt<br>Glu Leu Gly Arg Glu Phe Phe Pro Met Glu Ala Gln Leu Ser Arg Leu<br>             325            330            335 | 1008 |
| ata ggc cag agc ctc tgg gac gtc tcg cgc tcg agc acc gga aat ttg<br>Ile Gly Gln Ser Leu Trp Asp Val Ser Arg Ser Ser Thr Gly Asn Leu<br>             340            345            350 | 1056 |

```
gtg gag tgg ttc ctc ctg cgg aag gcc tac aag agg aac gag ctc gcc     1104
Val Glu Trp Phe Leu Leu Arg Lys Ala Tyr Lys Arg Asn Glu Leu Ala
        355                 360                 365 cca aac aag ccc gac gag agg gag ctc gcg aga cgg cgc ggg ggc tac     1152
Pro Asn Lys Pro Asp Glu Arg Glu Leu Ala Arg Arg Arg Gly Gly Tyr
    370                 375                 380 gct ggc ggg tac gtt aag gaa cca gag cgg gga ttg tgg gac aac att     1200
Ala Gly Gly Tyr Val Lys Glu Pro Glu Arg Gly Leu Trp Asp Asn Ile
385                 390                 395                 400 gtg tat tta gac ttc cgc tcg ctg tat cct tcg atc atc ata acc cac     1248
Val Tyr Leu Asp Phe Arg Ser Leu Tyr Pro Ser Ile Ile Ile Thr His
                405                 410                 415 aac gtc tcg ccg gat acc ctc aac cgc gag ggc tgt aaa gag tac gac     1296
Asn Val Ser Pro Asp Thr Leu Asn Arg Glu Gly Cys Lys Glu Tyr Asp
            420                 425                 430 gtc gcc cct gag gtt gga cac aag ttc tgc aag gac ttc ccc ggc ttc     1344
Val Ala Pro Glu Val Gly His Lys Phe Cys Lys Asp Phe Pro Gly Phe
        435                 440                 445 ata cca agc ctc ctg gga gat ttg ctc gag gag agg cag aag ata aag     1392
Ile Pro Ser Leu Leu Gly Asp Leu Leu Glu Glu Arg Gln Lys Ile Lys
    450                 455                 460 cgg aag atg aag gca acg gtt gac ccg ctg gag aag aaa ctc ctc gat     1440
Arg Lys Met Lys Ala Thr Val Asp Pro Leu Glu Lys Lys Leu Leu Asp
465                 470                 475                 480 tac agg cag agg gct atc aag atc ctc gcc aac agc ttc tac ggc tac     1488
Tyr Arg Gln Arg Ala Ile Lys Ile Leu Ala Asn Ser Phe Tyr Gly Tyr
                485                 490                 495 tac ggc tac gcc aag gcc cgg tgg tac tgc aag gag tgc gcc gag agc     1536
Tyr Gly Tyr Ala Lys Ala Arg Trp Tyr Cys Lys Glu Cys Ala Glu Ser
            500                 505                 510 gtt acg gcc tgg gga agg gag tat ata gaa atg gtt atc cgg gaa ctc     1584
Val Thr Ala Trp Gly Arg Glu Tyr Ile Glu Met Val Ile Arg Glu Leu
        515                 520                 525 gaa gaa aaa ttc ggt ttt aaa gtt ctc tat gcc gat aca gac ggt ctc     1632
Glu Glu Lys Phe Gly Phe Lys Val Leu Tyr Ala Asp Thr Asp Gly Leu
    530                 535                 540 cat gct acc att ccc gga gca gac gct gaa aca gtc aag aaa aaa gca     1680
His Ala Thr Ile Pro Gly Ala Asp Ala Glu Thr Val Lys Lys Lys Ala
545                 550                 555                 560 aag gag ttc tta aaa tac att aat cca aaa ctg ccc ggc ctg ctc gaa     1728
Lys Glu Phe Leu Lys Tyr Ile Asn Pro Lys Leu Pro Gly Leu Leu Glu
                565                 570                 575 ctt gag tac gag ggc ttc tac gtg agg ggc ttc ttc gtc acg aag aag     1776
Leu Glu Tyr Glu Gly Phe Tyr Val Arg Gly Phe Phe Val Thr Lys Lys
            580                 585                 590 aag tac gct gtg ata gac gag gag ggc aag ata acc acg agg ggt ctt     1824
Lys Tyr Ala Val Ile Asp Glu Glu Gly Lys Ile Thr Thr Arg Gly Leu
        595                 600                 605 gag att gtg agg cgc gac tgg agc gag ata gcg aag gag acc cag gcc     1872
Glu Ile Val Arg Arg Asp Trp Ser Glu Ile Ala Lys Glu Thr Gln Ala
    610                 615                 620 agg gtc tta gag gcg ata ctc aag cac ggt gac gtc gag gag gcc gtt     1920
Arg Val Leu Glu Ala Ile Leu Lys His Gly Asp Val Glu Glu Ala Val
625                 630                 635                 640 agg ata gtc aag gaa gtg acg gaa aag ctg agc aag tat gag gtc ccg     1968
Arg Ile Val Lys Glu Val Thr Glu Lys Leu Ser Lys Tyr Glu Val Pro
                645                 650                 655 ccc gag aag ctg gta atc cac gag cag ata acg cgc gat ttg agg gat     2016
Pro Glu Lys Leu Val Ile His Glu Gln Ile Thr Arg Asp Leu Arg Asp
```

```
                     660                 665                 670
tac aaa gcc acc ggc ccg cac gtt gcc gtt gcg aag agg ctc gcg gcg       2064
Tyr Lys Ala Thr Gly Pro His Val Ala Val Ala Lys Arg Leu Ala Ala
            675                 680                 685 cgt gga gtg aaa atc cgg ccc ggc acg gtg ata agc tac atc gtc cta       2112
Arg Gly Val Lys Ile Arg Pro Gly Thr Val Ile Ser Tyr Ile Val Leu
        690                 695                 700 aag ggc tct gga agg ata ggc gac agg gcg att cca gct gat gag ttc       2160
Lys Gly Ser Gly Arg Ile Gly Asp Arg Ala Ile Pro Ala Asp Glu Phe
705                 710                 715                 720 gac ccg acg aag cac cgc tac gat gcg gaa tac tac atc gag aac cag       2208
Asp Pro Thr Lys His Arg Tyr Asp Ala Glu Tyr Tyr Ile Glu Asn Gln
                725                 730                 735 gtt ctc ccg gcg gtg gag agg att cta aaa gcc ttc ggc tat cgg aag       2256
Val Leu Pro Ala Val Glu Arg Ile Leu Lys Ala Phe Gly Tyr Arg Lys
            740                 745                 750 gag gat ttg cgc tac cag aag acg aag cag gtc ggc ttg ggc gcg tgg       2304
Glu Asp Leu Arg Tyr Gln Lys Thr Lys Gln Val Gly Leu Gly Ala Trp
        755                 760                 765 ctg aag gtg aag ggg aag aag tga                                       2328
Leu Lys Val Lys Gly Lys Lys
770                 775

<210> SEQ ID NO 14
<211> LENGTH: 775
<212> TYPE: PRT
<213> ORGANISM: Thermococcus sp.

<400> SEQUENCE: 14

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220
```

```
Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640
```

-continued

```
Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
        660                 665                 670

Tyr Lys Ala Thr Gly Pro His Val Ala Val Ala Lys Arg Leu Ala Ala
    675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys
    770                 775
```

<210> SEQ ID NO 15
<211> LENGTH: 2328
<212> TYPE: DNA
<213> ORGANISM: Artificial sequence
<220> FEATURE:
<223> OTHER INFORMATION: 9oN polymerase (exo-) with Y409V and A485L
      mutations
<220> FEATURE:
<221> NAME/KEY: CDS
<222> LOCATION: (1)..(2328)
<223> OTHER INFORMATION: coding sequence

<400> SEQUENCE: 15

```
atg att ctc gat acc gac tac atc acc gag aac ggg aag ccc gtg ata      48
Met Ile Leu Asp Thr Asp Tyr Ile Thr Glu Asn Gly Lys Pro Val Ile
1               5                   10                  15 agg gtc ttc aag aag gag aac ggc gag ttt aaa atc gag tac gac aga      96
Arg Val Phe Lys Lys Glu Asn Gly Glu Phe Lys Ile Glu Tyr Asp Arg
            20                  25                  30 acc ttc gag ccc tac ttc tac gcc ctt ctg aag gac gat tct gcg ata     144
Thr Phe Glu Pro Tyr Phe Tyr Ala Leu Leu Lys Asp Asp Ser Ala Ile
        35                  40                  45 gag gac gtc aag aag gta acc gca aag agg cac gga acg gtt gtc aag     192
Glu Asp Val Lys Lys Val Thr Ala Lys Arg His Gly Thr Val Val Lys
    50                  55                  60 gtg aag cgc gcc gag aag gtg cag aag aag ttc ctc ggc agg ccg ata     240
Val Lys Arg Ala Glu Lys Val Gln Lys Lys Phe Leu Gly Arg Pro Ile
65                  70                  75                  80 gag gtc tgg aag ctc tac ttc aac cat cct cag gac gtc ccg gcg att     288
Glu Val Trp Lys Leu Tyr Phe Asn His Pro Gln Asp Val Pro Ala Ile
                85                  90                  95 cga gac agg ata cgc gcc cac ccc gct gtc gtt gac atc tac gag tac     336
Arg Asp Arg Ile Arg Ala His Pro Ala Val Val Asp Ile Tyr Glu Tyr
            100                 105                 110 gac ata ccc ttc gcc aag cgc tac ctc atc gac aag ggc ctg att ccg     384
Asp Ile Pro Phe Ala Lys Arg Tyr Leu Ile Asp Lys Gly Leu Ile Pro
        115                 120                 125 atg gag ggc gac gag gag ctt acg atg ctc gcc ttc gcg atc gca acc     432
Met Glu Gly Asp Glu Glu Leu Thr Met Leu Ala Phe Ala Ile Ala Thr
    130                 135                 140 ctc tat cac gag ggc gag gag ttc gga acc ggg ccg att ctc atg ata     480
```

```
Leu Tyr His Glu Gly Glu Glu Phe Gly Thr Gly Pro Ile Leu Met Ile
145                 150                 155                 160 agc tac gcc gac ggg agc gag gcg agg gtg ata acc tgg aag aag att     528
Ser Tyr Ala Asp Gly Ser Glu Ala Arg Val Ile Thr Trp Lys Lys Ile
                    165                 170                 175 gac ctt ccg tac gtt gac gtc gtc tcg acc gag aag gag atg att aag     576
Asp Leu Pro Tyr Val Asp Val Val Ser Thr Glu Lys Glu Met Ile Lys
                180                 185                 190 cgc ttc ctc cgc gtc gtc agg gag aag gac ccc gac gtg ctc atc acc     624
Arg Phe Leu Arg Val Val Arg Glu Lys Asp Pro Asp Val Leu Ile Thr
            195                 200                 205 tac aac ggc gac aac ttc gac ttc gcc tac ctg aag aag cgc tgt gag     672
Tyr Asn Gly Asp Asn Phe Asp Phe Ala Tyr Leu Lys Lys Arg Cys Glu
        210                 215                 220 gaa ctc gga ata aag ttc aca ctc ggc agg gac ggg agc gag ccg aag     720
Glu Leu Gly Ile Lys Phe Thr Leu Gly Arg Asp Gly Ser Glu Pro Lys
225                 230                 235                 240 ata cag cga atg ggc gac cgc ttt gcc gtt gag gtg aag ggc agg att     768
Ile Gln Arg Met Gly Asp Arg Phe Ala Val Glu Val Lys Gly Arg Ile
                    245                 250                 255 cac ttc gac ctc tac ccc gtc ata agg cgc acg ata aac ctc ccg acc     816
His Phe Asp Leu Tyr Pro Val Ile Arg Arg Thr Ile Asn Leu Pro Thr
                260                 265                 270 tac acc ctt gag gcc gtt tac gag gcc gtc ttt gga aag ccc aag gag     864
Tyr Thr Leu Glu Ala Val Tyr Glu Ala Val Phe Gly Lys Pro Lys Glu
            275                 280                 285 aag gtt tac gca gag gag ata gcg cag gcc tgg gag agc ggg gag ggc     912
Lys Val Tyr Ala Glu Glu Ile Ala Gln Ala Trp Glu Ser Gly Glu Gly
        290                 295                 300 ctt gaa agg gtt gca aga tac tcg atg gag gac gct aag gtg acc tac     960
Leu Glu Arg Val Ala Arg Tyr Ser Met Glu Asp Ala Lys Val Thr Tyr
305                 310                 315                 320 gag ctg gga agg gag ttc ttc ccg atg gag gcc cag ctt tcg agg ctt    1008
Glu Leu Gly Arg Glu Phe Phe Pro Met Glu Ala Gln Leu Ser Arg Leu
                    325                 330                 335 ata ggc cag agc ctc tgg gac gtc tcg cgc tcg agc acc gga aat ttg    1056
Ile Gly Gln Ser Leu Trp Asp Val Ser Arg Ser Ser Thr Gly Asn Leu
                340                 345                 350 gtg gag tgg ttc ctc ctg cgg aag gcc tac aag agg aac gag ctc gcc    1104
Val Glu Trp Phe Leu Leu Arg Lys Ala Tyr Lys Arg Asn Glu Leu Ala
            355                 360                 365 cca aac aag ccc gac gag agg gag ctc gcg aga cgg cgc ggg ggc tac    1152
Pro Asn Lys Pro Asp Glu Arg Glu Leu Ala Arg Arg Arg Gly Gly Tyr
        370                 375                 380 gct ggc ggg tac gtt aag gaa cca gag cgg gga ttg tgg gac aac att    1200
Ala Gly Gly Tyr Val Lys Glu Pro Glu Arg Gly Leu Trp Asp Asn Ile
385                 390                 395                 400 gtg tat tta gac ttc cgc tcg ctg gtg cct tca atc atc ata acc cac    1248
Val Tyr Leu Asp Phe Arg Ser Leu Val Pro Ser Ile Ile Ile Thr His
                    405                 410                 415 aac gtc tcg ccg gat acc ctc aac cgc gag ggc tgt aaa gag tac gac    1296
Asn Val Ser Pro Asp Thr Leu Asn Arg Glu Gly Cys Lys Glu Tyr Asp
                420                 425                 430 gtc gcc cct gag gtt gga cac aag ttc tgc aag gac ttc ccc ggc ttc    1344
Val Ala Pro Glu Val Gly His Lys Phe Cys Lys Asp Phe Pro Gly Phe
            435                 440                 445 ata cca agc ctc ctg gga gat ttg ctc gag gag agg cag aag ata aag    1392
Ile Pro Ser Leu Leu Gly Asp Leu Leu Glu Glu Arg Gln Lys Ile Lys
        450                 455                 460
```

```
                                            -continued cgg aag atg aag gca acg gtt gac ccg ctg gag aag aaa ctc ctc gat    1440
Arg Lys Met Lys Ala Thr Val Asp Pro Leu Glu Lys Lys Leu Leu Asp
465             470                 475                 480 tac agg cag agg ctg atc aaa atc ctc gcc aac agc ttc tac ggc tac    1488
Tyr Arg Gln Arg Leu Ile Lys Ile Leu Ala Asn Ser Phe Tyr Gly Tyr
            485                 490                 495 tac ggc tac gcc aag gcc cgg tgg tac tgc aag gag tgc gcc gag agc    1536
Tyr Gly Tyr Ala Lys Ala Arg Trp Tyr Cys Lys Glu Cys Ala Glu Ser
        500                 505                 510 gtt acg gcc tgg gga agg gag tat ata gaa atg gtt atc cgg gaa ctc    1584
Val Thr Ala Trp Gly Arg Glu Tyr Ile Glu Met Val Ile Arg Glu Leu
    515                 520                 525 gaa gaa aaa ttc ggt ttt aaa gtt ctc tat gcc gat aca gac ggt ctc    1632
Glu Glu Lys Phe Gly Phe Lys Val Leu Tyr Ala Asp Thr Asp Gly Leu
530                 535                 540 cat gct acc att ccc gga gca gac gct gaa aca gtc aag aaa aaa gca    1680
His Ala Thr Ile Pro Gly Ala Asp Ala Glu Thr Val Lys Lys Lys Ala
545                 550                 555                 560 aag gag ttc tta aaa tac att aat cca aaa ctg ccc ggc ctg ctc gaa    1728
Lys Glu Phe Leu Lys Tyr Ile Asn Pro Lys Leu Pro Gly Leu Leu Glu
            565                 570                 575 ctt gag tac gag ggc ttc tac gtg agg ggc ttc ttc gtc acg aag aag    1776
Leu Glu Tyr Glu Gly Phe Tyr Val Arg Gly Phe Phe Val Thr Lys Lys
        580                 585                 590 aag tac gct gtg ata gac gag gag ggc aag ata acc acg agg ggt ctt    1824
Lys Tyr Ala Val Ile Asp Glu Glu Gly Lys Ile Thr Thr Arg Gly Leu
    595                 600                 605 gag att gtg agg cgc gac tgg agc gag ata gcg aag gag acc cag gcc    1872
Glu Ile Val Arg Arg Asp Trp Ser Glu Ile Ala Lys Glu Thr Gln Ala
610                 615                 620 agg gtc tta gag gcg ata ctc aag cac ggt gac gtc gag gag gcc gtt    1920
Arg Val Leu Glu Ala Ile Leu Lys His Gly Asp Val Glu Glu Ala Val
625                 630                 635                 640 agg ata gtc aag gaa gtg acg gaa aag ctg agc aag tat gag gtc ccg    1968
Arg Ile Val Lys Glu Val Thr Glu Lys Leu Ser Lys Tyr Glu Val Pro
            645                 650                 655 ccc gag aag ctg gta atc cac gag cag ata acg cgc gat ttg agg gat    2016
Pro Glu Lys Leu Val Ile His Glu Gln Ile Thr Arg Asp Leu Arg Asp
        660                 665                 670 tac aaa gcc acc ggc ccg cac gtt gcc gtt gcg aag agg ctc gcg gcg    2064
Tyr Lys Ala Thr Gly Pro His Val Ala Val Ala Lys Arg Leu Ala Ala
    675                 680                 685 cgt gga gtg aaa atc cgg ccc ggc acg gtg ata agc tac atc gtc cta    2112
Arg Gly Val Lys Ile Arg Pro Gly Thr Val Ile Ser Tyr Ile Val Leu
690                 695                 700 aag ggc tct gga agg ata ggc gac agg gcg att cca gct gat gag ttc    2160
Lys Gly Ser Gly Arg Ile Gly Asp Arg Ala Ile Pro Ala Asp Glu Phe
705                 710                 715                 720 gac ccg acg aag cac cgc tac gat gcg gaa tac tac atc gag aac cag    2208
Asp Pro Thr Lys His Arg Tyr Asp Ala Glu Tyr Tyr Ile Glu Asn Gln
            725                 730                 735 gtt ctc ccg gcg gtg gag agg att cta aaa gcc ttc ggc tat cgg aag    2256
Val Leu Pro Ala Val Glu Arg Ile Leu Lys Ala Phe Gly Tyr Arg Lys
        740                 745                 750 gag gat ttg cgc tac cag aag acg aag cag gtc ggc ttg ggc gcg tgg    2304
Glu Asp Leu Arg Tyr Gln Lys Thr Lys Gln Val Gly Leu Gly Ala Trp
    755                 760                 765 ctg aag gtg aag ggg aag aag tga                                    2328
Leu Lys Val Lys Gly Lys Lys
770                 775
```

<210> SEQ ID NO 16
<211> LENGTH: 775
<212> TYPE: PRT
<213> ORGANISM: Artificial sequence
<220> FEATURE:
<223> OTHER INFORMATION: 9oN polymerase (exo-) with Y409V and A485L mutations

<400> SEQUENCE: 16

```
Met Ile Leu Asp Thr Asp Tyr Ile Thr Glu Asn Gly Lys Pro Val Ile
  1               5                  10                  15

Arg Val Phe Lys Lys Glu Asn Gly Glu Phe Lys Ile Glu Tyr Asp Arg
             20                  25                  30

Thr Phe Glu Pro Tyr Phe Tyr Ala Leu Leu Lys Asp Asp Ser Ala Ile
         35                  40                  45

Glu Asp Val Lys Lys Val Thr Ala Lys Arg His Gly Thr Val Val Lys
     50                  55                  60

Val Lys Arg Ala Glu Lys Val Gln Lys Phe Leu Gly Arg Pro Ile
 65                  70                  75                  80

Glu Val Trp Lys Leu Tyr Phe Asn His Pro Gln Asp Val Pro Ala Ile
                 85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
```

```
                355                 360                 365
Pro Asn Lys Pro Asp Glu Arg Glu Leu Ala Arg Arg Gly Gly Tyr
    370                 375                 380
Ala Gly Tyr Val Lys Glu Pro Glu Arg Gly Leu Trp Asp Asn Ile
385                 390                 395                 400
Val Tyr Leu Asp Phe Arg Ser Leu Val Pro Ser Ile Ile Thr His
                405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
            435                 440                 445
Ile Pro Ser Leu Leu Gly Asp Leu Leu Glu Glu Arg Gln Lys Ile Lys
        450                 455                 460
Arg Lys Met Lys Ala Thr Val Asp Pro Leu Glu Lys Lys Leu Leu Asp
465                 470                 475                 480
Tyr Arg Gln Arg Leu Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
            515                 520                 525
Glu Glu Lys Phe Gly Phe Lys Val Leu Tyr Ala Asp Thr Asp Gly Leu
        530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
            580                 585                 590
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
        690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
            740                 745                 750
Glu Asp Leu Arg Tyr Gln Lys Thr Lys Gln Val Gly Leu Gly Ala Trp
            755                 760                 765
Leu Lys Val Lys Gly Lys Lys
        770                 775
```

<210> SEQ ID NO 17
<211> LENGTH: 2328
<212> TYPE: DNA
<213> ORGANISM: Artificial sequence
<220> FEATURE:
<223> OTHER INFORMATION: 9oN polymerase variant (exo-) with
      L408V/Y409A/P410L and A485L mutations
<220> FEATURE:
<221> NAME/KEY: CDS
<222> LOCATION: (1)..(2328)
<223> OTHER INFORMATION: coding sequence

<400> SEQUENCE: 17

```
atg att ctc gat acc gac tac atc acc gag aac ggg aag ccc gtg ata      48
Met Ile Leu Asp Thr Asp Tyr Ile Thr Glu Asn Gly Lys Pro Val Ile
1               5                   10                  15 agg gtc ttc aag aag gag aac ggc gag ttt aaa atc gag tac gac aga      96
Arg Val Phe Lys Lys Glu Asn Gly Glu Phe Lys Ile Glu Tyr Asp Arg
                20                  25                  30 acc ttc gag ccc tac ttc tac gcc ctt ctg aag gac gat tct gcg ata     144
Thr Phe Glu Pro Tyr Phe Tyr Ala Leu Leu Lys Asp Asp Ser Ala Ile
            35                  40                  45 gag gac gtc aag aag gta acc gca aag agg cac gga acg gtt gtc aag     192
Glu Asp Val Lys Lys Val Thr Ala Lys Arg His Gly Thr Val Val Lys
        50                  55                  60 gtg aag cgc gcc gag aag gtg cag aag aag ttc ctc ggc agg ccg ata     240
Val Lys Arg Ala Glu Lys Val Gln Lys Lys Phe Leu Gly Arg Pro Ile
65                  70                  75                  80 gag gtc tgg aag ctc tac ttc aac cat cct cag gac gtc ccg gcg att     288
Glu Val Trp Lys Leu Tyr Phe Asn His Pro Gln Asp Val Pro Ala Ile
                85                  90                  95 cga gac agg ata cgc gcc cac ccc gct gtc gtt gac atc tac gag tac     336
Arg Asp Arg Ile Arg Ala His Pro Ala Val Val Asp Ile Tyr Glu Tyr
                100                 105                 110 gac ata ccc ttc gcc aag cgc tac ctc atc gac aag ggc ctg att ccg     384
Asp Ile Pro Phe Ala Lys Arg Tyr Leu Ile Asp Lys Gly Leu Ile Pro
            115                 120                 125 atg gag ggc gac gag gag ctt acg atg ctc gcc ttc gcg atc gca acc     432
Met Glu Gly Asp Glu Glu Leu Thr Met Leu Ala Phe Ala Ile Ala Thr
        130                 135                 140 ctc tat cac gag ggc gag gag ttc gga acc ggg ccg att ctc atg ata     480
Leu Tyr His Glu Gly Glu Glu Phe Gly Thr Gly Pro Ile Leu Met Ile
145                 150                 155                 160 agc tac gcc gac ggg agc gag gcg agg gtg ata acc tgg aag aag att     528
Ser Tyr Ala Asp Gly Ser Glu Ala Arg Val Ile Thr Trp Lys Lys Ile
                165                 170                 175 gac ctt ccg tac gtt gac gtc gtc tcg acc gag aag gag atg att aag     576
Asp Leu Pro Tyr Val Asp Val Val Ser Thr Glu Lys Glu Met Ile Lys
                180                 185                 190 cgc ttc ctc cgc gtc gtc agg gag aag gac ccc gac gtg ctc atc acc     624
Arg Phe Leu Arg Val Val Arg Glu Lys Asp Pro Asp Val Leu Ile Thr
            195                 200                 205 tac aac ggc gac aac ttc gac ttc gcc tac ctg aag aag cgc tgt gag     672
Tyr Asn Gly Asp Asn Phe Asp Phe Ala Tyr Leu Lys Lys Arg Cys Glu
        210                 215                 220 gaa ctc gga ata aag ttc aca ctc ggc agg gac ggg agc gag ccg aag     720
Glu Leu Gly Ile Lys Phe Thr Leu Gly Arg Asp Gly Ser Glu Pro Lys
225                 230                 235                 240 ata cag cga atg ggc gac cgc ttt gcc gtt gag gtg aag ggc agg att     768
Ile Gln Arg Met Gly Asp Arg Phe Ala Val Glu Val Lys Gly Arg Ile
                245                 250                 255
```

| | | | | | | | | | | | | | | | | |
|---|---|---|---|---|---|---|---|---|---|---|---|---|---|---|---|---|
| cac | ttc | gac | ctc | tac | ccc | gtc | ata | agg | cgc | acg | ata | aac | ctc | ccg | acc | 816 |
| His | Phe | Asp | Leu | Tyr | Pro | Val | Ile | Arg | Arg | Thr | Ile | Asn | Leu | Pro | Thr | |
| | | | 260 | | | | | 265 | | | | | 270 | | | |
| tac | acc | ctt | gag | gcc | gtt | tac | gag | gcc | gtc | ttt | gga | aag | ccc | aag | gag | 864 |
| Tyr | Thr | Leu | Glu | Ala | Val | Tyr | Glu | Ala | Val | Phe | Gly | Lys | Pro | Lys | Glu | |
| | | 275 | | | | | 280 | | | | | 285 | | | | |
| aag | gtt | tac | gca | gag | gag | ata | gcg | cag | gcc | tgg | gag | agc | ggg | gag | ggc | 912 |
| Lys | Val | Tyr | Ala | Glu | Glu | Ile | Ala | Gln | Ala | Trp | Glu | Ser | Gly | Glu | Gly | |
| | 290 | | | | | 295 | | | | | 300 | | | | | |
| ctt | gaa | agg | gtt | gca | aga | tac | tcg | atg | gag | gac | gct | aag | gtg | acc | tac | 960 |
| Leu | Glu | Arg | Val | Ala | Arg | Tyr | Ser | Met | Glu | Asp | Ala | Lys | Val | Thr | Tyr | |
| 305 | | | | | 310 | | | | | 315 | | | | | 320 | |
| gag | ctg | gga | agg | gag | ttc | ttc | ccg | atg | gag | gcc | cag | ctt | tcg | agg | ctt | 1008 |
| Glu | Leu | Gly | Arg | Glu | Phe | Phe | Pro | Met | Glu | Ala | Gln | Leu | Ser | Arg | Leu | |
| | | | | 325 | | | | | 330 | | | | | 335 | | |
| ata | ggc | cag | agc | ctc | tgg | gac | gtc | tcg | cgc | tcg | agc | acc | gga | aat | ttg | 1056 |
| Ile | Gly | Gln | Ser | Leu | Trp | Asp | Val | Ser | Arg | Ser | Ser | Thr | Gly | Asn | Leu | |
| | | | 340 | | | | | 345 | | | | | 350 | | | |
| gtg | gag | tgg | ttc | ctc | ctg | cgg | aag | gcc | tac | aag | agg | aac | gag | ctc | gcc | 1104 |
| Val | Glu | Trp | Phe | Leu | Leu | Arg | Lys | Ala | Tyr | Lys | Arg | Asn | Glu | Leu | Ala | |
| | | 355 | | | | | 360 | | | | | 365 | | | | |
| cca | aac | aag | ccc | gac | gag | agg | gag | ctc | gcg | aga | cgg | cgc | ggg | ggc | tac | 1152 |
| Pro | Asn | Lys | Pro | Asp | Glu | Arg | Glu | Leu | Ala | Arg | Arg | Arg | Gly | Gly | Tyr | |
| | 370 | | | | | 375 | | | | | 380 | | | | | |
| gct | ggc | ggg | tac | gtt | aag | gaa | cca | gag | cgg | gga | ttg | tgg | gac | aac | att | 1200 |
| Ala | Gly | Gly | Tyr | Val | Lys | Glu | Pro | Glu | Arg | Gly | Leu | Trp | Asp | Asn | Ile | |
| 385 | | | | | 390 | | | | | 395 | | | | | 400 | |
| gtg | tat | tta | gac | ttc | cgc | tcg | gtt | gcg | ttg | tcg | atc | atc | ata | acc | cac | 1248 |
| Val | Tyr | Leu | Asp | Phe | Arg | Ser | Val | Ala | Leu | Ser | Ile | Ile | Ile | Thr | His | |
| | | | | 405 | | | | | 410 | | | | | 415 | | |
| aac | gtc | tcg | ccg | gat | acc | ctc | aac | cgc | gag | ggc | tgt | aaa | gag | tac | gac | 1296 |
| Asn | Val | Ser | Pro | Asp | Thr | Leu | Asn | Arg | Glu | Gly | Cys | Lys | Glu | Tyr | Asp | |
| | | | 420 | | | | | 425 | | | | | 430 | | | |
| gtc | gcc | cct | gag | gtt | gga | cac | aag | ttc | tgc | aag | gac | ttc | ccc | ggc | ttc | 1344 |
| Val | Ala | Pro | Glu | Val | Gly | His | Lys | Phe | Cys | Lys | Asp | Phe | Pro | Gly | Phe | |
| | | 435 | | | | | 440 | | | | | 445 | | | | |
| ata | cca | agc | ctc | ctg | gga | gat | ttg | ctc | gag | gag | agg | cag | aag | ata | aag | 1392 |
| Ile | Pro | Ser | Leu | Leu | Gly | Asp | Leu | Leu | Glu | Glu | Arg | Gln | Lys | Ile | Lys | |
| | 450 | | | | | 455 | | | | | 460 | | | | | |
| cgg | aag | atg | aag | gca | acg | gtt | gac | ccg | ctg | gag | aag | aaa | ctc | ctc | gat | 1440 |
| Arg | Lys | Met | Lys | Ala | Thr | Val | Asp | Pro | Leu | Glu | Lys | Lys | Leu | Leu | Asp | |
| 465 | | | | | 470 | | | | | 475 | | | | | 480 | |
| tac | agg | cag | agg | ctg | atc | aaa | atc | ctc | gcc | aac | agc | ttc | tac | ggc | tac | 1488 |
| Tyr | Arg | Gln | Arg | Leu | Ile | Lys | Ile | Leu | Ala | Asn | Ser | Phe | Tyr | Gly | Tyr | |
| | | | | 485 | | | | | 490 | | | | | 495 | | |
| tac | ggc | tac | gcc | aag | gcc | cgg | tgg | tac | tgc | aag | gag | tgc | gcc | gag | agc | 1536 |
| Tyr | Gly | Tyr | Ala | Lys | Ala | Arg | Trp | Tyr | Cys | Lys | Glu | Cys | Ala | Glu | Ser | |
| | | | 500 | | | | | 505 | | | | | 510 | | | |
| gtt | acg | gcc | tgg | gga | agg | gag | tat | ata | gaa | atg | gtt | atc | cgg | gaa | ctc | 1584 |
| Val | Thr | Ala | Trp | Gly | Arg | Glu | Tyr | Ile | Glu | Met | Val | Ile | Arg | Glu | Leu | |
| | | 515 | | | | | 520 | | | | | 525 | | | | |
| gaa | gaa | aaa | ttc | ggt | ttt | aaa | gtt | ctc | tat | gcc | gat | aca | gac | ggt | ctc | 1632 |
| Glu | Glu | Lys | Phe | Gly | Phe | Lys | Val | Leu | Tyr | Ala | Asp | Thr | Asp | Gly | Leu | |
| | 530 | | | | | 535 | | | | | 540 | | | | | |
| cat | gct | acc | att | ccc | gga | gca | gac | gct | gaa | aca | gtc | aag | aaa | aaa | gca | 1680 |
| His | Ala | Thr | Ile | Pro | Gly | Ala | Asp | Ala | Glu | Thr | Val | Lys | Lys | Lys | Ala | |
| 545 | | | | | 550 | | | | | 555 | | | | | 560 | |
| aag | gag | ttc | tta | aaa | tac | att | aat | cca | aaa | ctg | ccc | ggc | ctg | ctc | gaa | 1728 |
| Lys | Glu | Phe | Leu | Lys | Tyr | Ile | Asn | Pro | Lys | Leu | Pro | Gly | Leu | Leu | Glu | |

-continued

```
                   565                 570                 575
ctt gag tac gag ggc ttc tac gtg agg ggc ttc ttc gtc acg aag aag     1776
Leu Glu Tyr Glu Gly Phe Tyr Val Arg Gly Phe Phe Val Thr Lys Lys
                   580                 585                 590 aag tac gct gtg ata gac gag gag ggc aag ata acc acg agg ggt ctt     1824
Lys Tyr Ala Val Ile Asp Glu Glu Gly Lys Ile Thr Thr Arg Gly Leu
               595                 600                 605 gag att gtg agg cgc gac tgg agc gag ata gcg aag gag acc cag gcc     1872
Glu Ile Val Arg Arg Asp Trp Ser Glu Ile Ala Lys Glu Thr Gln Ala
           610                 615                 620 agg gtc tta gag gcg ata ctc aag cac ggt gac gtc gag gag gcc gtt     1920
Arg Val Leu Glu Ala Ile Leu Lys His Gly Asp Val Glu Glu Ala Val
625                 630                 635                 640 agg ata gtc aag gaa gtg acg gaa aag ctg agc aag tat gag gtc ccg     1968
Arg Ile Val Lys Glu Val Thr Glu Lys Leu Ser Lys Tyr Glu Val Pro
                   645                 650                 655 ccc gag aag ctg gta atc cac gag cag ata acg cgc gat ttg agg gat     2016
Pro Glu Lys Leu Val Ile His Glu Gln Ile Thr Arg Asp Leu Arg Asp
               660                 665                 670 tac aaa gcc acc ggc ccg cac gtt gcc gtt gcg aag agg ctc gcg gcg     2064
Tyr Lys Ala Thr Gly Pro His Val Ala Val Ala Lys Arg Leu Ala Ala
           675                 680                 685 cgt gga gtg aaa atc cgg ccc ggc acg gtg ata agc tac atc gtc cta     2112
Arg Gly Val Lys Ile Arg Pro Gly Thr Val Ile Ser Tyr Ile Val Leu
       690                 695                 700 aag ggc tct gga agg ata ggc gac agg gcg att cca gct gat gag ttc     2160
Lys Gly Ser Gly Arg Ile Gly Asp Arg Ala Ile Pro Ala Asp Glu Phe
705                 710                 715                 720 gac ccg acg aag cac cgc tac gat gcg gaa tac tac atc gag aac cag     2208
Asp Pro Thr Lys His Arg Tyr Asp Ala Glu Tyr Tyr Ile Glu Asn Gln
                   725                 730                 735 gtt ctc ccg gcg gtg gag agg att cta aaa gcc ttc ggc tat cgg aag     2256
Val Leu Pro Ala Val Glu Arg Ile Leu Lys Ala Phe Gly Tyr Arg Lys
               740                 745                 750 gag gat ttg cgc tac cag aag acg aag cag gtc ggc ttg ggc gcg tgg     2304
Glu Asp Leu Arg Tyr Gln Lys Thr Lys Gln Val Gly Leu Gly Ala Trp
           755                 760                 765 ctg aag gtg aag ggg aag aag tga                                     2328
Leu Lys Val Lys Gly Lys Lys
       770                 775
```

<210> SEQ ID NO 18
<211> LENGTH: 775
<212> TYPE: PRT
<213> ORGANISM: Artificial sequence
<220> FEATURE:
<223> OTHER INFORMATION: 9oN polymerase variant (exo-) with
    L408V/Y409A/P410L and A485L mutations

<400> SEQUENCE: 18

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80
```

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
                180                 185                 190

Arg Phe Leu Arg Val Val Arg Glu Lys Asp Pro Asp Val Leu Ile Thr
                195                 200                 205

Tyr Asn Gly Asp Asn Phe Asp Phe Ala Tyr Leu Lys Lys Arg Cys Glu
                210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
                275                 280                 285

Lys Val Tyr Ala Glu Glu Ile Ala Gln Ala Trp Glu Ser Gly Glu Gly
                290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
                355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Val Ala Leu Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

```
Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
    515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 19
<211> LENGTH: 2328
<212> TYPE: DNA
<213> ORGANISM: Artificial sequence
<220> FEATURE:
<223> OTHER INFORMATION: 9oN polymerase variant (exo-) with
      L408Y/Y409A/P410S mutations
<220> FEATURE:
<221> NAME/KEY: CDS
<222> LOCATION: (1)..(2328)
<223> OTHER INFORMATION: coding sequence

<400> SEQUENCE: 19 atg att ctc gat acc gac tac atc acc gag aac ggg aag ccc gtg ata      48
Met Ile Leu Asp Thr Asp Tyr Ile Thr Glu Asn Gly Lys Pro Val Ile
1               5                   10                  15 agg gtc ttc aag aag gag aac ggc gag ttt aaa atc gag tac gac aga      96
Arg Val Phe Lys Lys Glu Asn Gly Glu Phe Lys Ile Glu Tyr Asp Arg
            20                  25                  30 acc ttc gag ccc tac ttc tac gcc ctt ctg aag gac gat tct gcg ata     144
Thr Phe Glu Pro Tyr Phe Tyr Ala Leu Leu Lys Asp Asp Ser Ala Ile
```

|  |  |
|---|---:|
| gag gac gtc aag aag gta acc gca aag agg cac gga acg gtt gtc aag<br>Glu Asp Val Lys Lys Val Thr Ala Lys Arg His Gly Thr Val Val Lys<br>50                      55                      60 | 192 |
| gtg aag cgc gcc gag aag gtg cag aag aag ttc ctc ggc agg ccg ata<br>Val Lys Arg Ala Glu Lys Val Gln Lys Lys Phe Leu Gly Arg Pro Ile<br>65                      70                      75                      80 | 240 |
| gag gtc tgg aag ctc tac ttc aac cat cct cag gac gtc ccg gcg att<br>Glu Val Trp Lys Leu Tyr Phe Asn His Pro Gln Asp Val Pro Ala Ile<br>                    85                      90                      95 | 288 |
| cga gac agg ata cgc gcc cac ccc gct gtc gtt gac atc tac gag tac<br>Arg Asp Arg Ile Arg Ala His Pro Ala Val Val Asp Ile Tyr Glu Tyr<br>                100                   105                 110 | 336 |
| gac ata ccc ttc gcc aag cgc tac ctc atc gac aag ggc ctg att ccg<br>Asp Ile Pro Phe Ala Lys Arg Tyr Leu Ile Asp Lys Gly Leu Ile Pro<br>115                      120                     125 | 384 |
| atg gag ggc gac gag gag ctt acg atg ctc gcc ttc gcg atc gca acc<br>Met Glu Gly Asp Glu Glu Leu Thr Met Leu Ala Phe Ala Ile Ala Thr<br>130                      135                     140 | 432 |
| ctc tat cac gag ggc gag gag ttc gga acc ggg ccg att ctc atg ata<br>Leu Tyr His Glu Gly Glu Glu Phe Gly Thr Gly Pro Ile Leu Met Ile<br>145                      150                     155                 160 | 480 |
| agc tac gcc gac ggg agc gag gcg agg gtg ata acc tgg aag aag att<br>Ser Tyr Ala Asp Gly Ser Glu Ala Arg Val Ile Thr Trp Lys Lys Ile<br>                165                   170                 175 | 528 |
| gac ctt ccg tac gtt gac gtc gtc tcg acc gag aag gag atg att aag<br>Asp Leu Pro Tyr Val Asp Val Val Ser Thr Glu Lys Glu Met Ile Lys<br>                    180                   185                 190 | 576 |
| cgc ttc ctc cgc gtc gtc agg gag aag gac ccc gac gtg ctc atc acc<br>Arg Phe Leu Arg Val Val Arg Glu Lys Asp Pro Asp Val Leu Ile Thr<br>                195                   200                 205 | 624 |
| tac aac ggc gac aac ttc gac ttc gcc tac ctg aag aag cgc tgt gag<br>Tyr Asn Gly Asp Asn Phe Asp Phe Ala Tyr Leu Lys Lys Arg Cys Glu<br>210                      215                     220 | 672 |
| gaa ctc gga ata aag ttc aca ctc ggc agg gac ggg agc gag ccg aag<br>Glu Leu Gly Ile Lys Phe Thr Leu Gly Arg Asp Gly Ser Glu Pro Lys<br>225                      230                     235                 240 | 720 |
| ata cag cga atg ggc gac cgc ttt gcc gtt gag gtg aag ggc agg att<br>Ile Gln Arg Met Gly Asp Arg Phe Ala Val Glu Val Lys Gly Arg Ile<br>                    245                   250                 255 | 768 |
| cac ttc gac ctc tac ccc gtc ata agg cgc acg ata aac ctc ccg acc<br>His Phe Asp Leu Tyr Pro Val Ile Arg Arg Thr Ile Asn Leu Pro Thr<br>                    260                   265                 270 | 816 |
| tac acc ctt gag gcc gtt tac gag gcc gtc ttt gga aag ccc aag gag<br>Tyr Thr Leu Glu Ala Val Tyr Glu Ala Val Phe Gly Lys Pro Lys Glu<br>275                      280                     285 | 864 |
| aag gtt tac gca gag gag ata gcg cag gcc tgg gag agc ggg gag ggc<br>Lys Val Tyr Ala Glu Glu Ile Ala Gln Ala Trp Glu Ser Gly Glu Gly<br>290                      295                     300 | 912 |
| ctt gaa agg gtt gca aga tac tcg atg gag gac gct aag gtg acc tac<br>Leu Glu Arg Val Ala Arg Tyr Ser Met Glu Asp Ala Lys Val Thr Tyr<br>305                      310                     315                 320 | 960 |
| gag ctg gga agg gag ttc ttc ccg atg gag gcc cag ctt tcg agg ctt<br>Glu Leu Gly Arg Glu Phe Phe Pro Met Glu Ala Gln Leu Ser Arg Leu<br>                    325                   330                 335 | 1008 |
| ata ggc cag agc ctc tgg gac gtc tcg cgc tcg agc acc gga aat ttg<br>Ile Gly Gln Ser Leu Trp Asp Val Ser Arg Ser Ser Thr Gly Asn Leu<br>                    340                   345                 350 | 1056 |
| gtg gag tgg ttc ctc ctg cgg aag gcc tac aag agg aac gag ctc gcc | 1104 |

|                 | -continued |
|---|---|

| Val Glu Trp Phe Leu Leu Arg Lys Ala Tyr Lys Arg Asn Glu Leu Ala<br>355                  360                  365 | |

| cca aac aag ccc gac gag agg gag ctc gcg aga cgg cgc ggg ggc tac<br>Pro Asn Lys Pro Asp Glu Arg Glu Leu Ala Arg Arg Arg Gly Gly Tyr<br>370                  375                  380 | 1152 |

| gct ggc ggg tac gtt aag gaa cca gag cgg gga ttg tgg gac aac att<br>Ala Gly Gly Tyr Val Lys Glu Pro Glu Arg Gly Leu Trp Asp Asn Ile<br>385                  390                  395                  400 | 1200 |

| gtg tat cta gac ttc cgc tcg tat gcg tcg tca atc atc ata acc cac<br>Val Tyr Leu Asp Phe Arg Ser Tyr Ala Ser Ser Ile Ile Ile Thr His<br>         405                  410                  415 | 1248 |

| aac gtc tcg ccg gat acc ctc aac cgc gag ggc tgt aaa gag tac gac<br>Asn Val Ser Pro Asp Thr Leu Asn Arg Glu Gly Cys Lys Glu Tyr Asp<br>             420                  425                  430 | 1296 |

| gtc gcc cct gag gtt gga cac aag ttc tgc aag gac ttc ccc ggc ttc<br>Val Ala Pro Glu Val Gly His Lys Phe Cys Lys Asp Phe Pro Gly Phe<br>                 435                  440                  445 | 1344 |

| ata cca agc ctc ctg gga gat ttg ctc gag gag agg cag aag ata aag<br>Ile Pro Ser Leu Leu Gly Asp Leu Leu Glu Glu Arg Gln Lys Ile Lys<br>450                  455                  460 | 1392 |

| cgg aag atg aag gca acg gtt gac ccg ctg gag aag aaa ctc ctc gat<br>Arg Lys Met Lys Ala Thr Val Asp Pro Leu Glu Lys Lys Leu Leu Asp<br>465                  470                  475                  480 | 1440 |

| tac agg cag agg ctg atc aaa atc ctc gcc aac agc ttc tac ggc tac<br>Tyr Arg Gln Arg Leu Ile Lys Ile Leu Ala Asn Ser Phe Tyr Gly Tyr<br>         485                  490                  495 | 1488 |

| tac ggc tac gcc aag gcc cgg tgg tac tgc aag gag tgc gcc gag agc<br>Tyr Gly Tyr Ala Lys Ala Arg Trp Tyr Cys Lys Glu Cys Ala Glu Ser<br>             500                  505                  510 | 1536 |

| gtt acg gcc tgg gga agg gag tat ata gaa atg gtt atc cgg gaa ctc<br>Val Thr Ala Trp Gly Arg Glu Tyr Ile Glu Met Val Ile Arg Glu Leu<br>                 515                  520                  525 | 1584 |

| gaa gaa aaa ttc ggt ttt aaa gtt ctc tat gcc gat aca gac ggt ctc<br>Glu Glu Lys Phe Gly Phe Lys Val Leu Tyr Ala Asp Thr Asp Gly Leu<br>530                  535                  540 | 1632 |

| cat gct acc att ccc gga gca gac gct gaa aca gtc aag aaa aaa gca<br>His Ala Thr Ile Pro Gly Ala Asp Ala Glu Thr Val Lys Lys Lys Ala<br>545                  550                  555                  560 | 1680 |

| aag gag ttc tta aaa tac att aat cca aaa ctg ccc ggc ctg ctc gaa<br>Lys Glu Phe Leu Lys Tyr Ile Asn Pro Lys Leu Pro Gly Leu Leu Glu<br>         565                  570                  575 | 1728 |

| ctt gag tac gag ggc ttc tac gtg agg ggc ttc ttc gtc acg aag aag<br>Leu Glu Tyr Glu Gly Phe Tyr Val Arg Gly Phe Phe Val Thr Lys Lys<br>             580                  585                  590 | 1776 |

| aag tac gct gtg ata gac gag gag ggc aag ata acc acg agg ggt ctt<br>Lys Tyr Ala Val Ile Asp Glu Glu Gly Lys Ile Thr Thr Arg Gly Leu<br>                 595                  600                  605 | 1824 |

| gag att gtg agg cgc gac tgg agc gag ata gcg aag gag acc cag gcc<br>Glu Ile Val Arg Arg Asp Trp Ser Glu Ile Ala Lys Glu Thr Gln Ala<br>610                  615                  620 | 1872 |

| agg gtc tta gag gcg ata ctc aag cac ggt gac gtc gag gag gcc gtt<br>Arg Val Leu Glu Ala Ile Leu Lys His Gly Asp Val Glu Glu Ala Val<br>625                  630                  635                  640 | 1920 |

| agg ata gtc aag gaa gtg acg gaa aag ctg agc aag tat gag gtc ccg<br>Arg Ile Val Lys Glu Val Thr Glu Lys Leu Ser Lys Tyr Glu Val Pro<br>         645                  650                  655 | 1968 |

| ccc gag aag ctg gta atc cac gag cag ata acg cgc gat ttg agg gat<br>Pro Glu Lys Leu Val Ile His Glu Gln Ile Thr Arg Asp Leu Arg Asp<br>             660                  665                  670 | 2016 |

| | | | | | | | | | | | | | | | |
|---|---|---|---|---|---|---|---|---|---|---|---|---|---|---|---|
| tac | aaa | gcc | acc | ggc | ccg | cac | gtt | gcc | gtt | gcg | aag | agg | ctc | gcg | gcg | 2064 |
| Tyr | Lys | Ala | Thr | Gly | Pro | His | Val | Ala | Val | Ala | Lys | Arg | Leu | Ala | Ala | |
| | 675 | | | | 680 | | | | | 685 | | | | | | |
| cgt | gga | gtg | aaa | atc | cgg | ccc | ggc | acg | gtg | ata | agc | tac | atc | gtc | cta | 2112 |
| Arg | Gly | Val | Lys | Ile | Arg | Pro | Gly | Thr | Val | Ile | Ser | Tyr | Ile | Val | Leu | |
| | 690 | | | | 695 | | | | | 700 | | | | | | |
| aag | ggc | tct | gga | agg | ata | ggc | gac | agg | gcg | att | cca | gct | gat | gag | ttc | 2160 |
| Lys | Gly | Ser | Gly | Arg | Ile | Gly | Asp | Arg | Ala | Ile | Pro | Ala | Asp | Glu | Phe | |
| 705 | | | | | 710 | | | | | 715 | | | | | 720 | |
| gac | ccg | acg | aag | cac | cgc | tac | gat | gcg | gaa | tac | tac | atc | gag | aac | cag | 2208 |
| Asp | Pro | Thr | Lys | His | Arg | Tyr | Asp | Ala | Glu | Tyr | Tyr | Ile | Glu | Asn | Gln | |
| | | | 725 | | | | | 730 | | | | | 735 | | | |
| gtt | ctc | ccg | gcg | gtg | gag | agg | att | cta | aaa | gcc | ttc | ggc | tat | cgg | aag | 2256 |
| Val | Leu | Pro | Ala | Val | Glu | Arg | Ile | Leu | Lys | Ala | Phe | Gly | Tyr | Arg | Lys | |
| | | 740 | | | | | 745 | | | | | 750 | | | | |
| gag | gat | ttg | cgc | tac | cag | aag | acg | aag | cag | gtc | ggc | ttg | ggc | gcg | tgg | 2304 |
| Glu | Asp | Leu | Arg | Tyr | Gln | Lys | Thr | Lys | Gln | Val | Gly | Leu | Gly | Ala | Trp | |
| | 755 | | | | | 760 | | | | | 765 | | | | | |
| ctg | aag | gtg | aag | ggg | aag | aag | tga | | | | | | | | | 2328 |
| Leu | Lys | Val | Lys | Gly | Lys | Lys | | | | | | | | | | |
| 770 | | | | | 775 | | | | | | | | | | | |

<210> SEQ ID NO 20
<211> LENGTH: 775
<212> TYPE: PRT
<213> ORGANISM: Artificial sequence
<220> FEATURE:
<223> OTHER INFORMATION: 9oN polymerase variant (exo-) with
    L408Y/Y409A/P410S mutations

<400> SEQUENCE: 20

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
        100                 105                 110

Asp Ile Pro Phe Ala Lys Arg Tyr Leu Ile Asp Lys Gly Leu Ile Pro
    115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
        180                 185                 190

Arg Phe Leu Arg Val Val Arg Glu Lys Asp Pro Asp Val Leu Ile Thr
    195                 200                 205

Tyr Asn Gly Asp Asn Phe Asp Phe Ala Tyr Leu Lys Lys Arg Cys Glu

```
              210                 215                 220
Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
                275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Ala Ser Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640
```

```
Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 21
<211> LENGTH: 2328
<212> TYPE: DNA
<213> ORGANISM: Artificial sequence
<220> FEATURE:
<223> OTHER INFORMATION: 9oN polymerase variant (exo-) with
      L408Y/Y409A/P410V mutations
<220> FEATURE:
<221> NAME/KEY: CDS
<222> LOCATION: (1)..(2328)
<223> OTHER INFORMATION: coding sequence

<400> SEQUENCE: 21 atg att ctc gat acc gac tac atc acc gag aac ggg aag ccc gtg ata      48
Met Ile Leu Asp Thr Asp Tyr Ile Thr Glu Asn Gly Lys Pro Val Ile
1               5                   10                  15 agg gtc ttc aag aag gag aac ggc gag ttt aaa atc gag tac gac aga      96
Arg Val Phe Lys Lys Glu Asn Gly Glu Phe Lys Ile Glu Tyr Asp Arg
                20                  25                  30 acc ttc gag ccc tac ttc tac gcc ctt ctg aag gac gat tct gcg ata     144
Thr Phe Glu Pro Tyr Phe Tyr Ala Leu Leu Lys Asp Asp Ser Ala Ile
            35                  40                  45 gag gac gtc aag aag gta acc gca aag agg cac gga acg gtt gtc aag     192
Glu Asp Val Lys Lys Val Thr Ala Lys Arg His Gly Thr Val Val Lys
        50                  55                  60 gtg aag cgc gcc gag aag gtg cag aag aag ttc ctc ggc agg ccg ata     240
Val Lys Arg Ala Glu Lys Val Gln Lys Lys Phe Leu Gly Arg Pro Ile
65                  70                  75                  80 gag gtc tgg aag ctc tac ttc aac cat cct cag gac gtc ccg gcg att     288
Glu Val Trp Lys Leu Tyr Phe Asn His Pro Gln Asp Val Pro Ala Ile
                85                  90                  95 cga gac agg ata cgc gcc cac ccc gct gtc gtt gac atc tac gag tac     336
Arg Asp Arg Ile Arg Ala His Pro Ala Val Val Asp Ile Tyr Glu Tyr
                100                 105                 110 gac ata ccc ttc gcc aag cgc tac ctc atc gac aag ggc ctg att ccg     384
Asp Ile Pro Phe Ala Lys Arg Tyr Leu Ile Asp Lys Gly Leu Ile Pro
            115                 120                 125 atg gag ggc gac gag gag ctt acg atg ctc gcc ttc gcg atc gca acc     432
Met Glu Gly Asp Glu Glu Leu Thr Met Leu Ala Phe Ala Ile Ala Thr
        130                 135                 140
```

-continued

| | |
|---|---|
| ctc tat cac gag ggc gag gag ttc gga acc ggg ccg att ctc atg ata<br>Leu Tyr His Glu Gly Glu Glu Phe Gly Thr Gly Pro Ile Leu Met Ile<br>145                                  150                             155                           160 | 480 |
| agc tac gcc gac ggg agc gag gcg agg gtg ata acc tgg aag aag att<br>Ser Tyr Ala Asp Gly Ser Glu Ala Arg Val Ile Thr Trp Lys Lys Ile<br>                          165                             170                             175 | 528 |
| gac ctt ccg tac gtt gac gtc gtc tcg acc gag aag gag atg att aag<br>Asp Leu Pro Tyr Val Asp Val Val Ser Thr Glu Lys Glu Met Ile Lys<br>                    180                             185                             190 | 576 |
| cgc ttc ctc cgc gtc gtc agg gag aag gac ccc gac gtg ctc atc acc<br>Arg Phe Leu Arg Val Val Arg Glu Lys Asp Pro Asp Val Leu Ile Thr<br>             195                             200                             205 | 624 |
| tac aac ggc gac aac ttc gac ttc gcc tac ctg aag aag cgc tgt gag<br>Tyr Asn Gly Asp Asn Phe Asp Phe Ala Tyr Leu Lys Lys Arg Cys Glu<br>210                                  215                             220 | 672 |
| gaa ctc gga ata aag ttc aca ctc ggc agg gac ggg agc gag ccg aag<br>Glu Leu Gly Ile Lys Phe Thr Leu Gly Arg Asp Gly Ser Glu Pro Lys<br>225                                230                           235                           240 | 720 |
| ata cag cga atg ggc gac cgc ttt gcc gtt gag gtg aag ggc agg att<br>Ile Gln Arg Met Gly Asp Arg Phe Ala Val Glu Val Lys Gly Arg Ile<br>                          245                             250                             255 | 768 |
| cac ttc gac ctc tac ccc gtc ata agg cgc acg ata aac ctc ccg acc<br>His Phe Asp Leu Tyr Pro Val Ile Arg Arg Thr Ile Asn Leu Pro Thr<br>                    260                             265                             270 | 816 |
| tac acc ctt gag gcc gtt tac gag gcc gtc ttt gga aag ccc aag gag<br>Tyr Thr Leu Glu Ala Val Tyr Glu Ala Val Phe Gly Lys Pro Lys Glu<br>             275                             280                             285 | 864 |
| aag gtt tac gca gag gag ata gcg cag gcc tgg gag agc ggg gag ggc<br>Lys Val Tyr Ala Glu Glu Ile Ala Gln Ala Trp Glu Ser Gly Glu Gly<br>290                                  295                             300 | 912 |
| ctt gaa agg gtt gca aga tac tcg atg gag gac gct aag gtg acc tac<br>Leu Glu Arg Val Ala Arg Tyr Ser Met Glu Asp Ala Lys Val Thr Tyr<br>305                                310                           315                           320 | 960 |
| gag ctg gga agg gag ttc ttc ccg atg gag gcc cag ctt tcg agg ctt<br>Glu Leu Gly Arg Glu Phe Phe Pro Met Glu Ala Gln Leu Ser Arg Leu<br>             325                             330                             335 | 1008 |
| ata ggc cag agc ctc tgg gac gtc tcg cgc tcg agc acc gga aat ttg<br>Ile Gly Gln Ser Leu Trp Asp Val Ser Arg Ser Ser Thr Gly Asn Leu<br>                    340                             345                             350 | 1056 |
| gtg gag tgg ttc ctc ctg cgg aag gcc tac aag agg aac gag ctc gcc<br>Val Glu Trp Phe Leu Leu Arg Lys Ala Tyr Lys Arg Asn Glu Leu Ala<br>             355                             360                             365 | 1104 |
| cca aac aag ccc gac gag agg gag ctc gcg aga cgg cgc ggg ggc tac<br>Pro Asn Lys Pro Asp Glu Arg Glu Leu Ala Arg Arg Arg Gly Gly Tyr<br>370                                  375                             380 | 1152 |
| gct ggc ggg tac gtt aag gaa cca gag cgg gga ttg tgg gac aac att<br>Ala Gly Gly Tyr Val Lys Glu Pro Glu Arg Gly Leu Trp Asp Asn Ile<br>385                                  390                           395                           400 | 1200 |
| gtg tat cta gac ttc cgc tcg tat gcg gtt tca atc atc ata acc cac<br>Val Tyr Leu Asp Phe Arg Ser Tyr Ala Val Ser Ile Ile Ile Thr His<br>                    405                             410                             415 | 1248 |
| aac gtc tcg ccg gat acc ctc aac cgc gag ggc tgt aaa gag tac gac<br>Asn Val Ser Pro Asp Thr Leu Asn Arg Glu Gly Cys Lys Glu Tyr Asp<br>                          420                             425                             430 | 1296 |
| gtc gcc cct gag gtt gga cac aag ttc tgc aag gac ttc ccc ggc ttc<br>Val Ala Pro Glu Val Gly His Lys Phe Cys Lys Asp Phe Pro Gly Phe<br>             435                             440                             445 | 1344 |
| ata cca agc ctc ctg gga gat ttg ctc gag gag agg cag aag ata aag<br>Ile Pro Ser Leu Leu Gly Asp Leu Leu Glu Glu Arg Gln Lys Ile Lys<br>450                                  455                           460 | 1392 |

|  |  |
|---|---|
| cgg aag atg aag gca acg gtt gac ccg ctg gag aag aaa ctc ctc gat<br>Arg Lys Met Lys Ala Thr Val Asp Pro Leu Glu Lys Lys Leu Leu Asp<br>465                    470                    475                    480 | 1440 |
| tac agg cag agg ctg atc aaa atc ctc gcc aac agc ttc tac ggc tac<br>Tyr Arg Gln Arg Leu Ile Lys Ile Leu Ala Asn Ser Phe Tyr Gly Tyr<br>                    485                    490                    495 | 1488 |
| tac ggc tac gcc aag gcc cgg tgg tac tgc aag gag tgc gcc gag agc<br>Tyr Gly Tyr Ala Lys Ala Arg Trp Tyr Cys Lys Glu Cys Ala Glu Ser<br>                500                    505                    510 | 1536 |
| gtt acg gcc tgg gga agg gag tat ata gaa atg gtt atc cgg gaa ctc<br>Val Thr Ala Trp Gly Arg Glu Tyr Ile Glu Met Val Ile Arg Glu Leu<br>515                    520                    525 | 1584 |
| gaa gaa aaa ttc ggt ttt aaa gtt ctc tat gcc gat aca gac ggt ctc<br>Glu Glu Lys Phe Gly Phe Lys Val Leu Tyr Ala Asp Thr Asp Gly Leu<br>                    530                    535                    540 | 1632 |
| cat gct acc att ccc gga gca gac gct gaa aca gtc aag aaa aaa gca<br>His Ala Thr Ile Pro Gly Ala Asp Ala Glu Thr Val Lys Lys Lys Ala<br>545                    550                    555                    560 | 1680 |
| aag gag ttc tta aaa tac att aat cca aaa ctg ccc ggc ctg ctc gaa<br>Lys Glu Phe Leu Lys Tyr Ile Asn Pro Lys Leu Pro Gly Leu Leu Glu<br>                    565                    570                    575 | 1728 |
| ctt gag tac gag ggc ttc tac gtg agg ggc ttc ttc gtc acg aag aag<br>Leu Glu Tyr Glu Gly Phe Tyr Val Arg Gly Phe Phe Val Thr Lys Lys<br>                    580                    585                    590 | 1776 |
| aag tac gct gtg ata gac gag gag ggc aag ata acc acg agg ggt ctt<br>Lys Tyr Ala Val Ile Asp Glu Glu Gly Lys Ile Thr Thr Arg Gly Leu<br>                    595                    600                    605 | 1824 |
| gag att gtg agg cgc gac tgg agc gag ata gcg aag gag acc cag gcc<br>Glu Ile Val Arg Arg Asp Trp Ser Glu Ile Ala Lys Glu Thr Gln Ala<br>610                    615                    620 | 1872 |
| agg gtc tta gag gcg ata ctc aag cac ggt gac gtc gag gag gcc gtt<br>Arg Val Leu Glu Ala Ile Leu Lys His Gly Asp Val Glu Glu Ala Val<br>625                    630                    635                    640 | 1920 |
| agg ata gtc aag gaa gtg acg gaa aag ctg agc aag tat gag gtc ccg<br>Arg Ile Val Lys Glu Val Thr Glu Lys Leu Ser Lys Tyr Glu Val Pro<br>                    645                    650                    655 | 1968 |
| ccc gag aag ctg gta atc cac gag cag ata acg cgc gat ttg agg gat<br>Pro Glu Lys Leu Val Ile His Glu Gln Ile Thr Arg Asp Leu Arg Asp<br>                    660                    665                    670 | 2016 |
| tac aaa gcc acc ggc ccg cac gtt gcc gtt gcg aag agg ctc gcg gcg<br>Tyr Lys Ala Thr Gly Pro His Val Ala Val Ala Lys Arg Leu Ala Ala<br>                    675                    680                    685 | 2064 |
| cgt gga gtg aaa atc cgg ccc ggc acg gtg ata agc tac atc gtc cta<br>Arg Gly Val Lys Ile Arg Pro Gly Thr Val Ile Ser Tyr Ile Val Leu<br>690                    695                    700 | 2112 |
| aag ggc tct gga agg ata ggc gac agg gcg att cca gct gat gag ttc<br>Lys Gly Ser Gly Arg Ile Gly Asp Arg Ala Ile Pro Ala Asp Glu Phe<br>705                    710                    715                    720 | 2160 |
| gac ccg acg aag cac cgc tac gat gcg gaa tac tac atc gag aac cag<br>Asp Pro Thr Lys His Arg Tyr Asp Ala Glu Tyr Tyr Ile Glu Asn Gln<br>                    725                    730                    735 | 2208 |
| gtt ctc ccg gcg gtg gag agg att cta aaa gcc ttc ggc tat cgg aag<br>Val Leu Pro Ala Val Glu Arg Ile Leu Lys Ala Phe Gly Tyr Arg Lys<br>                    740                    745                    750 | 2256 |
| gag gat ttg cgc tac cag aag acg aag cag gtc ggc ttg ggc gcg tgg<br>Glu Asp Leu Arg Tyr Gln Lys Thr Lys Gln Val Gly Leu Gly Ala Trp<br>                    755                    760                    765 | 2304 |
| ctg aag gtg aag ggg aag aag tga<br>Leu Lys Val Lys Gly Lys Lys | 2328 |

<210> SEQ ID NO 22
<211> LENGTH: 775
<212> TYPE: PRT
<213> ORGANISM: Artificial sequence
<220> FEATURE:
<223> OTHER INFORMATION: 9oN polymerase variant (exo-) with L408Y/Y409A/P410V mutations

<400> SEQUENCE: 22

| | | | | | | | | | | | | | | |
|---|---|---|---|---|---|---|---|---|---|---|---|---|---|---|
| Met | Ile | Leu | Asp | Thr | Asp | Tyr | Ile | Thr | Glu | Asn | Gly | Lys | Pro | Val | Ile |
| 1 | | | | 5 | | | | | 10 | | | | | 15 | |
| Arg | Val | Phe | Lys | Lys | Glu | Asn | Gly | Glu | Phe | Lys | Ile | Glu | Tyr | Asp | Arg |
| | | | 20 | | | | | 25 | | | | | 30 | | |
| Thr | Phe | Glu | Pro | Tyr | Phe | Tyr | Ala | Leu | Leu | Lys | Asp | Asp | Ser | Ala | Ile |
| | | | 35 | | | | | 40 | | | | | 45 | | |
| Glu | Asp | Val | Lys | Lys | Val | Thr | Ala | Lys | Arg | His | Gly | Thr | Val | Val | Lys |
| | 50 | | | | | 55 | | | | | 60 | | | | |
| Val | Lys | Arg | Ala | Glu | Lys | Val | Gln | Lys | Lys | Phe | Leu | Gly | Arg | Pro | Ile |
| 65 | | | | | 70 | | | | | 75 | | | | | 80 |
| Glu | Val | Trp | Lys | Leu | Tyr | Phe | Asn | His | Pro | Gln | Asp | Val | Pro | Ala | Ile |
| | | | | 85 | | | | | 90 | | | | | 95 | |
| Arg | Asp | Arg | Ile | Arg | Ala | His | Pro | Ala | Val | Val | Asp | Ile | Tyr | Glu | Tyr |
| | | | 100 | | | | | 105 | | | | | 110 | | |
| Asp | Ile | Pro | Phe | Ala | Lys | Arg | Tyr | Leu | Ile | Asp | Lys | Gly | Leu | Ile | Pro |
| | | | 115 | | | | | 120 | | | | | 125 | | |
| Met | Glu | Gly | Asp | Glu | Glu | Leu | Thr | Met | Leu | Ala | Phe | Ala | Ile | Ala | Thr |
| | 130 | | | | | 135 | | | | | 140 | | | | |
| Leu | Tyr | His | Glu | Gly | Glu | Glu | Phe | Gly | Thr | Gly | Pro | Ile | Leu | Met | Ile |
| 145 | | | | | 150 | | | | | 155 | | | | | 160 |
| Ser | Tyr | Ala | Asp | Gly | Ser | Glu | Ala | Arg | Val | Ile | Thr | Trp | Lys | Lys | Ile |
| | | | | 165 | | | | | 170 | | | | | 175 | |
| Asp | Leu | Pro | Tyr | Val | Asp | Val | Val | Ser | Thr | Glu | Lys | Glu | Met | Ile | Lys |
| | | | 180 | | | | | 185 | | | | | 190 | | |
| Arg | Phe | Leu | Arg | Val | Val | Arg | Glu | Lys | Asp | Pro | Asp | Val | Leu | Ile | Thr |
| | | | 195 | | | | | 200 | | | | | 205 | | |
| Tyr | Asn | Gly | Asp | Asn | Phe | Asp | Phe | Ala | Tyr | Leu | Lys | Lys | Arg | Cys | Glu |
| | 210 | | | | | 215 | | | | | 220 | | | | |
| Glu | Leu | Gly | Ile | Lys | Phe | Thr | Leu | Gly | Arg | Asp | Gly | Ser | Glu | Pro | Lys |
| 225 | | | | | 230 | | | | | 235 | | | | | 240 |
| Ile | Gln | Arg | Met | Gly | Asp | Arg | Phe | Ala | Val | Glu | Val | Lys | Gly | Arg | Ile |
| | | | | 245 | | | | | 250 | | | | | 255 | |
| His | Phe | Asp | Leu | Tyr | Pro | Val | Ile | Arg | Arg | Thr | Ile | Asn | Leu | Pro | Thr |
| | | | 260 | | | | | 265 | | | | | 270 | | |
| Tyr | Thr | Leu | Glu | Ala | Val | Tyr | Glu | Ala | Val | Phe | Gly | Lys | Pro | Lys | Glu |
| | | | 275 | | | | | 280 | | | | | 285 | | |
| Lys | Val | Tyr | Ala | Glu | Glu | Ile | Ala | Gln | Ala | Trp | Glu | Ser | Gly | Glu | Gly |
| | 290 | | | | | 295 | | | | | 300 | | | | |
| Leu | Glu | Arg | Val | Ala | Arg | Tyr | Ser | Met | Glu | Asp | Ala | Lys | Val | Thr | Tyr |
| 305 | | | | | 310 | | | | | 315 | | | | | 320 |
| Glu | Leu | Gly | Arg | Glu | Phe | Phe | Pro | Met | Glu | Ala | Gln | Leu | Ser | Arg | Leu |
| | | | | 325 | | | | | 330 | | | | | 335 | |
| Ile | Gly | Gln | Ser | Leu | Trp | Asp | Val | Ser | Arg | Ser | Ser | Thr | Gly | Asn | Leu |
| | | | 340 | | | | | 345 | | | | | 350 | | |

```
Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Tyr Ala Val Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
```

<210> SEQ ID NO 23
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 23
gacttccgct cggttgcgtt g                                              21

<210> SEQ ID NO 24
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 24
aagcccctca cgtagaagcc                                                20

<210> SEQ ID NO 25
<211> LENGTH: 51
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (22)..(22)
<223> OTHER INFORMATION: "n" represents g, a, t or c
<220> FEATURE:
<221> NAME/KEY: misc_feature
<222> LOCATION: (23)..(23)
<223> OTHER INFORMATION: "n" represents g, a, t or c
<220> FEATURE:
<221> NAME/KEY: misc_feature
<222> LOCATION: (24)..(24)
<223> OTHER INFORMATION: k is g or t/u
<220> FEATURE:
<221> NAME/KEY: misc_feature
<222> LOCATION: (25)..(25)
<223> OTHER INFORMATION: "n" represents g, a, t or c
<220> FEATURE:
<221> NAME/KEY: misc_feature
<222> LOCATION: (26)..(26)
<223> OTHER INFORMATION: "n" represents g, a, t or c
<220> FEATURE:
<221> NAME/KEY: misc_feature
<222> LOCATION: (27)..(27)
<223> OTHER INFORMATION: k is g or t/u
<220> FEATURE:
<221> NAME/KEY: misc_feature
<222> LOCATION: (28)..(28)
<223> OTHER INFORMATION: "n" represents g, a, t or c
<220> FEATURE:
<221> NAME/KEY: misc_feature
<222> LOCATION: (29)..(29)
<223> OTHER INFORMATION: "n" represents g, a, t or c
<220> FEATURE:
<221> NAME/KEY: misc_feature
<222> LOCATION: (30)..(30)
<223> OTHER INFORMATION: k is g or t/u

<400> SEQUENCE: 25
gtgtatctag acttccgctc gnnknnknnk tcaatcatca taacccacaa c             51

<210> SEQ ID NO 26
<211> LENGTH: 46
<212> TYPE: DNA
<213> ORGANISM: Artificial sequence

```
<220> FEATURE:
<223> OTHER INFORMATION: Oligonucleotide primer

<400> SEQUENCE: 26
gttagcagcc ggatcctcac ttcttcccct tcaccttcag ccacgc                46

<210> SEQ ID NO 27
<211> LENGTH: 43
<212> TYPE: DNA
<213> ORGANISM: Artificial sequence
<220> FEATURE:
<223> OTHER INFORMATION: Oligonucleotide primer

<400> SEQUENCE: 27
gggacaacat tgtgtatcta gacttccgct cgctggtgcc ttc                   43

<210> SEQ ID NO 28
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 28
gtctatcaca gcgtacttct tcttcg                                      26

<210> SEQ ID NO 29
<211> LENGTH: 43
<212> TYPE: DNA
<213> ORGANISM: Artificial sequence
<220> FEATURE:
<223> OTHER INFORMATION: Oligonucleotide primer

<400> SEQUENCE: 29
gaaggcacca gcgagcggaa gtctagatac acaatgttgt ccc                   43

<210> SEQ ID NO 30
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 30
ggccagagcc tctgggacgt c                                           21

<210> SEQ ID NO 31
<211> LENGTH: 51
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (12)..(12)
<223> OTHER INFORMATION: m is a or c
<220> FEATURE:
<221> NAME/KEY: misc_feature
<222> LOCATION: (13)..(13)
<223> OTHER INFORMATION: "n" represents g, a, t or c
<220> FEATURE:
<221> NAME/KEY: misc_feature
<222> LOCATION: (14)..(14)
<223> OTHER INFORMATION: "n" represents g, a, t or c
<220> FEATURE:
<221> NAME/KEY: misc_feature
<222> LOCATION: (18)..(18)
<223> OTHER INFORMATION: m is a or c
<220> FEATURE:
```

<221> NAME/KEY: misc_feature
<222> LOCATION: (19)..(19)
<223> OTHER INFORMATION: "n" represents g, a, t or c
<220> FEATURE:
<221> NAME/KEY: misc_feature
<222> LOCATION: (20)..(20)
<223> OTHER INFORMATION: "n" represents g, a, t or c
<220> FEATURE:
<221> NAME/KEY: misc_feature
<222> LOCATION: (21)..(21)
<223> OTHER INFORMATION: m is a or c
<220> FEATURE:
<221> NAME/KEY: misc_feature
<222> LOCATION: (22)..(22)
<223> OTHER INFORMATION: "n" represents g, a, t or c
<220> FEATURE:
<221> NAME/KEY: misc_feature
<222> LOCATION: (23)..(23)
<223> OTHER INFORMATION: "n" represents g, a, t or c

<400> SEQUENCE: 31
gcgtagccgt amnngccmnn mnngctgttg gcgaggattt tgatcagcct c         51

<210> SEQ ID NO 32
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 32
gcgcgcggat cctcacttct tccccttcac c                               31

<210> SEQ ID NO 33
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 33
gatgattgac ggcgccagcg agcggaag                                   28

<210> SEQ ID NO 34
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 34
cttccgctcg ctggcgccgt caatcatc                                   28

<210> SEQ ID NO 35
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 35
gatgattgaa gggcccagcg agcggaag                                   28

<210> SEQ ID NO 36
<211> LENGTH: 28

```
<212> TYPE: DNA
<213> ORGANISM: Artificial sequence
<220> FEATURE:
<223> OTHER INFORMATION: Oligonucleotide primer

<400> SEQUENCE: 36
cttccgctcg ctgggccctt caatcatc                                          28
```

MODIFIED POLYMERASES FOR IMPROVED INCORPORATION OF NUCLEOTIDE ANALOGUES

The present application is a continuation of U.S. patent application Ser. No. 14/476,387, filed Sep. 3, 2014, which is a continuation of U.S. patent application Ser. No. 13/856,556, filed Apr. 4, 2013, now U.S. Pat. No. 8,852,910, issued Oct. 7, 2014, which is a continuation of U.S. patent application Ser. No. 10/571,706, filed Mar. 13, 2006, now U.S. Pat. No. 8,460,910, issued Jun. 11, 2013, which is a U.S. National Phase of International Application No. PCT/GB04/03891, filed Sep. 10, 2004, designating the U.S. and published on Mar. 17, 2005 as WO 2005/024010, which claims priority to Great Britain Application Serial No. 0321306.3, filed Sep. 11, 2003. The content of these applications are incorporated herein by reference in their entireties.

FIELD OF THE INVENTION

The present invention relates to polymerase enzymes and more particularly modified DNA polymerases which give improved incorporation of modified nucleotides compared to a control polymerase. Also included in the present invention are methods of using the polymerases for DNA sequencing, including use of high density arrays.

BACKGROUND

DNA polymerases are relied upon by all organisms to replicate and maintain their genomes. They allow high fidelity replication of DNA by detecting complementarity between bases as well as recognising additional structural features of the base.

Three main super families of DNA polymerase exist, based upon their amino acid similarity to *E. Coli* DNA polymerases I, II and III. They are called Family A, B and C polymerases respectively. Whilst crystallographic analysis of Family A and B polymerases reveals a common structural core for the nucleotide binding site, sequence motifs that are well conserved within families are only weakly conserved between families, and there are significant differences in the way these polymerases discriminate between nucleotide analogues.

Early experiments with DNA polymerases revealed difficulties incorporating modified nucleotides such as dideoxynucleotides (ddNTPs). There are, therefore, several examples in which DNA polymerases have been modified to increase the rates of incorporation of nucleotide analogues. The majority of these have focused on variants of Family A polymerases (eg. Taq) with the aim of increasing the incorporation of dideoxynucleotide chain terminators.

For example Tabor, S. and Richardson, C. C. (1995) Proc. Natl. Acad. Sci (USA) 92:6339 describe the replacement of phenylalanine 667 with tyrosine in *T. aquaticus* DNA polymerase and the effects this has on discrimination of dideoxynucleotides by the DNA polymerase.

In order to increase the efficiency of incorporation of modified nucleotides, DNA polymerases have been utilised or engineered such that they lack 3'-5' exonuclease activity (designated exo−). The exo− variant of 9° N polymerase is described by Perler et al., 1998 U.S. Pat. No. 5,756,334 and by Southworth et al., 1996 Proc. Natl Acad. Sci USA 93:5281.

Gardner A. F. and Jack W. E. (Determinants of nucleotide sugar recognition in an archaeon DNA polymerase Nucl. Acids Res. 27:2545, 1999) describe mutations in Vent DNA polymerase that enhance the incorporation of ribo-, 2' and 3' deoxyribo- and 2'3'-dideoxy-ribonucleotides. The two individual mutations in Vent polymerase, Y412V and A488L, enhanced the relative activity of the enzyme with the nucleotide ATP. In addition, other substitutions at Y412 and A488 also increased ribonucleotide incorporation, though to a lesser degree. It was concluded that the bulk of the amino acid side chain at residue 412 acts as a "steric gate" to block access of the 2'-hydroxyl of the ribonucleotide sugar to the binding site. However, the rate enhancement with cordycepin (3' deoxy adenosine triphosphate) was only 2-fold, suggesting that the Y412V polymerase variant was also sensitive to the loss of the 3' sugar hydroxyl. For residue A488, the change in activity is less easily rationalized. A488 is predicted to point away from the nucleotide binding site; here the enhancement in activity was explained through a change to the activation energy required for the enzymatic reaction. These mutations in Vent correspond to Y409 and A485 in 9° N polymerase.

The universality of the A488L mutation has been confirmed by homologous mutations in the following hyperthermophilic polymerases:

1) A486Y variant of Pfu DNA polymerase (Evans et al., 2000. Nucl. Acids. Res. 28:1059). A series of random mutations was introduced into the polymerase gene and variants were identified that had improved incorporation of ddNTPs. The A486Y mutation improved the ratio of ddNTP/dNTP in sequencing ladders by 150-fold compared to wild type. However, mutation of Y410 to A or F produced a variant that resulted in an inferior sequencing ladder compared to the wild type enzyme. For further information reference is made to International Publication No. WO 01/38546.

2) A485L variant of 9° N DNA polymerase (Gardner and Jack, 2002. Nucl. Acids Res. 30:605). This study demonstrated that the mutation of Alanine to Leucine at amino acid 485 enhanced the incorporation of nucleotide analogues that lack a 3' sugar hydroxyl moiety (acyNTPs and dideoxyNTPs).

3) A485T variant of Tsp JDF-3 DNA polymerase (Arezi et al., 2002. J. Mol. Biol. 322:719). In this paper, random mutations were introduced into the JDF-3 polymerase from which variants were identified that had enhanced incorporation of ddNTPs. Individually, two mutations, A485T and P410L, improved ddNTP uptake compared to the wild type enzyme. In combination, these mutations had an additive effect and improved ddNTP incorporation by 250-fold. This paper demonstrates that the simultaneous mutation of two regions of a DNA polymerase can have additive affects on nucleotide analogue incorporation. In addition, this report demonstrates that P410, which lies adjacent to Y409 described above, also plays a role in the discrimination of nucleotide sugar analogues.

4) WO 01/23411 describes the use of the A488L variant of Vent in the incorporation of dideoxynucleotides and acyclonucleotides into DNA. The application also covers methods of sequencing that employ these nucleotide analogues and variants of 9° N DNA polymerase that are mutated at residue 485.

Sagner et al. (1991 Rapid filter assay for the detection of DNA polymerase activity: direct identification of the gene for the DNA polymerase from *Thermus aquaticus*. Gene 97:119) discloses a method for identifying novel DNA polymerases.

As is clear from the above discussion, polymerases have been modified to incorporate nucleotides lacking the hydroxyl group at the 3 carbon of the ribose or deoxyribose sugar moiety. However, the inventors have now surprisingly found that incorporation of a modified nucleotide having a 3° substituent which is larger that the natural 3' hydroxyl group can be achieved by modified DNA polymerases.

DESCRIPTION OF THE INVENTION

The present inventors have devised a method for sequencing DNA that uses nucleotide analogues bearing modifications at the 3' sugar hydroxyl group which block incorporation of further nucleotides. The use of nucleotides bearing a 3' block allows successive nucleotides to be incorporated into a polynucleotide chain in a controlled manner. After each nucleotide addition the presence of the 3° block prevents incorporation of a further nucleotide into the chain. Once the nature of the incorporated nucleotide has been determined, the block may be removed, leaving a free 3° hydroxyl group for addition of the next nucleotide.

To improve the efficiency of this DNA sequencing method, the inventors have investigated whether DNA polymerases could be modified to produce improved rates of incorporation of such 3° substituted nucleotide analogues.

Other groups, as discussed above, have identified polymerase variants that are sensitive to changes to the 3' sugar hydroxyl moiety that is found naturally on dNTPs. However, these enzymes were characterised by their discrimination of dNTPs over ddNTPs that lack the hydroxyl group at the 3' position. The present invention differs from these because in the previous studies the ribose ring of the "modified" ddNTPs was smaller than the dNTP. In contrast, the nucleotide analogues which are utilised in the inventors' sequencing method have 3' substituents which are larger in size than the naturally-occurring 3'-hydroxyl. Thus, previous studies have addressed a different problem to the present invention and the differences in the nature of the desired substrate molecule for the polymerase means that the previous studies cannot be extrapolated to the problem addressed by the present invention. It is, therefore, difficult to predict which polymerase sequences would improve incorporation of the 3' modified nucleotide analogues utilised in the present invention into DNA.

There remains a requirement for altered DNA polymerases which can incorporate efficiently nucleotides which are modified at the 3' sugar hydroxyl such that the substituent is larger in size than the naturally occurring 3' hydroxyl group. For many nucleotides, modification of the 3' sugar hydroxyl group results in substrates that terminate DNA synthesis. However, there also exist nucleotides that bear modifications at the 3' sugar position that, under appropriate conditions, can be reacted to form a 3' hydroxyl group. These nucleotides are referred to as 'reversible terminators'. DNA polymerases that have the ability to incorporate such 3' blocked nucleotides have applications that involve DNA synthesis, such as DNA sequencing. Furthermore, the altered DNA polymerases must be able to retain base specificity for the modified nucleotides, even though efficiency of incorporation is increased. In particular, certain cofactors such as Manganese ions, have been shown to increase nucleotide misincorporation by DNA polymerases; however, for certain applications, such as DNA sequencing, it is important that reaction conditions are chosen that allow the fidelitous incorporation of modified nucleotides. In these cases, it would be preferable to not include Manganese or other cofactors that increase misincorporation into the reaction mixtures.

The present inventors have now surprisingly identified certain altered polymerases which exhibit improved incorporation of the desired analogues and have a number of other associated advantages. The surprising features and major advantages of the polymerases of the invention are summarised as follows:

(1) Ability to Incorporate Nucleotides Having Large 3' Substituent Moieties.

This represents a key advantage of the polymerases of the invention and is directly related to utility in sequencing protocols based on the use of 3'-blocked nucleotides. As outlined above, previous studies on incorporation of modified nucleotides have focussed on the ability of modified polymerases to incorporate nucleotides lacking a hydroxyl group at the 3' position. It is most surprising, therefore, that the inventors have been able to prepare altered polymerases that are capable of incorporating modified nucleotides having 3' substituent moieties that are substantially larger in size than the natural 3' hydroxyl. The sheer size of the substituents that can be incorporated relative to the size of the natural hydroxyl group and the range of different chemical moieties than can be incorporated is most unexpected.

(2) Minimal Variation in Primary Amino Acid Sequence.

The inventors have shown that the ability to incorporate the modified nucleotides can be conferred by as little as one amino acid change in the nucleotide binding site of the enzyme. It is extremely surprising that such a profound effect on the substrate specificity of the enzyme can be achieved at all, but it is even more unexpected that such an effect can be achieved with such a limited change in primary amino acid sequence.

(3) Ability to Incorporate all Four Natural DNA Bases.

The inventors have still further observed that the altered polymerases are capable of incorporating modified nucleotides containing all four natural DNA bases A, T, C and G. This again is an unexpected finding, as one skilled in the art might reasonably expect that different modified polymerases would have to be engineered to incorporate analogues containing different bases. This in turn would mean that a cocktail of different polymerases, possibly requiring different reaction conditions for optimal activity, would be needed in order to perform a sequencing reaction. The surprising finding that altered polymerases can be constructed such that a single enzyme is capable of incorporating modified nucleotide analogues containing each of the four natural DNA bases therefore provides a huge advantage in sequencing protocols, not least because all four bases can be incorporated under the same reaction conditions.

(4) Substantial Increase in Rates of Incorporation.

The sheer increase in rates of incorporation of the modified analogues that have been achieved with polymerases of the invention is also profoundly unexpected, particularly since such improvements can be achieved with such limited changes in primary amino acid sequence. As illustrated in the accompanying examples, the most preferred altered polymerases exhibit a time to 50% product conversion on the first cycle of enzymology of 20 seconds or less, and a corresponding activity on the second cycle of 1.5 min or less, whilst control enzymes exhibit no detectable incorporation on the first or second cycle of enzymology under the same reaction conditions.

(5) Activity at Low Temperatures.

Altered polymerases of the invention also exhibit activity over a wide temperature range, and more specifically exhibit activity at low temperatures far removed from the temperature optimum of the equivalent wild type enzymes. As illustrated in the accompanying examples, the inventors have shown that altered polymerases are active at temperatures as low as 45°, and even as low as 30° C., which is far removed from the temperature optimum of 80° C. for the 9° N polymerase. Thus, altered polymerases are suitable for use in sequencing protocols carried out at low and high temperatures. This finding is again extremely unexpected, since one might reasonably expect that in order to observe an acceptable rate of incorporation of modified nucleotide analogues it would be necessary to work at conditions close to the optimum for activity of the wild-type enzyme, e.g. a temperature of 80° C. for the 9° N polymerase.

(6) Activity at Low Substrate Concentration.

Still further, the inventors have observed that the concentration of modified nucleotide analogue substrate required to achieve incorporation using altered polymerases of the invention is much lower than had been anticipated. One skilled in the art might have expected that a high concentration of modified nucleotide would be required in order to achieve incorporation, effectively to "force" the enzyme to incorporate the modified nucleotide. The ability to use lower concentrations of substrate is important as it leads to reduced non-specific binding as well as being more economical.

(7) Activity Over Multiple Cycles of Incorporation.

Altered polymerase enzymes exhibit improved incorporation of the modified nucleotides over multiple enzyme cycles. This property is again important for sequencing-by-synthesis applications requiring sequential incorporation of nucleotides into a polynucleotide chain. An enzyme that can incorporate modified nucleotides in one cycle of enzymology only would be of limited value in sequencing because different polymerases would need to be added at different cycles.

It is contemplated that modified polymerases that have been identified for the incorporation of nucleotides that bear large 3' substituents would also be capable of incorporating natural nucleotides and other nucleotide analogues.

In summary, the inventors have produced altered polymerases which are capable of incorporating modified nucleotides bearing large 3' substituents and which exhibit a number of advantageous properties.

Accordingly, in a first aspect of the invention there is provided an altered polymerase enzyme which is capable of improved incorporation of nucleotides which have been modified at the 3' sugar hydroxyl such that the substituent is larger in size than the naturally occurring 3' hydroxyl group, compared to a control polymerase enzyme.

"Incorporation" means joining of the modified nucleotide to the free 3' hydroxyl group of a second nucleotide via formation of a phosphodiester linkage with the 5° phosphate group of the modified nucleotide. The second nucleotide to which the modified nucleotide is joined will typically occur at the 3' end of a polynucleotide chain.

Unless otherwise stated, the terms "modified nucleotides" and "nucleotide analogues" when used in the context of this invention refer to nucleotides which have been modified at the 3' sugar hydroxyl such that the substituent is larger in size than the naturally occurring 3' hydroxyl group. These terms may be used interchangeably.

The term "large 3 substituent(s)" refers to a substituent group at the 3' sugar hydroxyl which is larger in size than the naturally occurring 3' hydroxyl group.

"Improved" incorporation is defined herein to include an increase in the efficiency and/or observed rate of incorporation of at least one modified nucleotide, compared to a control polymerase enzyme. However, the invention is not limited just to improvements in absolute rate of incorporation of the modified nucleotides. As summarised above, the altered polymerases exhibit other desirable properties related to the incorporation of nucleotide analogues and the term "improved incorporation" is to be interpreted accordingly as also encompassing improvements in any of these other properties, with or without an increase in the rate of incorporation.

When considering sequential incorporation of nucleotide analogues, for example in a sequencing reaction, the improvement in the efficiency and/or observed rate of incorporation may be manifest on any cycle of enzymology, but may occur on two or more cycles, and most preferably on all cycles. The "improvement" need not be constant over all cycles.

The altered polymerase may exhibit improvement in the efficiency and/or observed rate of incorporation for one type of modified nucleotide or for a range of different modified nucleotides. For example, the polymerase may be capable of incorporating a series of modified nucleotides which have the same 3' substituent but which differ in some other portion of the nucleotide molecule, such as the base portion or the presence of a detectable label. Other polymerases may be capable of incorporating a range of modified nucleotides which carry different 3' substituents.

Improvements in the efficiency and/or rate of incorporation achieved with the altered polymerase relative to a control polymerase may be determined by comparing the ability of the two polymerases to incorporate the same modified nucleotide(s) in a suitable assay system. Moreover, the ability of the altered polymerase to incorporate modified nucleotide(s) may also be defined by reference to an absolute measure of incorporation in a specified assay system. One such assay system, given by way of example, is the gel-based incorporation assay described in the accompanying Example 2. Preferred polymerases exhibiting the ability to incorporate modified nucleotides are those which show detectable (i.e. above background) product conversion on a cycle of enzymology at for 15 minutes at 45° C., 50 mM Tris, pH8, 4 mM $MgSO_4$, 0.05 (v/v) Tween, 50 µg/ml enzyme, and 2 µM 3' modified nucleotide in the assay system of Example 2. In preferred embodiments the polymerase may exhibit a time to 50% product conversion on the second cycle of enzymology at 45° C., 50 mM Tris, pH8, 4 mM $MgSO_4$, 0.05 (v/v) Tween, 50 g/ml enzyme, and 2 µM 3' modified nucleotide of 19.5 min or less, more preferably 5 min or less and most preferably 1.5 min or less. For the most preferred polymerases product conversion on the first cycle will be less than 1 minute under these conditions, as described in Example 2.

The enhanced ability of the altered polymerase to incorporate modified nucleotides may also be determined by measurement of incorporation rates at different nucleotide concentrations. Altered polymerases exhibiting the desired "improved activity" will preferably exhibit a greater than 10% nucleotide incorporation at a concentration of 25 µM.

As aforesaid, although improvement in the rate of incorporation of modified nucleotides is an important aspect of the invention, the invention is not limited to solely to altered polymerases that show improvements in enzyme kinetics. In fact, the invention also encompasses altered polymerase enzymes which exhibit other "improvements" in incorporation of modified nucleotides which are of practical and economic benefit.

In a further embodiment, the "improvement" exhibited by the altered polymerase may be the ability to incorporate modified nucleotides containing each of the natural DNA bases A, T, C and G. The ability to incorporate all four bases with a single enzyme is of great practical and economic value in sequencing protocols. Even if absolute rates of incorporation were comparable between, for example, four different enzymes each having specificity for modified nucleotides containing a different base A, T, C or G, and a single enzyme capable of incorporating nucleotides containing each of the four bases, there would be considerable practical advantages in the use of a single enzyme capable of incorporating all four bases. Use of single enzyme avoids any problems in providing optimum reaction conditions for different polymerases.

In a further embodiment, the "improvement" may be the ability to incorporate the modified nucleotides at low temperatures and/or over a wider temperature range than the control enzyme. The altered polymerases of the invention are capable of incorporating modified nucleotides at a temperature of 45° C., and even as low as 30° C. Preferred polymerases are those which exhibit detectable incorporation of the modified nucleotides at a temperature of 30° C. and/or at a temperature of 45° C.

In practice, the enzyme will exhibit detectable incorporation of the modified nucleotide over a range of temperatures above and/or below 30° C. or 45° C. The polymerase may exhibit detectable incorporation activity across the whole range of temperatures from 30° C. or 45° C. up to the optimum temperature for activity of the equivalent wild-type (or exo−) enzyme, which could be as high as 80° C. for enzymes derived from thermophilic species. Preferred polymerases may exhibit detectable incorporation activity across the whole range of temperatures from 30° C. to 37° C. or from 30° C. to 45° C. and/or from 65° C. to 80° C. The rate of incorporation may not be constant over the full range of temperature over which the enzyme exhibits detectable incorporation activity and incorporation rate need not be maximal at 30° C. or 45° C. Even if the absolute rate of incorporation of a given modified nucleotide were comparable between, for example, the altered polymerase working at low temperature (e.g. 30° C. or 45° C.) and wild type polymerase working close to the natural optimum temperature for enzyme activity (e.g. 80° C. for 9° N polymerase) it would still be of great practical benefit to be able to work at the lower temperature because it reduces the requirement for other components in the sequencing system to be tolerant to the high temperature conditions. However, in other situations where the components of the sequencing reactions are tolerant to these elevated temperatures, there may advantages to performing incorporations at higher temperatures for accurate DNA synthesis through regions of secondary structure in the DNA template. Thus, the ability of a DNA polymerase to have a wide range of operating temperatures provides utility for different sequencing applications.

In a still further embodiment, the "improvement" may be the ability to incorporate the modified nucleotides when using a lower concentration of the modified nucleotides as substrate. Preferably the altered polymerase should exhibit detectable incorporation of the modified nucleotide when working at a substrate concentration in the micromolar range. Preferred polymerases may exhibit detectable incorporation of the modified nucleotide when working at a substrate concentration in the range of from 0.2 µM to 50 µM, and more preferably at a substrate concentration of 25 µM. However, the polymerases of the invention may exhibit detectable incorporation of the modified nucleotide when working at substrate concentrations below 0.2 µM (and/or in excess of 50 µM). Certain polymerases according to the invention exhibit detectable incorporation of the modified nucleotide when working at substrate concentrations as low as 50 nM.

Even if the rate of incorporation of the modified analogues were to be comparable between the altered polymerase and control polymerase, if the altered polymerase requires a substantially lower concentration of the substrate then this will be of great economic benefit, since modified nucleotides are expensive to manufacture, and if the enzyme reactions occur on a surface, then the lower concentration of reagents would be expected to reduce non-specific binding.

For the avoidance of doubt, it is hereby stated that altered polymerases that exhibit a substantially equivalent rate of incorporation of modified nucleotides when compared to a control enzyme, but that nevertheless exhibit improvements in any one or more of the other desirable properties listed above (i.e. fidelity, ability to incorporate all bases, activity at low temperature/wide temperature range, low substrate concentration, etc) compared to the same control enzyme are to be included within the scope of the invention.

By "altered polymerase enzyme" it is meant that the polymerase has at least one amino acid change compared to the control polymerase enzyme. In general this change will comprise the substitution of at least one amino acid for another. In certain instances these changes will be conservative changes, to maintain the overall charge distribution of the protein. However, the invention is not limited to only conservative substitutions. Non-conservative substitutions are also envisaged in the present invention. Moreover, it is within the contemplation of the present invention that the modification in the polymerase sequence may be a deletion or addition of one or more amino acids from or to the protein, provided that the polymerase has improved activity with respect to the incorporation of nucleotides modified at the 3' sugar hydroxyl such that the substituent is larger in size than the naturally occurring 3' hydroxyl group as compared to a control polymerase enzyme.

"Nucleotide" is defined herein to include both nucleotides and nucleosides. Nucleosides, as for nucleotides, comprise a purine or pyrimidine base linked glycosidically to ribose or deoxyribose, but they lack the phosphate residues which would make them a nucleotide. Synthetic and naturally occurring nucleotides, prior to their modification at the 3' sugar hydroxyl, are included within the definition.

The altered polymerase will generally be an "isolated" or "purified" polypeptide. By "isolated polypeptide" is meant a polypeptide that is essentially free from contaminating cellular components, such as carbohydrates, lipids, nucleic acids or other proteinaceous impurities which may be associated with the polypeptide in nature. Typically, a preparation of the isolated polymerase contains the polymerase in a highly purified form, i.e. at least about 80% pure, preferably at least about 90% pure, more preferably at least about 95% pure, more preferably at least about 98% pure and most preferably at least about 99% pure. Purity of a preparation of the enzyme may be assessed, for example, by appearance of a single band on a standard SDS-polyacrylamide gel electrophoresis.

The altered polymerase may be a "recombinant" polypeptide.

The altered polymerase according to the invention may be a family B type DNA polymerase, or a mutant or variant thereof. Family B DNA polymerases include numerous archael DNA polymerase, human DNA polymerase α and T4, RB69 and φ29 phage DNA polymerases. These polymerases are less well studied than the family A polymerases, which include polymerases such as Taq, and T7 DNA polymerase. In one embodiment the polymerase is selected from any family B archael DNA polymerase, human DNA polymerase α or T4, RB69 and φ29 phage DNA polymerases.

The archael DNA polymerases are in many cases from hyperthermophilic archea, which means that the polymerases are often thermostable. Accordingly, in a further preferred embodiment the polymerase is selected from Vent, Deep Vent, 9° N and Pfu polymerase. Vent and Deep Vent are commercial names used for family B DNA polymerases isolated from the hyperthermophilic archaeon *Thermococcus litoralis*. 9° N polymerase was also identified from *Thermococcus* sp. Pfu polymerase was isolated from *Pyrococcus furiosus*. The most preferred polymerase in the present invention is 9° N polymerase, including mutants and variants thereof.

It is to be understood that the invention is not intended to be limited to mutants or variants of the family B polymerases. The altered polymerase may also be a family A polymerase, or a mutant or variant thereof, for example a mutant or variant Taq or T7 DNA polymerase enzyme, or a polymerase not belonging to either family A or family B, such as for example reverse transcriptases.

"Control polymerase" is defined herein as the polymerase against which the activity of the altered polymerase is compared. In one embodiment of the invention the control polymerase may comprise a wild type polymerase or an exo– variant thereof. Unless otherwise stated, by "wild type" it is generally meant that the polymerase comprises its natural amino acid sequence, as it would be found in nature.

However the invention is not limited to merely a comparison of activity of the altered polymerase against the wild type equivalent or exo– variant of the polymerase that is being altered. Many polymerases exist whose amino acid sequence have been modified (e.g. by amino acid substitution mutations) and which can prove a suitable control for use in, assessing the modified nucleotide incorporation efficiencies of the improved polymerases provided by the present invention. The control polymerase can, therefore, comprise any known polymerase, including mutant polymerases known in the art. The (in)activity the chosen "control" polymerase with respect to incorporation of the desired nucleotide analogues may be determined by an incorporation assay. Preferred control polymerases are those which exhibit no detectable incorporation of modified nucleotides in the incorporation assay described in Example 2.

A number of suitable control polymerases having one or more amino acid substitution mutations relative to the sequence of a wild-type (or exo– variant) base polymerase are summarised below

TABLE I examples of control polymerases

| Base polymerase (WT or exo–) | Additional mutations functionally equivalent to amino acid sequence of the base polymerase |
|---|---|
| Vent ™ | Y412V, Y412L, Y412F, Q486E, Q486L, R487K, A488C, A488S, A488L, A488I, A488F, A488V, K490A, K490K, K490N, N494D, S495A, Y496F, Y496L, Y497S, Y497F, Y499L, Y499F, A488C/Y499F or A488L/Y499L. |
| 9°N | A485L or Y409V/A485L (latter is utilised in the present examples) |
| Pfu | A486Y |
| Tsp JDF-3 | A485T, P410L or A485T/P410L |

The control polymerase may comprises any one of the listed substitution mutations functionally equivalent to the amino acid sequence of the given base polymerase (or an exo-variant thereof). Thus, the control' polymerase may be a mutant version of the listed base polymerase having one of the stated mutations or combinations of mutations, and preferably having amino acid sequence identical to that of the base polymerase (or an exo– variant thereof) other than at the mutations recited above. Alternatively, the control polymerase may be a homologous mutant version of a polymerase other than the stated base polymerase, which includes a functionally equivalent or homologous mutation (or combination of mutations) to those recited in relation to the amino acid sequence of the base polymerase. By way of illustration, the control polymerase could be a mutant version of the Vent™ polymerase having one of the mutations or combinations of mutations listed above relative to the Vent amino acid sequence, or it could be a mutant version of another polymerase, for example a mutant 9° N polymerase, incorporating a mutation (or mutations) functionally equivalent to a mutation (or mutations) listed by reference to the Vent™ amino acid sequence.

By "functionally equivalent" it is meant that the control polymerase, in the case of studies using a different polymerase entirely, will contain the amino acid substitution that is considered to occur at the amino acid position in the other polymerase that has the same functional role in the enzyme. As an example, the mutation at position 412 from Tyrosine to Valine (Y412V) in the Vent DNA polymerase would be functionally equivalent to a substitution at position 409 from Tyrosine to Valine (Y409V) in the 9° N polymerase. The bulk of this amino acid residue is thought to act as a "steric gate" to block access of the 2'-hydroxyl of the nucleotide sugar to the binding site. Also, residue 488 in Vent polymerase is deemed equivalent to amino acid 485 in 9° N polymerase, such that the Alanine to Leucine mutation at 488 in Vent (A488L) is deemed equivalent to the A485L mutation in 9° N polymerase. This residue is thought to play a role in changing the activation energy required for the enzymatic reaction.

Generally functionally equivalent substitution mutations in two or more different polymerases occur at homologous amino acid positions in the amino acid sequences of the polymerases. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues in the amino acid sequences of two or more different polymerases on the basis of sequence alignment and/or molecular modelling.

It should be noted that throughout the specification mutations within the amino acid sequence of a polymerase are written in form:
 (i) Single letter amino acid as found in wild type polymerase.
 (ii) Position of the change in the amino acid sequence of the polymerase.
 (iii) Single letter amino acid as found in the altered polymerase.

So, mutation of a Tyrosine residue in the wild type polymerase to a Valine residue in the altered polymerase at position 409 of the amino acid sequence would be written as Y409V.

Functionally equivalent, positionally equivalent and homologous amino acids within the wild type amino acid sequences of two different polymerases do not necessarily have to be the same type of amino acid residue, although functionally equivalent, positionally equivalent and homologous amino acids are commonly conserved. By way of example, the motif A region of 9° N polymerase has the sequence LYP, the functionally homologous region of Vent™ polymerase also has sequence LYP. In the case of these two polymerases the homologous amino acid sequences are identical, however homologous regions in other polymerases may have different amino acid sequence. When referring to functionally equivalent, positionally equivalent and homologous mutations, the mutant amino acid will generally be the same type of amino acid residue in each of the mutant polymerases, for example mutation Y409A in 9° N polymerase is functionally equivalent or homologous to mutation Y412A in Vent™ polymerase.

Preferred Altered Polymerase Proteins

The inventors have surprisingly determined that amino acid sequence variation in a particular three amino-acid region of the nucleotide binding site referred to herein as the "motif A region" has a profound effect on the ability of polymerases to incorporate nucleotide analogues having a substituent at the 3° position which is larger than a hydroxyl group.

In the context of this application, the term "motif A region" specifically refers to the three amino acids functionally equivalent or homologous to amino acids 408-410 in 9° N polymerase. The terms "motif A region" and "region A" are used interchangeably throughout and refer to the defined three amino acid region of the polymerase protein rather than to any particular amino acid sequence.

The term "motif B region" specifically refers to the three amino acids functionally equivalent or homologous to amino acids 484-486 in 9° N polymerase.

The terms "motif A" and motif B" have been used in the art in order to refer to regions of sequence homology in the nucleotide binding sites of family B and other polymerases. However, in the context of this application these terms are used to refer only to the specific amino acid regions recited above.

Functionally equivalent or homologous "motif A regions" and "motif B regions" of polymerases other than 9° N can be identified on the basis of amino acid sequence alignment and/or molecular modelling. Sequence alignments may be compiled using any of the standard alignment tools known in the art, such as for example BLAST etc.

By way of example, the functionally equivalent "motif A regions" and "motif B regions" of several polymerases are indicated, as follows:

| Polymerase | "Motif A region" | "Motif B region" |
|---|---|---|
| 9°N | 408-410 | 484-486 |
| Vent ™ | 411-413 | 487-489 |
| Pfu | 409-411 | 485-487 |
| RB69 | 415-417 | |
| JDF-3 | 408-410 | 484-486 |
| Taq | 614-616 | |

The above list is intended to be illustrative of the invention and should not be construed as limiting the invention to these particular polymerases. Functionally equivalent "motif A regions" and "motif B regions" are also present in further non-family B polymerases, including the family A polymerases, reverse transcriptase etc.

Mutation of the motif A region alone, in the absence of any other sequence variation elsewhere in the enzyme, is sufficient to substantially improve the ability of the polymerase to incorporate nucleotide analogues having a substituent at the 3 position which is larger than a hydroxyl group.

Even more surprisingly, it has been determined that a substitution mutation of a single amino acid in the motif A region of a polymerase can be sufficient to improve the ability of the polymerase to incorporate nucleotides which have been modified at the 3' sugar hydroxyl such that the substituent is larger in size than the naturally occurring 3' hydroxyl group. Substitution mutations in two or all three of the amino acids in the motif A region can also improve the ability of a polymerase to incorporate the desired analogues.

Accordingly, the preferred altered polymerases according to the invention are mutant polymerases comprising one, two or three amino acid substitution mutations in the three-amino acid region of the polymerase referred to herein as the "motif A region". The substitution mutation(s) may lead to the incorporation of any known natural or synthetic amino acid, subject to the following provisos:

(1) When the polymerase is a mutant Vent™ polymerase, mutants having the single amino acid substitutions Y412V, Y412L or Y412F are excluded from the scope of the invention. These substitutions may be present in Vent™ mutants having further mutations, such as for example variants having two or three substitution mutations in the motif A region within the scope of the invention, but must not be present singly, i.e. in a mutant having wild type Vent™ sequence other than at this single amino acid substitution.

(2) When the polymerase is a mutant 9° N polymerase, mutants having the amino acid substitution Y409V in combination with the amino acid substitution A485L are excluded from the scope of the invention. The Y409V substitution may, however, be present in the absence of the A485L mutation within the scope of the invention, for example Y409V may be present singly or may be present in 9° N mutants having two or three substitution mutations in the motif A region.

(3) When the polymerase is a mutant Tsp JDF-3 polymerase, mutants having a single amino acid substitution P410L, either alone or in combination with the further mutation A485T, are excluded from the scope of the invention. However, the P410L mutation may, for example, be present in Tsp JDF-3 mutants having two or three substitution mutations in the motif A region within the scope of the invention.

The specific polymerases recited under provisos (1), (2) and (3) are excluded from the invention. It is preferred that the altered polymerase is not a different type of polymerase bearing functionally equivalent or homologous amino acid changes to the polymerases recited under provisos (1), (2) and (3), although such homologous polymerases are not excluded.

As illustrated in the accompanying examples, the inventors have determined that variation of the amino acid sequence in the motif A region alone can result in improvements in the desired activity of the polymerase, substantially improving the rate of incorporation of nucleotide analogues having large substituents at the 3' position. Moreover, the inventors have determined consensus sequence preferences for the three amino acids making up the motif A region.

Therefore, in preferred embodiments:

The first amino acid of the motif A region is preferably selected from:
  aromatic amino acids, particularly tyrosine (Y) or phenylalanine (F), amino acids with aliphatic side chains, particularly isoleucine (I), alanine (A) or valine (V), or glutamate (Q), cysteine (C) or serine (S).

By "first amino acid of the motif A region" is meant the amino acid functionally equivalent or homologous to amino acid residue 408 of the 9° N polymerase.

By "second amino acid of the motif A region" is meant the amino acid functionally equivalent or homologous to amino acid residue 409 of the 9° N polymerase.

The second amino acid of the motif A region is preferably selected from alanine (A), serine (S) or glycine (G), most preferably alanine (A).

When the polymerase contains only a single amino acid substitution in the motif A region at the second amino acid position, this amino acid is preferably not valine (V), leucine (L) or phenylalanine (F). However, substitution to valine (V), leucine (L) or phenylalanine (F) may be present in combination with further substitutions at the first and/or third amino acid positions in the motif A region.

By "third amino acid of the motif A region" is meant the amino acid functionally equivalent or homologous to amino acid residue 410 of the 9° N polymerase.

The third amino acid of the motif A region is preferably selected from:
  serine (S), alanine (A) or glycine (G),
  Amino acids having beta-branched side chains, particularly isoleucine (I), threonine (T), valine (V) or leucine (L).

It is also desirable to include the wild type amino acid proline at the third amino acid position, but only in the presence of amino acid substitutions at one or both of the first and second amino acid positions in region A.

In altered polymerases having one amino acid substitution mutation only in the motif A region, the substitution may be present at the first, second or third amino acid position of the motif A region, subject to the provisos given above. However, it is preferred for the single amino acid substitution to be present at the second amino acid position, this being the amino acid functionally equivalent or homologous to amino acid residue 409 of the 9° N polymerase.

In embodiments having a single substitution mutation in the motif A region, the mutant amino acid will preferably be selected according to the amino acid preferences recited above for the first, second and third amino acids of the motif A region. Particularly preferred polymerases having a single substitution mutation in the motif A region are those wherein the second amino acid residue of the motif A region is mutated to alanine (A). Therefore, preferred mutant polymerase include, but are not limited to, 9° N polymerase having the mutation Y409A, Vent™ polymerase having the mutation Y412A, Pfu polymerase having the mutation Y410A, JDF-3 polymerase having the mutation Y409A, and Taq polymerase having the mutation E615A.

For the avoidance of doubt, polymerases having a single amino acid substitution mutation in the motif A region may include further substitution mutations compared to wild type in regions of the enzyme outside of the motif A region within the scope of the invention.

In altered polymerases having two amino acid substitution mutations in the motif A region, the mutations may be present in any combination, i.e. the first and second amino acids may be mutant, or the first and third amino acids may be mutant, or the second and third amino acids may be mutant. It is generally preferred for the first and second amino acids of the motif A region to be mutant, with the third amino acid being wild-type.

In embodiments having two substitution mutations in the motif A region, the mutant amino acids will again preferably be selected according to the amino acid preferences recited above for the first, second and third amino acids of the motif A region. All possible combinations of two of the amino acid preferences given above for the first, second and third amino acids are envisaged within the scope of the invention. However, particularly preferred polymerases having two substitution mutations are those wherein the first amino acid residue of the motif A region is mutated to valine (V), phenylalanine (F) or tyrosine (Y), the second amino acid residue of the motif A region is mutated to alanine (A) and the third amino acid residue of the motif A region is wild type. Therefore, preferred mutant polymerase include, but are not limited to, 9° N polymerase having one of double mutations L408F/Y409A, L408V/Y409A or L408Y/Y409A, Vent™ polymerase having one of double mutations L411Y/Y412A, L411V/Y412A or L411F/Y412A, Pfu polymerase having one of double mutations L409Y/Y410A, L409V/Y410A or L409F/Y410A, JDF-3 polymerase having one of double mutations L408F/Y409A, L408Y/Y409A or L408V/Y409A, and Taq polymerase having one of double mutations I614F/E615A, I709V/E710A or I614Y/E615A.

Again for the avoidance of doubt it is stated that polymerases having two amino acid substitution mutations in the motif A region may include further substitution mutations compared to wild type in regions of the enzyme outside of the motif A region within the scope of the invention.

Altered polymerases according to the invention may also include three amino acid substitution mutations in the motif A region. In embodiments having three substitution mutations in the motif A region, the mutant amino acids will again preferably be selected according to the amino acid preferences recited above for the first, second and third amino acids of the motif A region. All possible combinations of three of the amino acid preferences given above for the first, second and third amino acids are envisaged within the scope of the invention. However, in the most preferred embodiments of the invention the motif A region of the polymerase may have one of the following mutant amino acid sequences:

```
YST, FAI, AAA, YAS, YAV, YGI, YSG, SGG, CST, IAL,
CGG, SAL, SAA, CAA, YAA, QAS, VSS, VAG, VAV, FAV,
AGI, YSS, AAT, FSS
or
VAL.
```

As further demonstrated in the experimental section, modified DNA polymerases incorporating these region A sequences show substantially improved incorporation of nucleotides which have been modified at the 3 sugar hydroxyl such that the substituent is larger in size than the naturally occurring 3' hydroxyl group, compared to the 9° N double mutant. The most effective mutants are those having the region A sequences YAV and YAS. Therefore, preferred polymerases according to the invention are those having amino acid sequence YAV or YAS in the motif A region. Most preferred mutant polymerase include, but are not limited to, 9° N polymerase having one of the triple mutations L408Y/Y409A/P410S or L408Y/Y409A/P410V, Vent™ polymerase having one of the triple mutations L411Y/Y412A/P413V or L411Y/Y412A/P413S, Pfu polymerase having one of the triple mutations L409Y/Y410A/P411V or L409Y/Y410A/P411S, JDF-3 polymerase having one of the triple mutations L408Y/Y409A/P410V or L408Y/Y409A/P410S, and Taq polymerase having one of the triple mutations I614Y/E615A/L616V or I614Y/E615A/L616S.

Again for the avoidance of doubt it is stated that polymerases having three amino acid substitution mutations in the motif A region may include further substitution mutations compared to wild type in regions of the enzyme outside of the motif A region within the scope of the invention.

In certain embodiments, the polymerases exhibiting one, two or three amino acid substitution mutations in the motif A region may additionally comprise one, two or three substitution mutations in the motif B region. It has been shown that certain region B mutations, in combination with region A mutations, can still further enhance the activity of the polymerase.

The polymerase may include a single amino acid substitution at the first, second or third amino acid residue of the motif B region, or may include any combination of two or more mutations or may be mutated at all three residues in region B. For any given polymerase, the first amino acid of the motif B region is defined as the amino acid functionally equivalent or homologous to residue 484 of the 9° N polymerase amino acid sequence, the second amino acid of the motif B region is defined as the amino acid functionally equivalent or homologous to residue 485 of the 9° N polymerase amino acid sequence and the third amino acid of the motif B region is defined as the amino acid functionally equivalent or homologous to residue 486 of the 9° N polymerase amino acid sequence Preferred altered polymerases according to the invention may include substitution mutations at the second amino acid of the motif B region, this being the amino acid functionally equivalent or homologous to residue 485 of the 9° N polymerase amino acid sequence, in addition to sequence variation in the motif A region. Mutation of this residue (or its functional equivalent or homologue in polymerases other than 9° N) has generally been observed to enhance overall polymerase activity. Hence, inclusion of a mutation at this position, in combination with region A variation, may produce still further enhancement of activity compared to region A variation alone. The following substitutions are preferred: A485L, A485F, A485I, A485S, A485V and A485C, with A485L being the most preferred.

The substitution mutation at the second amino acid of the motif B region (functionally equivalent or homologous to residue 485 of the 9° N polymerase amino acid sequence) may be present singly (meaning in the absence of any other mutation in the motif B region) or may be present with one or two further substitutions in the motif B region.

In polymerases having two substitution mutations in the motif B region, in addition to mutation in the motif A region, the mutations may occur in any combination, i.e. first and second, first and third or second and third residues mutated. However, it is preferred for the first and third residues to be mutated in combination. Particularly preferred combinations are mutation to glycine at the first amino acid position of the motif B region, in combination with mutation to leucine at the third amino acid position, or mutation to asparagine at the first amino acid position of the motif B region in combination with mutation to glutamine at the third amino acid position.

In altered polymerases having three amino acid substitutions in the motif B region, in addition to mutation in the motif A region, suitable mutant amino acid sequences for the motif B region include, but are not limited to, the following: SKN, GRD, KEN, ISN and THH.

The altered polymerase of the invention may include any of the region A mutations or combinations of mutations recited herein either in the absence of any region B mutation or in combination with any of the specific region B mutations or combinations of mutations described herein.

The invention encompasses altered polymerases comprising at least one mutation in each of the motif A and motif B regions, wherein the total number of mutations is greater than two. In particular, the invention encompasses, although is not limited to, polymerases having two or three mutations in the motif A region with one mutation in the motif B region.

Particularly preferred polymerases according to the invention are 9° N polymerases having one of the following motif A region sequences: FAP, VAP, YST, FAI, AAA, YAS, YAV, YGI, YSG, SGG, CST, IAL, CGG, SAL, SAA, CAA, YAA, QAS, VSS, VAG, VAV, FAV, AGI, YSS, AAT, FSS or VAL, most preferably YAV or YAS, plus a substitution mutation at position 485 in region B, most preferably A485L. However, it is to be understood that the invention also encompasses polymerases other than 9° N, such as for example Vent™ polymerases, Pfu polymerases, JDF-3 polymerases, Taq polymerases etc. including homologous amino acid substitutions (list is illustrative, not limiting).

The preferred 9° N polymerases recited in the preceding paragraph all exhibit surprisingly improved incorporation of nucleotide analogues which have been modified at the 3' sugar hydroxyl such that the substituent is larger in size than the naturally occurring 3 hydroxyl group compared to the 9° N polymerase double mutant (9° N DM, having mutations Y409V/A485L) control polymerase, as illustrated in the accompanying examples. Polymerases including the motif A region sequences YAV or YAS exhibited the best incorporation rate for the desired analogues of those polymerases tested under the conditions of the Example.

Therefore, the invention also relates to a 9° N polymerase molecule comprising the amino acid sequence shown as SEQ ID NO: 20 and a 9° N polymerase molecule comprising the amino sequence shown as SEQ ID NO: 22. SEQ ID NO: 20 represents the complete amino acid sequence of the 9° N polymerase YAS mutant tested in the experimental section (also includes mutation A485L), whereas SEQ ID NO: 22 represents the complete amino acid sequence of the 9° N polymerase YAV mutant (also including mutation A485L). The invention also encompasses polymerases having amino acid sequences which differ from those shown as SEQ ID NOs: 20 and 22 only in amino acid changes which do not affect the function of the polymerase to a material extent. In this case the relevant function of the polymerase is defined as an improved ability, as compared to the control protein, to incorporate modified nucleotides having a substituent at the 3' sugar hydroxyl which is larger in size than the naturally occurring 3' hydroxyl group. Thus conservative substitutions at residues which are not important for this activity of the YAV or YAS polymerase variants would be included within the scope of the invention. The effect of further mutations on the function of the enzyme may be readily tested, for example using the incorporation assay described in the accompanying examples.

The invention also relates to a 9° N polymerase molecule comprising the amino acid sequence shown as SEQ ID NO: 18. SEQ ID NO: 18 represents the complete amino acid sequence of the 9° N polymerase "ED" mutant tested in the experimental section, which includes the motif A region sequence VAL in addition to the A485L mutation in the motif B region. This polymerase variant exhibits improved incorporation of the 3' modified nucleotide analogues having substituents larger than the hydroxyl group as compared to the 9° N polymerase double mutant (Y409V/A485L).

In certain embodiments of the invention the polymerase variant may comprise three amino acid substitution mutations in the motif A region and two or three amino acid substitution mutations in the motif B region. Examples of suitable polymerase variants have been discovered by introducing mutations simultaneously at the motif A region and the motif B region in the 9° N polymerase. A library of polymerase variants was screened for the incorporation of the 3' modified nucleotide analogues. Variants that displayed enhanced levels of incorporation compared to the parental clone were purified and tested to confirm their activity.

Accordingly, the invention also provides, but is not limited to, an altered polymerase which comprises any one of the following sets of substitution mutations functionally equivalent or homologous to the 9° N DNA polymerase amino acid sequence:
L408W/Y409A/P410L R484S/A485K/I486N
L408D/Y409V/P410G R484G/A485R/I486D
L408M/Y409L/P410F R484K A485H/I486N
L408V/Y409D/P410G R484G/ /I486L
L408V/Y409A/P410L R4841/A485S/I486N
L408S/Y409S/P410L R484N/ /I486Q
L408Y/Y409A/P410L R484T/A485H/I486H As is shown in the experimental section, all of these specific mutant DNA polymerases show improved incorporation of nucleotides which have been modified at the 3' sugar hydroxyl such that the substituent is larger in size than the naturally occurring 3 hydroxyl group, compared to a control polymerase enzyme. The control polymerase can be the wild type 9° N polymerase or alternatively a substituted polymerase, such as the Y409V/A485L double mutant 9° N polymerase (9DM).

One preferred altered polymerase of the seven specific region A and region B variants listed above in the experiments was the L408V/Y409A/P410L R4841/A485S/I486N 9° N mutant (referred to as 2E). This polymerase variant exhibits improved incorporation of the 3' modified nucleotide analogues having substituents larger than the hydroxyl group as compared to the 9° N polymerase double mutant (Y409V/A485L).

Therefore, the invention also relates to a 9° N polymerase molecule comprising the amino sequence as shown in SEQ ID NO: 12. This SEQ ID NO: 12 represents the amino acid sequence of the 2E protein. The invention also encompasses polymerases having amino acid sequences which differ from that shown as SEQ ID NO: 12 only in amino acid changes which do not affect the function of the polymerase to a material extent. In this case the relevant function would be the improved ability, as compared to the control protein, of the polymerase to incorporate modified nucleotides. Thus conservative substitutions at residues which are not important for this activity of the 2E polymerase would be included within the scope of the invention.

In a still further aspect the invention provides a 9° N polymerase comprising the amino acid sequence as set out in SEQ ID NO: 14 (sequence of 9° N polymerase lacking exonuclease activity) with one or more changes in the amino acid sequence between residues 408 and 410 and optionally between residues 484 and 486, excluding changes which would result in a protein with a valine residue at amino acid 409 and a leucine residue at amino acid 485, or a protein with a leucine residue at amino acid 485, in the absence of any other changes in the amino acid sequence between residues 408 and 410 or between residues 484 and 486.

The amino acid changes introduced into SEQ ID No: 14 must be such that they do not only alter residue 409 to valine and residue 485 to leucine or alter amino acid 485 to leucine. These changes can occur, but the must not occur together (double mutant) or singly (leucine at position 485) in isolation from a further change in the amino acid sequence of the 9° N polymerase. A single amino acid change can be sufficient to improve functionality of 9° N in terms of incorporation of modified nucleotides. The change in the amino acid sequence may incorporate any known natural or synthetic amino acid. In a preferred embodiment of these aspects of the invention the altered 9° N polymerases will catalyse improved incorporation of nucleotides which have been modified at the 3° sugar hydroxyl such that the substituent is larger in size than the naturally occurring hydroxyl group.

Preferred embodiments of all of the above-described polymerase variants having mutations in the motif A region alone or in combination with mutations in the motif B region have wild-type sequence in the motif C region of the nucleotide binding site. The "motif C region" is defined herein as the amino acid residues functionally equivalent or homologous to residues 493, 494 and 496 of the 9° N polymerase amino acid sequence. However, it is to be understood that variants having one or more amino acid changes in this region in addition to changes in the motif A region, with or without changes in the motif B region, are not excluded. In particular, variants having conservative amino acid changes in the motif C region are included within the scope of the invention.

It will be appreciated that in addition to the amino acid substitutions in the motif A region, and optionally the motif B region, described above, the altered polymerases of the invention may include further changes in amino acid sequence, as compared to the equivalent wild-type protein. Further amino acid substitutions, deletions, additions, fusions etc. may be incorporated, for example in order to introduce a desirable property into the enzyme and/or to improve recombinant expression and/or to facilitate purification of the protein and/or in order to remove an undesirable property of the enzyme. The altered polymerases may also incorporate amino acid changes which, in themselves, do not have a significant or detectable effect on polymerase activity and which do not alter any other function of the polymerase or confer any desirable property. These may include, for example, conservative amino acid substitutions in regions of the protein outside of the motif A region and motif B region.

By way of example, in a preferred embodiment of the invention the altered polymerase enzyme of the invention may be further altered such that it lacks 3'-5' exonuclease activity. This 3'-5' exonuclease activity is absent in certain DNA polymerases such as Taq DNA polymerase. It is useful to remove this exonuclease proof-reading activity when using modified nucleotides to prevent the exonuclease removing the non-natural nucleotide after incorporation. Such changes to DNA polymerase enzymes is therefore of benefit for DNA sequencing applications involving 3' modified nucleotides. Archael DNA polymerases can be genetically modified within the conserved exonuclease motif, changing the amino acid sequence from DIE to AIA, in order to remove 3'-5' activity. Such changes have previously been made for the Vent and Deep Vent DNA polymerases (New England Biolabs; see Nucleic Acids, Research 1999, Vol. 27, No. 12 and Nucleic Acids Research, 2002, Vol. 30, No. 2).

In the 9° N polymerase exonuclease activity may be removed by including the substitution mutations D141A and E143A.

Nucleic Acids Encoding Altered Polymerases

The invention further relates to nucleic acid molecules encoding the altered polymerase enzymes of the invention.

For any given altered polymerase which is a mutant version of a polymerase for which the amino acid sequence and preferably also the wild type nucleotide sequence encoding the polymerase is known, it is possible to obtain a nucleotide sequence encoding the mutant according to the basic principles of molecular biology. For example, given that the wild type nucleotide sequence encoding 9° N polymerase is known, it is possible to deduce a nucleotide sequence encoding any given mutant version of 9° N having one or more amino acid substitutions using the standard genetic code. Similarly, nucleotide sequences can readily be derived for mutant versions other polymerases such as, for example, Vent™, Pfu, Tsp JDF-3, Taq, etc. Nucleic acid molecules having the required nucleotide sequence may then be constructed using standard molecular biology techniques known in the art.

In one particular embodiment the invention relates to nucleic acid molecules encoding mutant versions of the 9° N polymerase. Therefore, the invention provides a nucleic acid molecule comprising the nucleotide sequence shown as SEQ ID NO: 13 but having one or more changes in the nucleic acid sequence in the region from nucleotide 1222 to nucleotide 1230 (inclusive of these nucleotides), wherein said nucleic acid molecule encodes a mutant 9° N polymerase enzyme having one, two or three amino acid substitution mutations in the region from amino acid residue 408 to amino acid residue 410, with the proviso that the nucleic acid molecule does not encode a mutant 9° N polymerase having the amino acid substitution mutations Y409V and A485L in combination.

The nucleotide sequence may optionally further include one or more changes in the region from nucleotide 1449 to nucleotide 1457 (inclusive of these residues) as compared to the sequence shown as SEQ ID NO:13, such that the Mutant 9° N polymerase enzyme polymerase enzyme further includes one, two or three amino acid substitution mutations in the region from amino acid residue 484 to residue 486.

Changes in the nucleic acid sequence shown as SEQ ID NO 13 according to this aspect of the invention must be such that they alter the amino acid sequence of the polymerase. Changes in the nucleic acid sequence that are silent with respect to the overall amino acid sequence of the 9° N polymerase are not included in this aspect of the invention. The change of amino acid residue 409 to valine and residue 485 to leucine, or the change of amino acid 485 to a leucine residue should not be the only changes that are made to the polymerase. These changes can occur, but they must not occur together (double mutant) in the absence of any further change in the amino acid sequence of the 9° N polymerase other then the exo– mutations D141A and E143A.

In certain preferred embodiments, the invention provides a nucleic acid molecule encoding a mutant 9° N polymerase, the nucleic acid molecule comprising one of the following the nucleotide sequences:

SEQ ID NO: 19 (encoding the YAS mutant described in the experimental section),
SEQ ID NO: 21 (encoding the YAV mutant described in the experimental section),
SEQ ID NO: 17 (encoding the ED mutant described in the experimental section),
or
SEQ ID NO: 11 (encoding the 2E mutant described in the experimental section).

In accordance with the present invention, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the polymerase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbour Laboratory.

Such an expression vector includes a vector having a nucleic acid according to the invention operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the invention.

The nucleic acid molecule may encode a mature protein or a protein having a prosequence, including that encoding a leader sequence on the preprotein which is then cleaved by the host cell to form a mature protein.

The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the polymerase by higher eukaryotes may be optimised by including an enhancer sequence in the vector. Enhancers are cis-acting elements of DNA that act on a promoter to increase the level of transcription. Vectors will also generally include origins of replication in addition to the selectable markers.

Nature of the "Modified Nucleotide"

As aforementioned, the polymerases of the present invention are selected according their ability to catalyse improved incorporation of nucleotides which have been modified at the 3' sugar hydroxyl such that the substituent is larger in size than the naturally occurring 3' hydroxyl group, compared to a control polymerase.

The preferred nucleotides that will be incorporated more efficiently by the polymerases of the present invention are exemplified by a purine or pyrimidine base and a ribose or deoxyribose sugar moiety having a removable 3'-OH blocking group covalently attached thereto, such that the 3° carbon atom has attached a group of the structure

—O—Z wherein Z is any of —C(R')$_2$—O—R", —C(R')—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' May be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3' OH;

with the proviso that where Z is —C(R')$_2$—S—R", both R' groups are not H.

The nucleosides or nucleotides which are incorporated by the polymerases of the present invention comprise a purine or pyrimidine base and a ribose or deoxyribose sugar moiety which has a blocking group covalently attached thereto, preferably at the 3' O position, which renders the molecules useful in techniques requiring blocking of the 3-OH group to prevent incorporation of additional nucleotides, such as for example in sequencing reactions, polynucleotide synthesis, nucleic acid amplification, nucleic acid hybridisation assays, single nucleotide polymorphism studies, and other such techniques.

Once the blocking group has been removed, it is possible to incorporate another nucleotide to the free 3'-OH group.

Preferred modified nucleotides are exemplified in International Patent Application publication number WO 2004/018497 in the name of Solexa Limited, which reference is incorporated herein in its entirety.

In a preferred embodiment the R group of the modified nucleotide or nucleoside is an alkyl or substituted alkyl. In a further embodiment the group of the modified nucleotide or nucleoside is of formula —C(R')$_2$—N$_3$. In a most preferred embodiment the modified nucleotide or nucleoside includes a Z group which is an azido methyl group.

The preferred polymerases of the invention having the motif A region sequences YAV or YAS (most preferably mutant 9° N polymerases having this motif A sequence in combination with the A485L mutation) are particularly preferred for incorporation of nucleotide analogues wherein Z is an azido methyl group.

The modified nucleotide can be linked via the base to a detectable label by a desirable linker, which label may be a fluorophore, for example. The detectable label may instead, if desirable, be incorporated into the blocking groups of formula "Z". The linker can be acid labile, photolabile or contain a disulfide linkage. Other linkages, in particular phosphine-cleavable azide-containing linkers, may be employed in the invention as described in greater detail in WO 2004/018497, the contents of which are incorporated herein in their entirety.

Preferred labels and linkages included those disclosed in WO 03/048387. This reference is incorporated herein in its entirety.

In one embodiment the modified nucleotide or nucleoside will have a base attached to a detectable label via a cleavable linker, characterised in that the cleavable linker contains a moiety selected from the group comprising:

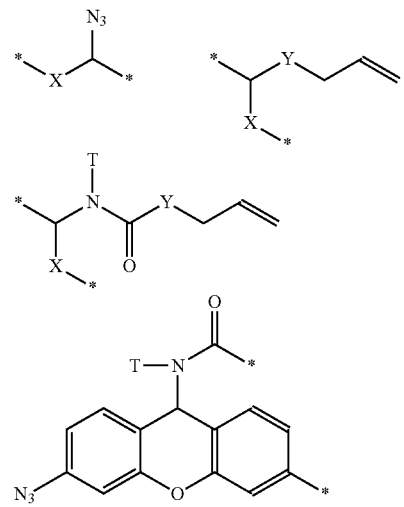

(wherein X is selected from the group comprising O, S, NH and NQ wherein Q is a C$_{1-10}$ substituted or unsubstituted alkyl group, Y is selected from the group comprising O, S, NH and N(allyl), T is hydrogen or a C$_{1-10}$ substituted or unsubstituted alkyl group and * indicates where the moiety is connected to the remainder of the nucleotide or nucleoside).

In one embodiment the detectable label comprises a fluorescent label. Suitable fluorophores are well known in the art. In a preferred embodiment each different nucleotide type will carry a different fluorescent label. This facilitates the identification of incorporation of a particular nucleotide. Thus, for example modified Adenine, Guanine, Cytosine and Thymine would all have attached a separate fluorophore to allow them to be discriminated from one another readily. Surprisingly, the inventors have found that the altered polymerases are capable of incorporating modified nucleotide analogues carrying a number of different fluorescent labels. Moreover, the polymerases are capable of incorporating all four bases. These properties provide substantial advantages with regard to use in nucleic acid sequencing protocols.

As aforesaid, mutant enzymes having the motif A region sequences YAV and YAS are the most preferred for incorporation of nucleotide analogues containing O-azido methyl functionality at the 3' position. It will be appreciated that for other nucleotide analogues the preferred amino acid sequence of the motif A region for optimum incorporation may vary. For any given nucleotide analogue, optimum region A sequence preferences may be determined by experiment, for example by construction of a library or discrete number of mutants followed by testing of individual variants in an incorporation assay system.

However, it has been shown that the preferred region A variant polymerases identified herein also exhibit improved incorporation of modified nucleotides containing a number of different O-azido methyl blocking groups bearing further substituents which increase the overall size of the 3' blocking group, also modified nucleotides containing 3' blocking groups that are not based on the O-azido methyl functionality and modified nucleotides bearing a number of different fluorescent labels. Hence, it may be concluded that the altered polymerases of the invention are capable of improved incorporation of a wide range of modified nucleotides having large 3' substituent groups of differing sizes and of varied chemical nature.

Preferred Uses of the Altered Polymerases

In a further aspect the invention relates to use of an altered polymerase according to the invention for the incorporation of a nucleotide into a polynucleotide.

In a preferred embodiment the nucleotide is a modified nucleotide which has been modified at the 3° sugar hydroxyl such that the substituent is larger in size than the naturally occurring 3' hydroxyl group.

The polymerases of the invention may be used in any area of technology where it is required/desirable to be able to incorporate modified nucleotides having a substituent at the 3' sugar hydroxyl position which is larger in size than the naturally occurring hydroxyl group into a polynucleotide chain. They may be used in any area of technology where any of the desirable properties of the enzyme, specifically improved rate of incorporation of nucleotide analogues, ability to incorporate labelled (e.g. fluorescent) analogues, ability to incorporate all four bases, activity at low temperature and/or over a wide temperature range, activity at low substrate concentration, activity over multiple cycles of incorporation, and high fidelity, provides an advantage. This could be a practical, technical or economic advantage.

Although the altered polymerases exhibit desirable properties in relation to incorporation of modified nucleotides having a large 3' substituent, the utility of the enzymes need not be confined to incorporation of such nucleotide analogues. The desirable properties of the altered polymerase may provide advantages in relation to incorporation of any other nucleotide, including unmodified nucleotides, relative to enzymes known in the art. In essence, the altered polymerases of the invention may be used to incorporate any type of nucleotide that they have the ability to incorporate.

The polymerases of the present invention are useful in a variety of techniques requiring incorporation of a nucleotide into a polynucleotide, which include sequencing reactions, polynucleotide synthesis, nucleic acid amplification, nucleic acid hybridisation assays, single nucleotide polymorphism studies, and other such techniques. All such uses and methods utilizing the modified polymerases of the invention are included within the scope of the present invention.

The invention also relates to a method for incorporating nucleotides which have been modified at the 3' sugar hydroxyl such that the substituent is larger in size than the naturally occurring 3 hydroxyl group into DNA comprising allowing the following components to interact:

A polymerase according to the present invention (as described above)
a DNA template; and
a nucleotide solution containing the nucleotides which have been modified at the 3' sugar hydroxyl such that the substituent is larger in size than the naturally occurring 3 hydroxyl group.

The above components are allowed to interact under conditions which permit the formation of a phosphodiester linkage between the 5' phosphate group of a modified nucleotide and a free 3' hydroxyl group on the DNA template, whereby the modified nucleotide is incorporated into a polynucleotide.

The incorporation reactions may occur in free solution or the DNA templates may be fixed to a solid support.

In order for the polymerases of the invention to be of practical use in any area of technology where it is required/desirable to be able to incorporate modified nucleotides having a substituent at the 3' sugar hydroxyl position which is larger in size than the naturally occurring hydroxyl group into a polynucleotide chain, it is required only that the enzyme be able to incorporate the analogue at an acceptable rate. An "acceptable" rate of incorporation in practical terms may be defined as detectable (i.e. above background) product conversion on one or more cycles of enzymology at 45° C., 50 mM Tris, pH8, 4 mM $MgSO_4$, 0.05 (v/v) Tween, 50 μg/ml enzyme, and 2 μM 3' modified nucleotide in the assay system of Example 2. In preferred embodiments the polymerase may exhibit a time to 50% product conversion on the second cycle of enzymology at 45° C., 50 mM Tris, pH8, 4 mM $MgSO_4$, 0.05 (v/v) Tween, 50 μg/ml enzyme, and 2 μM 3' modified nucleotide of 19.5 min or less, more preferably 5 min or less and most preferably 1.5 min or less.

The rate of incorporation of the 3' modified nucleotide analogue exhibited by a mutant enzyme may be similar to the rate of incorporation of unmodified nucleotides exhibited by the mutant enzyme, or the equivalent wild type enzyme from which it is derived. However, it is not necessary for the rate of incorporation of 3' modified analogues to be similar to that of unmodified nucleotides for a mutant enzyme to be of practical use. All that is required is for the incorporation rate of the 3' modified analogue to be "acceptable" according to the definition provided above on at least one cycle of incorporation. The rate of incorporation may be less than, equal to or greater than the rate of incorporation of unmodified nucleotides and/or nucleotides modified such that the substituent is smaller than a hydroxyl group.

In one particular embodiment of the invention, the altered polymerases of the invention may be used to incorporate modified nucleotides into a polynucleotide chain in the context of a sequencing-by-synthesis protocol. In this particular aspect of the method the nucleotides which have been modified at the 3' sugar hydroxyl such that the substituent is larger in size than the naturally occurring hydroxyl group will be detected in order to determine the sequence of a DNA template.

Thus, in a still further aspect, the invention provides a method of sequencing DNA comprising allowing the following components to interact:

A polymerase according to the present invention (as described above)
a DNA template; and
a nucleotide solution containing the nucleotides which have been modified at the 3' sugar hydroxyl such that the substituent is larger in size than the naturally occurring 3' hydroxyl group followed by detection of the incorporated modified nucleotides thus allowing sequencing of the DNA template.

The DNA template for a sequencing reaction will typically comprise a double-stranded region having a free 3' hydroxyl group which serves as a primer or initiation point for the addition of further nucleotides in the sequencing reaction. The region of the DNA template to be sequenced will overhang this free 3' hydroxyl group on the complementary strand. The primer bearing the free 3° hydroxyl group may be added as a separate component (e.g. a short oligonucleotide) which hybridises to a region of the template to be sequenced. Alternatively, the primer and the template strand to be sequenced may each form part of a partially self-complementary nucleic acid strand capable of forming an intramolecular duplex, such as for example a hairpin loop structure. Nucleotides are added successively to the free 3' hydroxyl group, resulting in synthesis of a polynucleotide chain in the 5' to 3' direction. After each nucleotide addition the nature of the base which has been added will be determined, thus providing sequence information for the DNA template.

Such DNA sequencing may be possible if the modified nucleotides can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3 block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

In a preferred embodiment the modified nucleotides carry a label to facilitate their detection. Preferably this is a fluorescent label. Each nucleotide type may carry a different fluorescent label. However the detectable label need not be a fluorescent label. Any label can be used which allows the detection of the incorporation of the nucleotide into the DNA sequence.

One method for detecting the fluorescently labelled nucleotides, suitable for use in the second and third aspects of the invention, comprises using laser light of a wavelength specific for the labelled nucleotides, or the use of other suitable sources of illumination.

In one embodiment the fluorescence from the label on the nucleotide may be detected by a CCD camera.

If the DNA templates are immobilised on a surface they may preferably be immobilised on a surface to form a high density array. Most preferably, and in accordance with the technology developed by the applicants for the present invention, the high density array comprises a single molecule array, wherein there is a single DNA molecule at each discrete site that is detectable on the array. Single-molecule arrays comprised of nucleic acid molecules that are individually resolvable by optical means and the use of such arrays in sequencing are described, for example, in WO 00/06770, the contents of which are incorporated herein by reference. Single molecule arrays comprised of individually resolvable nucleic acid molecules including a hairpin loop structure are described in WO 01/57248, the contents of which are also incorporated herein by reference. The polymerases of the invention are suitable for use in conjunction with single molecule arrays prepared according to the disclosures of WO 00/06770 of WO 01/57248. However, it is to be understood that the scope of the invention is not intended to be limited to the use of the polymerases in connection with single molecule arrays.

Single molecule array-based sequencing methods may work by adding fluorescently labelled modified nucleotides and an altered polymerase to the single molecule array. Complementary nucleotides would base-pair to the first base of each nucleotide fragment and would be added to the primer in a reaction catalysed by the improved polymerase enzyme. Remaining free nucleotides would be removed.

Then, laser light of a specific wavelength for each modified nucleotide would excite the appropriate label on the incorporated modified nucleotides, leading to the fluorescence of the label. This fluorescence could be detected by a suitable CCD camera that can scan the entire array to identify the incorporated modified nucleotides on each fragment. Thus millions of sites could potentially be detected in parallel. Fluorescence could then be removed.

The identity of the incorporated modified nucleotide would reveal the identity of the base in the sample sequence to which it is paired. The cycle of incorporation, detection and identification would then be repeated approximately 25 times to determine the first 25 bases in each oligonucleotide fragment attached to the array, which is detectable.

Thus, by simultaneously sequencing all molecules on the array, which are detectable, the first 25 bases for the hundreds of millions of oligonucleotide fragments attached in single copy to the array could be determined. Obviously the invention is not limited to sequencing 25 bases. Many more or less bases could be sequenced depending on the level of detail of sequence information required and the complexity of the array.

Using a suitable bioinformatics program the generated sequences could be aligned and compared to specific reference sequences. This would allow determination of any number of known and unknown genetic variations such as single nucleotide polymorphisms (SNPs) for example.

The utility of the altered polymerases of the invention is not limited to sequencing applications using single-molecule arrays. The polymerases may be used in conjunction with any type of array-based (and particularly any high density array-based) sequencing technology requiring the use of a polymerase to incorporate nucleotides into a polynucleotide chain, and in particular any array-based sequencing technology which relies on the incorporation of modified nucleotides having large 3' substituents (larger than natural hydroxyl group), such as 3' blocking groups.

The polymerases of the invention may be used for nucleic acid sequencing on essentially any type of array formed by immobilisation of nucleic acid molecules on a solid support. In addition to single molecule arrays suitable arrays may include, for example, multi-polynucleotide or clustered arrays in which distinct regions on the array comprise multiple copies of one individual polynucleotide molecule or even multiple copies of a small number of different polynucleotide molecules (e.g. multiple copies of two complementary nucleic acid strands).

In particular, the polymerases of the invention may be utilised in the nucleic acid sequencing method described in WO 98/44152, the contents of which are incorporated herein by reference. This International application describes a method of parallel sequencing of multiple templates located at distinct locations on a solid support. The method relies on incorporation of labelled nucleotides into a polynucleotide chain.

The polymerases of the invention may be used in the method described in International Application WO 00/18957, the contents of which are incorporated herein by reference. This application describes a method of solid-phase nucleic acid amplification and sequencing in which a large number of distinct nucleic acid molecules are arrayed and amplified simultaneously at high density via formation of nucleic acid colonies and the nucleic acid colonies are subsequently sequenced. The altered polymerases of the invention may be utilised in the sequencing step of this method.

Multi-polynucleotide or clustered arrays of nucleic acid molecules may be produced using techniques generally known in the art. By way of example, WO 98/44151 and WO 00/18957 both describe methods of nucleic acid amplification which allow amplification products to be immobilised on a solid support in order to form arrays comprised of clusters or "colonies" of immobilised nucleic acid molecules. The contents of WO 98/44151 and WO 00/18957 relating to the preparation of clustered arrays and use of such arrays as templates for nucleic acid sequencing are incorporated herein by reference. The nucleic acid molecules present on the clustered arrays prepared according to these methods are suitable templates for sequencing using the polymerases of the invention. However, the invention is not intended to use of the polymerases in sequencing reactions carried out on clustered arrays prepared according to these specific methods.

The polymerases of the invention may further be used in methods of fluorescent in situ sequencing, such as that described by Mitra et al. Analytical Biochemistry 320, 55-65, 2003.

The invention is now further described in the following non-limiting examples and accompanying drawings in which:

FIG. 1 compares the ability of the library of altered 9° N DNA polymerases to incorporate modified nucleotides against the 9DM control 9° N DNA polymerase. The relative increase in rate is given for each of the altered 9° N DNA polymerases tested.

FIG. 2 illustrates the activity (% product conversion vs time (minutes)) for various polymerases on a first cycle of enzyme of enzymology at 45° C., 50 mM Tris pH8, 4 mM MgSO$_4$, 0.05 (v/v) Tween, 50 µg/ml enzyme and 2 µM 3' modified nucleotide.

FIG. 3 illustrates the activity (% product conversion vs time (minutes)) of the 9° N ED mutant polymerase and the 9° N YAV mutant polymerase compared to the control 9° N DM polymerase on a single cycle of nucleotide incorporation using three different uracil nucleotide analogues: 3' O-allyl, 3'S-methyl and 3' O-azido methyl).

FIG. 4 illustrates the activity (% product conversion vs time (minutes)) of mutant polymerases 9° N DM V409A and 9° N DM V409G compared to the control 9° N DM polymerase on two cycles of incorporation of O-azido methyl modified nucleotide.

EXAMPLE 1

Figure 1:
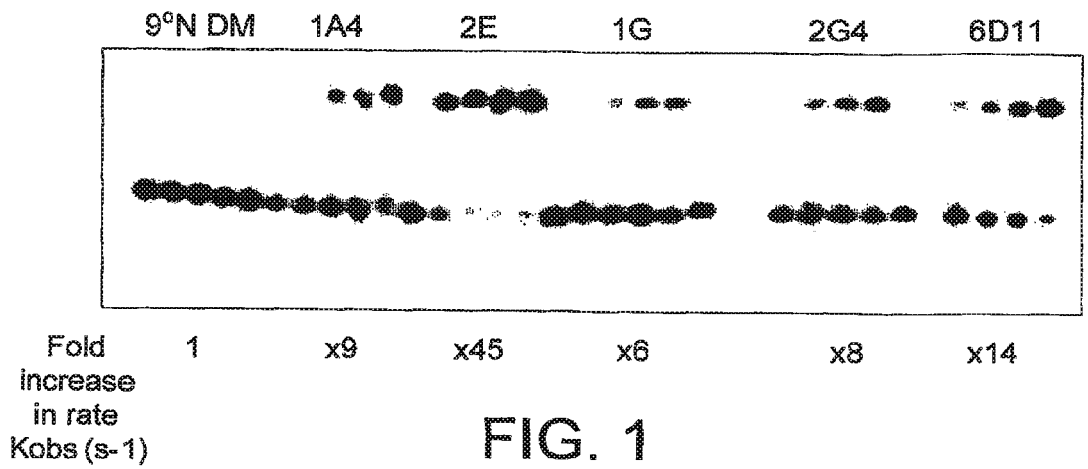
Figure 2:
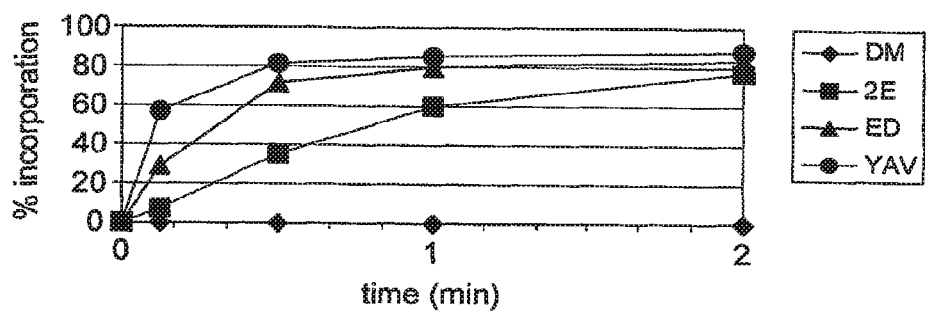

Herein is reported a series of polymerase variants that improve the incorporation of 3' modified nucleotide analogues. Some of these variant enzymes share sequence similarity to each other over the six randomised amino acid residues; by contrast, other enzymes that show improved incorporation bear no sequence similarity in these regions.

Mutations were introduced simultaneously at two regions of the 9° N DNA polymerase sequence, residues 408-410, and residues 484-486. A library of polymerase variants was screened for the incorporation of the 3' modified nucleotide analogues. Variants that displayed enhanced levels of incorporation compared to the parental clone were purified and tested to confirm their activity.

The variant polymerases have increased activity towards the modified nucleotides utilised in the experiments. Thus, they appear to incorporate nucleotide analogues which have been modified at the 3 sugar hydroxyl such that the substituent is larger in size than the naturally occurring 3' hydroxyl group in primer extension assays faster than previously available polymerases which can act as a control polymerase, such as the 9° N (–exo)Y409V/A485L double mutant (designated 9DM herein).

TABLE II

Comparison of the amino acid sequence of novel improved DNA polymerases across the regions targeted for mutagenesis. The sites of the various substitution mutations in the 9°N DNA polymerase amino acid sequence are shown compared to the wild type 9°N DNA polymerase amino acid sequence and the 9DM 9°N DNA polymerase amino acid sequence. Mutations were carried out in 2 regions, Motif A (amino acid 408-410) and Motif B (amino acid 484-486). Each clone was given an individual identifier, a short name to allow easy identification.

| Clone name | Motif A | | | Motif B | | |
|---|---|---|---|---|---|---|
| | Amino Acid number | | | | | |
| | 408 | 409 | 410 | 484 | 485 | 486 |
| Wild Type | L | Y | P | R | A | I |
| 9DM | L | V | P | R | L | I |
| 1A4 | W | A | L | S | K | N |
| 1A2 | D | V | G | G | R | D |
| 1E | M | L | F | K | H | N |
| 1G | V | D | G | G | A | L |
| 2E | V | A | L | I | S | N |
| 2G4 | S | S | L | N | A | Q |
| 6D11 | Y | A | L | T | H | H |

Methods:

Construction of a Library of Mutant Polymerases.

There are many methods for introducing mutations into DNA (see Sambrook and Russell, 2001 and references therein for examples). One method that has been used is described below for the mutagenesis of 9° N at amino acids 408-410 and 484-486.

A sequenced and functionally validated clone of the polymerase is used as the starting material. In this particular example the plasmid from the 9° N (–exo) Y409V/A485L (9° N DM) double mutant was utilised (SEQ ID NO:15).

Table III shows the nucleotide sequences of the oligonucleotide primers used in order to generate the library of mutant 9° N DNA polymerases in the mutagenesis experiments.

| Long name | Short name | Nucleotide sequence |
|---|---|---|
| reamp 9° N atg long | 133-2 SEQ ID NO: 1 | CACTCATGATTAGATCTCGTGCAGC |
| 9° N atg long | 133-1 SEQ ID NO: 2 | CACTCATGATTAGATCTCGTGCAGCCCATGGTGATTCTCGATACCGACTACATCACCG |
| 9° N 1221-1198 | 125-1 SEQ ID NO: 3 | CGAGCGGAAGTCTAAATACACAAT |

-continued

| Long name | Short name | Nucleotide sequence |
|---|---|---|
| 9° N 1198-1221 | 119-S SEQ ID NO: 4 | 3ATTGTGTATTTAGACTTCCGCTCG |
| 9° 11 1198-1251 NNK | 119-3 SEQ ID NO: 5 | ATTGTGTATTTAGACTTCCGCTCGNNKNNKNNKTCG ATCATCATAACCCACAAC |
| 9° 11 1483-1428 | 119-6 SEQ ID NO: 6 | GTAGAAGCTGTTGGCGAGGATCTTMNNMNNMNNCTG CCTGTAATCGAGGAGTTTC |
| 9° N 1483-1460 | 119-7 SEQ ID NO: 7 | GTAGAAGCTGTTGGCGAGGATCTT |
| 9° N 1460-1483 | 125-2 SEQ ID NO: 8 | AAGATCCTCGCCAACAGCTTCTAC |
| 9° 11 term long | 133-3 SEQ ID NO: 9 | GTCGTAGTCGGATGCTAACTACCAGGATCCTCAATG CTTCTTCCCCTTCACCTTCAGCCACGC |
| reamp 9° N term long | 133-4 SEQ ID NO: 10 | GTCGTAGTCGGATGCTAACTACCAGG |

1. The polymerase chain reaction (PCR) method was utilised following standard laboratory procedures (eg. Sambrook and Russell, 2001) 50 microliter reactions contained the 9° N DM template, dNTPs, a suitable reaction buffer and PFU turbo hotstart (stratagene) following manufacturer's guidelines. Following an initial incubation at 94° C. for 10 sec, the DNA was amplified through 25 cycles, each containing three steps: 94° C., 10 sec; 50° C., 30 sec; 68° C., 150 sec to produce the following products:
2. product 1:—'9° N atg long' vs '9° N 1221-1198'=(133-1vs 125-1).
3. product 2:—'9° N term long' vs '9° N 1460-1483'=(133-3 vs 125-2).
4. product 3:—'9° N 1198-1251 NNK' vs '9° N 1483-1428'=(119-3vs 119-6).
5. Analyse 5 µl on a gel, digest the remainder of the volume using DpnI (1 µl), then gel purify the digested products.
6. Combine 2 µl each of product 1 and product 3, amplify with primers, '9° N 1483-1460' vs 'reamp 9° N atg long'= (119-7 vs 133-2) using the conditions above.
7. Combine 2 µl each of product 3 and product 2, amplify with primers, '9° N 1198-1221' vs 'reamp 9° N term long'=(119-5vs 133-3) using the conditions above.
8. Gel purify both products, combine 2 µl of each and reamplify with 'reamp 9° N atg long' vs 'reamp 9° N term long'=(119-7 vs133-4) using the conditions above.
9. The final DNA product was digested with NcoI (50 units) and BamHI (100 units) restriction enzymes for 2 hours at 37° C., and this fragment further purified using a Qiaquick procedure (Qiagen) following manufacturer's instructions. The resulting DNA was ligated into pET3d plasmid (Novagen), cut with NcoI and BamHI enzymes following standard procedures (Sambrook and Russell, 2001).

Transformation

A portion of the ligation was transformed directly into an strain of *E. coli*, such as BL21 (DE3) plysS, that allows expression of the variant genes, or alternatively into an intermediate host, such as *E. coli* DH5Alpha.

1. A transformation was carried out following standard procedures provided by manufacturer's of the relevant competent cells. Cells were plated onto two 20 cm×20 cm LB agar and carbencillin (LBC) plates.
2. Colonies were grown overnight and an approximation of numbers indicated 50,000 independent clones.
3. The plates were overlaid with 50 ml each of LB carbenicillin broth. The colonies were manually agitated into solution with a disposable bacterial spreader. The liquor was transferred to several falcon tubes and further agitated manually to ensure that all colonies were distributed into the medium.
4. The tubes were transferred to an orbital shaker for incubation at 37° C. for two hours.
5. The bacterial broth was harvested and library plasmid DNA extracted by standard procedures.
6. The library plasmid DNA was used to transform BL21 (DE3) pLysS bacterial expression hosts and a titre of colony forming units (CFU's) established for this plasmid preparation/host combination.

Screening Colonies for Incorporation of 3' Modified Nucleotide Analogues

There are many different methods for screening for nucleotide incorporation that are variations on the method of Sagner et al. (1991). One suitable method is described herein for the incorporation of 3' modified nucleotide analogues that uses a digoxigenin-3-O-methyl-carbonyl-e-aminocaproic acid (DIG) derivative of the relevant nucleotide analogue (ffT-DIG)

Day 1
1. Transform library ligation into BL21(DE3)*pLysS strain (Invitrogen) and plate out onto a LB agar plate supplemented with 100 µg/ml carbenicillin (carb) and 34 µg/ml chloramphenicol (cam). Aim for 1×10exp5 colonies per 22 cm² plate. Incubate at 37° C. overnight.

Day 2
2. Pre-wet a Hybond C Extra nitrocellulose filter (Amersham Pharmacia Biotech) on a fresh LB agar plate supplemented with 100 µg/ml carbenicillin, 34 chloramphenicol and 1 mM IPTG. Number the filter with a black biro and also number the plate from which the filter was taken. Carefully, so as not to trap air bubbles, lay the wetted filter paper over the colonies and leave for approximately 1 minute. Mark orientation marks with a needle (one, two and three spots around perimeter of filter to help alignment later). Carefully lift off the filter paper and place colony side up on the carb/cam/IPTG plate. Get rid of all air bubbles by lifting paper and re-laying. Incubate this filter on the plate at 37° C. for 4 hours. Also, incubate the original plate from which the colony lift was performed to allow the colonies to re-grow.
3. Lysis
Add 2 µl of Benzonase (Novagen) to 50 ml of Cell Lytic B Bacterial Cell lysis/extraction reagent (Sigma) solution. Pour over a square of 3 MM paper (Whatman) on a white tray and iron out any bubbles and remove excess solution by rolling over with a 10 ml pipette until flat and moist but not too wet. Pour off excess solution. Place filter on this paper colony side up for 1 hour at room temperature. Check 3 MM paper does not dry out. Preheat oven at 80° C.
4. Heat Treatment
Place 3 MM paper in new petri dish and wet with dH₂O. Pour off excess dH₂O and flatten paper using end of 5 ml pipette. Place filter colony side up on wetted 3 MM paper and seal petri dish with red electrical tape. Place in humidity box in 80° C. oven (already equilibrated to 80° C. with some water in the bottom of the tray) for 1 hour. (For big 22 cm² plates place in autoclave bag taped up instead of humidity box). Defrost 10× Thermopol buffer (New England Biolabs).

5. Incorporation

Remove tape and 3 MM paper and place filter back in petri dish. Add incorporation solution pre-warmed to temperature that incorporation will be tested at. (1× Thermopol solution pH 8.8+0.05 μM ffT-DIG 0.05 μM dATP, dCTP, dGTP per filter). Use 10 ml volume per small round petri dish. (Use 90 ml for big 22 cm² plates). If incubating at 45° C. or higher place tape around outside of petri dish. Incubate at required temperature statically for 30 min.

6. Washing

Pour off incorporation buffer and rinse with dH₂O. Wash 2×5 min with DIG wash buffer (Roche) on rocker. Incubate in approx 10 ml DIG blocking buffer (Roche) on rocker overnight. (50 ml DIG blocking buffer for big 22 cm² plates).

Day 3

7. Antibody Binding and Detection

Dilute anti-DIG alkaline phosphatase-conjugated antibody (Roche) 1:5000 in 10 ml DIG blocking buffer per small round filter (50 ml for big 22 cm² plates). Incubate filters with antibody for 45 min at room temperature on rocker. Wash filters twice with DIG wash buffer for 15 min each on rocker. Equilibrate filters with 10 ml DIG detection buffer (Roche) for 2 min on rocker (50 ml for big 22 cm² plates). Add 20 μl NBT/BCIP (Roche) to 10 ml fresh DIG detection solution per small round filter and incubate at room temperature on rocker for 20 min (100 μl NBT/BCIP to 50 ml DIG detection solution for big 22 cm² plates. Petri dishes containing filters should be wrapped in foil during detection. Rinse filter thoroughly with tap water for a few minutes to stop reaction. Dry filters on 3 MM paper at 37° C.

Generalised Incorporation Experiment

This is a generalised method. Make a 15 polyacrylamide/urea sequencing gel according to standard procedures (Sambrook and Russell, 2001). For each time point add 5 μl formamide-bromophenol blue, cyanideloading dye (Sigma; stop mix) to labelled eppendorf in rack. Also, have ready eppendorf containing 1 μl CHASE mix for each reaction. Thaw all freezer components on ice.

Example Reaction Mix

For each reaction, mix together in eppendorf on ice:
5 μl 2 μM template
2.5 μl 2 U/μl 9° N DM
5 μl 10× Thermopol buffer, or Tris-HCl, 50 mM, pH 8
30.5 μl dH₂O
(50 μl total volume)

Other components of mix routinely used might be MnCl₂, Tween, NaCl or other salts, EDTA and DTT. When other buffers or chemicals are used to test incorporation conditions. Place tubes in hot block set at 65° C., lower as necessary. Add 5 μl labelled primer (1 μM) to each reaction. For 0 min time point, remove 5 μl to 0 min time point tube containing 5 μl stop mix. Initiate reactions by adding 2 μl of 100 mM MgSO₄ dNTPs, or nucleotide analogues, as appropriate, and at the required concentration (eg. 2 micromolar each). Start timer immediately after adding MgSO₄/dNTP mix to first reaction. At each time point remove 5 μl to appropriate time point tube in rack containing 5 μl stop mix. After final time point, add 5 μl of reaction to 1 μl CHASE mix in eppendorf. Incubate at 65° C. for 10 min. Add 5 μl formamide loading dye. Load 3 μl of each reaction on gel. Run gel at 55 W for 2 h 15 min. Dry gel. Expose to phosphor screen overnight, scan using a phosphoimager instrument, and analyse with appropriate software.

EXAMPLE 2

In example 1 the so-called "double mutant" variant of the archaeal 9° N DNA polymerase that contains mutations in the 3'-5' exonuclease domain (amino acids D141A; D143A) and in the catalytic site of the enzyme (amino acids Y409V; A485L) was modified to incorporate mutations at two distinct regions of the protein, herein named as region A (amino acids 408-410) and region B (amino acids 484-6). As a result a panel of seven altered polymerases were described, each of which carries mutations at both regions A and B.

In order to identify which region was responsible for the improved activity, a polymerase variant was constructed that carried only the changes in region A (these being the region A mutations VAL from the "2E" variant); region B was reverted back to the parental sequence of 9° N DM (A485L). This variant, known as "ED", demonstrated an enhanced rate of incorporation of the modified nucleotides compared to the original mutant bearing changes at regions A and B together. This suggested that the mutation of only a single region of the polymerase gene could encode proteins that had enhanced enzymatic activity with 3' modified nucleotide analogues compared to control polymerases. Therefore, from this observation a large panel of polymerase variants that carried changes in region A alone were constructed and screened for incorporation of the nucleotide analogues.

The polymerase variants that were identified from the screen of region A clones showed enhanced rates of incorporation of nucleotide analogues compared to the parental protein 9° N DM, and many of these new variants demonstrated improved, activity compared to the ED polymerase. Furthermore, mutations to a third region of the polymerase (herein called region C; amino acids 493, 494 and 496 of 9° N polymerase), which together with region A forms part of the nucleotide binding pocket in the protein, did not result in improvements to the polymerase activity. These data demonstrated that changes to only certain amino acids within the nucleotide binding pocket that are important for the enhanced activity of the new polymerases.

Materials and Methods

Construction of Clone ED

The polymerase variant ED is a derivative of the 9° N DM DNA polymerase that bears the following mutations: L408V; V409A; P410L. This clone can be constructed in a variety of ways following standard molecular biology methods. One method for the construction of a gene encoding ED is described herein, and was used in our experiments.

DNA encoding the 2E gene product (as described in Example 1) was isolated and digested with restriction enzyme XhoI (New England Biolabs, NEB) following manufacturer's instructions. The resulting DNA fragment that encodes the region spanning amino acids 408-410 was purified from an agarose gel using standard methods. This DNA fragment was then ligated into the XhoI-digested vector backbone of the 9° N DM plasmid pNEB917(NEB; as described Example 1) using T4 DNA ligase (NEB), following standard procedures. The background of religated vector backbone was reduced by prior treatment with calf-intestinal phosphatase (NEB) following standard procedures. The product of the ligation reaction was transformed into library efficiency *E. coli* DH5alpha competent cells (Invitrogen) following manufacturers instructions. Colonies were then screened by PCR using oligonucleotide primers that bind specifically to the 2E sequence (primer 2E 408-10; sequence 5' GACTTCCGCTCGGTTGCGTTG 3' SEQ ID NO:23) and the 9° N DM vector backbone (primer sequence 5' AAGCCCCTCACGTAGAAGCC 3' SEQ ID NO:24) in a 20 µl reaction mixture of the following composition: DNA/colony solution in water, 1 µl; 0.1 µM primers; 200 uM dNTPs; 1 unit Taq DNA polymerase; 2 µl 10× Taq reaction buffer. Reactions were cycled 30 times at 94° C., 1 min, 55° C., 1 min, 72° C., 2 min and positive colonies identified by inspection of the reaction products by agarose gel electrophoresis.

Construction of a Library of Clones with Variation in Region A (Encoding Amino Acids 408-410)

The construction of a library of mutant proteins can be performed by different methods. The method used in this work involved two stages: the formation of a degenerate mix of DNA templates that encode the mutant polymerases, and the cloning of these DNA fragments into a suitable expression vector. The pool of degenerate DNA templates was formed by PCR using oligonucleotide primers Xba 408-410 (5' GTGTATCTAGACTTCCGCTCGNNKNNKNNKT-CAATCATCATAACCCACAAC 3' SEQ ID NO:25; N, equimolar mixture of G, A, T and C bases; K, an equimolar mixture of G and T bases) and BamHI 3' 9° N 5' GTTAGCAGCCGGATCCTCACTTCTTCCCCT-TCACCTTCAGCCACGC 3' SEQ ID NO:26) which hybridise to the 9° N DM gene sequence. The DNA fragment was amplified by PCR in a 20 µl reaction as described above, using long 9° N DM template DNA. The 1200 bp DNA product was gel purified using a gel purification method (Qiagen) following the manufacturer's instructions, and the fragment digested with restriction enzymes XbaI and BamHI (NEB), using the 10× BamHI buffer (NEB) as recommended by the manufacturer. In the second stage, these DNA fragments were cloned into the XbaI-BamHI vector backbone of expression plasmid pSV13, a derivative of pNEB917 (NEB), which was constructed in a two step procedure, as follows. Firstly, the XbaI restriction site in the polylinker of the pNEB917 plasmid was destroyed by cutting the plasmid with XbaI, extension of the resulting 3' overhang with Klenow polymerase, and relegation of blunt-ended DNA with T4 ligase, using standard molecular biology procedures (Sambrook and Russell, 2001). This plasmid, pSV12, was then mutated further to form pSV13 by the introduction of a unique XbaI site at position 1206 in the 9° N DNA sequence. This mutation was performed by PCR mutagenesis using oligonucleotide primers XbaI mut 5' (5° GGGACAACATTGTGTATCTAGACTTCCGCTCGCTG-GTGCCTTC 3' SEQ ID NO: 27) and 1769R (5° GTCTAT-CACAGCGTACTTCTTCTTCG 3' SEQ ID NO:28) in one reaction, and XbaI mut 3° (5 GAAGGCACCAGCGAGCG-GAAGTCTAGATACACAATGTTGTCCC 3' SEQ ID NO:29) and 1032F 5° GGCCAGAGCCTCTGGGACGTC 3° SEQ ID NO:30) in a second reaction. PCR cycling conditions for these amplifications were 30 cycles of 95° C. for 1 min, 60° C. for 30 sec and 72° C. for 1.5 min using 1.5 units of Taq and 1 µM of primers per reaction. The products of these PCRs were two partially overlapping DNA fragments that were then used in a second PCR reaction with primers 1032F/1769R to produce a 737 bp DNA product, using identical reaction conditions. This final product was digested with XhoI (XhoI sites at 1040 and 1372 flanked the XbaI mutation) and ligated with XhoI cut pSV12. The orientation of the insertion was checked by restriction digestion and the resulting plasmid named pSV13. Both pSV12 and pSV13 were sequenced over the regions where the changes were made.

After ligation of the degenerate DNA fragments into pSV13, the DNA was transformed into competent E. coli BL21 Star (DE3) plysS (Invitrogen) following the manufacture's procedures, and plated out to single colonies as described in Example 1, In a separate experiment, a different set of oligonucleotide primers was used to generate the mixture of DNA templates for cloning into pSV13. These primers also resulted in the production of degenerate series of bases encoding amino acids 408-410 of 9° N DM; however, in addition to these changes to region A, mutations were also introduced simultaneously to region C spanning amino acids 493, 494 and 496. The method used to make this degenerate pool of DNA fragments involved a 3-way PCR reaction with primers Xba 408-410 (described above) and 493-6Rev (5' GCGTAGC-CGTAMNNGCCMNNMNNGCTGTTGGCGAGGATTTT-GATCAGCCTC SEQ ID NO:31; M represents an equimolar mixture of bases A and C, and N represents an equimolar mixture of all 4 bases) in the first reaction, using reaction conditions as described above. The product of this reaction was then used as the template DNA in a second PCR reaction with primers Xba 408-410 and BamHI 3° (5' GCGCGCGGATCCTCACTTCTTCCCCTTCACC SEQ ID NO:32) using conditions described above. The DNA product from this second PCR was digested with restriction enzymes XbaI and BamHI and cloned into vector pSV13.

Screening Mutant Polymerases for Incorporation of Modified Nucleotides

The screening procedure that was used is described in Example 1. In one experiment, a total of 251 positive colonies were identified from a library of $4.2 \times 10^4$ colonies (A and C regions randomised simultaneously), and in a second experiment, 255 positive colonies were identified from a library of $7 \times 10^4$ colonies (region A randomised alone).

Further Screens of Polymerase Activity on Isolated Colonies

To identify which of the several hundred positive colonies from the filter screen had high incorporation activities, we devised an plate-based assay to measure the enzymatic addition of a Digoxigenin-labelled version of the relevant 3' blocked nucleotide analogue (ffT-DIG; described in Example 1) to a biotinylated oligonucleotide hairpin substrate. E. coli colonies expressing mutant polymerase proteins were grown overnight with shaking and this culture was used to inoculate 0.8 mL LB containing carbenicillin and chloramphenicol and grown with shaking for 3 h at 37° C. After 3 h, protein expression was induced by the addition of 1 mM IPTG, and the culture grown for a further 2.5 h. Cells were pellet by centrifugation, washed and resuspended in 30 µl wash buffer (50 mM Tris HCl pH 7.9, 50 mM Glucose, 1 mM EDTA) containing 4 mg/ml lysozyme, and incubated at room temperature for 15 minutes. Cells were then lysed by the addition of an equal volume of lysis buffer (10 mM Tris HCl pH 7.9, 50 mM KCl, 1 mM EDTA, 0.5% Tween-20) containing 1 mM phenylmethanesulfonyl fluoride (PMSF; Sigma) and 0.5% NP-40 and incubated for 1 h at 75° C. before pelleting the cell debris. The supernatants, which contain the mutant polymerase enzymes, were stored at 4° C.

The incorporation reactions were set up as follows: 10 nM biotinylated substrate DNA was added to the wells of a Strepavidin-coated microtitre plate (Sigma) in 50 mM Tris-HCl, pH 8. Wells were washed with three times with PBS buffer containing 0.05% Tween-20 (PBS-T) before the addition of 0.2 µM ffT-DIG in a volume of 40 µL buffer (50 mM Tris HCl, pH8, 0.05% Tween-20, 4 mM MgSO$_4$), and 10 µL bacterial supernatant containing the recombinant enzyme (above). Reactions were incubated for 15 mins at 30° C. or 65° C. and stopped by the addition of 10 µL 0.5M EDTA.

The reaction solutions were removed and the wells were washed with PBS-T as before. The presence of incorporated DIG was detected using a horseradish peroxidase-linked anti-DIG antibody (Roche) and 3,3',5,5'-tetramethylbenzidine substrate (Sigma).

In some experiments, the recombinant proteins were purified from the bacterial supernatants and the quantity of recombinant protein determined. It was then possible to compare the rates of incorporation reactions of different polymerase enzymes by mixing the DNA substrate, enzyme and fT-DIG in solutions and stopping the reactions at different times by diluting an aliquot (50 µL) of the reaction mixture into 10 µL 0.5M EDTA solution. These different samples were then added to the wells of a streptavidin-coated microtitre plate. The amount of DIG incorporation was measured in an identical fashion to the above procedure.

Protein Purification Method

The DNA encoding the mutant DNA polymerases was transformed into BL21(DE3) RIL Codon Plus competent cells (Stratagene) using the manufacturer's instructions. Single colonies of transformed bacteria were used to inoculate a flask of LB broth containing carbenicillin and chloramphenicol and this culture was grown with shaking overnight at 37° C. This culture was used to inoculate a larger volume of LB broth containing carbenicillin and chloramphenicol at a 1:100 dilution, and this culture was then grown with shaking at 37° C. to an optical density of approximately 0.4-0.6 at 600 nm. Protein expression was induced by the addition of 1 mM IPTG, and the culture grown for a further 2.5 h at 37° C. Cells were pelleted by centrifugation and washed in PBS buffer. Cells were then resuspended in 1/100th original volume of wash buffer (50 mM Tris HCl pH 7.9, 50 mM Glucose, 1 mM EDTA) containing 4 mg/ml lysozyme, and incubated at room temperature for 15 minutes. Cells were then lysed by the addition of an equal volume of lysis buffer (10 mM Tris HCl pH 7.9, 50 mM KCl, 1 mM EDTA, 0.5% Tween-20) containing 1 mM PMSF and 0.5% NP-40 and incubated for 30 mins at room temperature. The samples were then heated at 75° C. for 30 minutes and centrifuged at 18000 rpm for 30 mins at 4° C. to remove denatured protein. After washing the pellet in wash buffer (above), the samples were diluted 3-fold in 10 mM Tris/HCl, pH 7.5, 300 mM NaCL, 0.1 mM EDTA, 0.05% Triton-X-100 and applied to a DEAE FF HiTrap chromatography column (Amersham Biosciences). The target protein was located in the flow through fraction, and further purification is achieved by chromatography using a Heparin FF column (Amersham Biosciences), after dilution in 10 mM KPO4, pH 6.9, 0.1 mM EDTA, 0.05% Triton-X-100. Fractions were eluted from the column in the same buffer and those containing the target protein were identified by SDS-PAGE and staining with Coommassie Brilliant Blue staining as described in Sambrook and Russell, 2001.

Analysis of Incorporation Rates of Mutant Polymerases

The mutant polymerases were assessed for their ability to incorporate a 3' blocked nucleotide analogue using a gel-based assay as described in generic form in Example 1. The rates of incorporation of the modified nucleotides were compared to purified forms of related DNA polymerases in both a single round of incorporation and through two rounds of nucleotide incorporation. The DNA template that was used for these experiments was a commercially-synthesised biotinylated oligonucleotide.

The method for two cycles of incorporation involves the binding of the DNA primer-template to streptavidin-coated beads (Dynalbeads). These are prepared as follows:

Resuspend beads in storage pot by pipetting up and down

Take 20 µL beads

Wash 3×200 µL TE buffer (10 mM Tris HCl pH7.5, 1 mM EDTA)

Add 50 µL B&W buffer (5 mM Tris HCl, pH7.5; 1M NaCl, 0.5 µM EDTA)

25 µL H$_2$O

25 µL of $^{32}$P-labelled biotin DNA template (final concentration of 100 nM)

Throughout the protocol the beads must be agitated every 3-5 minutes to ensure that the reactions are able to proceed.

Incubate for 15 minutes at room temperature

Wash beads 3×200 µL TE buffer

Resuspend in 100 µL of TE and remove a 5 µL sample and add 5 µL gel loading buffer (0.5% bromophenol blue 0.5% xylene cyanol in formamide:H$_2$O 4:1; Sigma B3269) with 0.05 M EDTA Remove TE buffer.

The first cycle of enzymatic incorporation is performed on these beads as follows:

Incorporation mix 1 is added to the bead pellet from above.

Incorporation Mix 1:

| | |
|---|---|
| 2 µL | 0.1 mM 3'modified nucleotide triphosphate |
| 10 µL | 500 mM Tris pH 8.0 |
| 5 µL | 1% Tween-20 |
| 4 µL | 100 mM MgSO4 |

50 µg/ml purified polymerase

H$_2$O to make up the volume to 100 µL

Reactions are incubated at 45° C. for 15 minutes

A 5 µL sample is removed and added to gel loading buffer with EDTA

A second 5 µL sample is also removed to which is added 1 µL of 4 natural nucleotide triphosphates (Sigma) and incubated for a further 10 minutes at 45° C. To 5 µL of this sample is added 1 µl gel loading buffer with EDTA The first cycle of enzymology is then deblocked by treatment with tri(carboxyethyl) phosphine (TCEP) as follows:

Wash beads 3×200 µL TE buffer

Add 65 µL TCEP (100 mM) in water and incubate at 65° C. for 15 minutes

Wash beads 3×200 µL TE buffer

Add 65 µL of TE buffer and take out a 5 µL sample and add to gel loading buffer with EDTA After removal of the TE buffer, a second cycle of enzymatic incorporation is then performed by the addition of incorporation mix 2, as follows:

To the deblocked beads (above) add:

| | |
|---|---|
| 1 µL | 0.1 mM 3' modified nucleotide analogue |
| 5 µL | 500 mM Tris pH 8.0 |
| 2.5 µL | 1% Tween-20 |
| 2 µL | 100 mM MgSO4 |

50 µg/ml purified DNA polymerase

H$_2$O to make up the volume to 50 µL

Take 5 µL samples out at 34, 1, 2, 4, 10, 30, 60 mins and add to gel loading buffer with EDTA.

Heat all samples to 95° C. for 10 mins and load 3 µl on a 12% acrylamide gel (Sambrook and Russell, 2001).

Results
The following are sequences of amino acids 408-410 for DNA polymerases exhibiting improved activity compared to 9° N DM YST
FAI
FAP
VAP
AAA
YAS[&]
YAV[&]
YGI[&]
YSG[&]
SGG[#]
CST
IAL
CGG
SAL
SAA
CAA
YAA
QAS
VSS
VAG
VAV
FAV
AGI
YSS
AAT
FSS
VAL

[#] this polymerase also contained the F493H mutation in region C

[&] this clone was obtained from a library in which both regions A and C were randomised; however, the amino acid sequence of region C was identical to wild type Amino Acid Frequency at Each Position in Region a Among Selected Clones
The frequency of the amino acids at each of the three positions suggests the following sequence preferences:
408: preference for aromatic amino acids, particularly Y and F
preference for amino acids with aliphatic side chains, eg. I, A, V
preference for cysteine and serine (C and S)
absence of charged amino acids (R, K, H, D, E)
absence of proline (P)
occurrence of glutamate (Q)
409: preference for A
preference for amino acids with small side chains (A, S, G)
absence of charged amino acids (R, K, H, D, E)
absence of proline (P)
410: preference for amino acids that have small side chains (S, A, G)
preference for amino acids with beta-branched side chains (I, T, V, L)
preference for proline (P)

Activity of Selected Polymerase Mutants
Time (mins) to 50% product conversion on second cycle of enzymology at 45° C., 50 mM Tris, pH8, 4 mM MgSO$_4$, 0.05 (v/v) Tween, 50 µg/ml enzyme, and 2 µM 3° modified nucleotide. Time to 50% product conversion on first cycle of incorporation shown in parentheses. For other mutants the time to 50% conversion on the first cycle was not measured in these experiments

| Residues 408-10 | time |
|---|---|
| VAL (ED polymerase) | 5.2 min (16 sec) |
| YAS | 1.5 min |
| YAV | 1.2 min (5 sec) |
| FAP | 5.5 min |
| FAI | 2.2 min |
| YST | 2.1 min |
| CST | 19.5 min |
| AAA | 6.9 min |
| CAA | 15 min |
| VAP | 5.9 min |
| 9°N DM | no product conversion under these conditions at first or second cycle |

EXAMPLE 3—INCORPORATION OF DIFFERENT 3 BLOCKED NUCLEOTIDE

Figure 3:
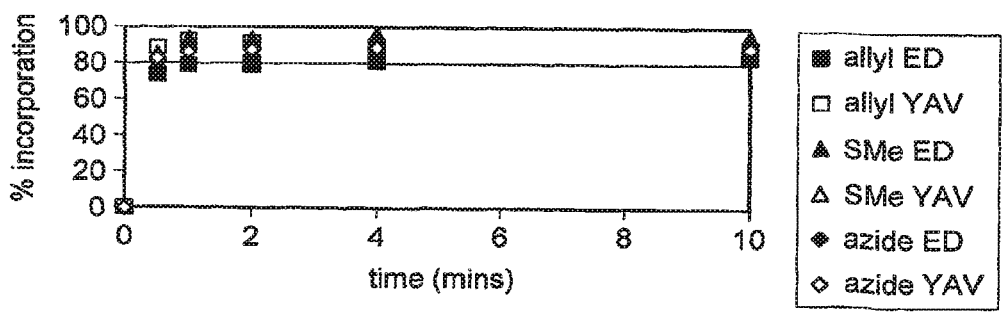

In order to determine whether the modified polymerases described in the previous examples have the capability to incorporate different nucleotide analogues that bear large modifications at the 3' position of the sugar, three different uracil nucleotide analogues (3' 0-allyl, 3'S'-methyl, and 3' O-azido methyl) were tested for their ability to be incorporated by two different modified nucleotides (9° N ED variant polymerase, and 9° N YAV variant polymerase), compared to a control polymerase (9° N DM). A single cycle of nucleotide incorporation was performed at different time intervals using a 'single incorporation' method described below. The results of the incorporation reaction (FIG. 3) demonstrate clearly that nucleotides analogues that bear different 3' modifications on the sugar are all incorporated efficiently by the different DNA polymerases.

Methods

Single Incorporation

1. In a clean reaction tube, mix the following components:
100 nM $^{32}$P-labelled duplex DNA substrate
50 µg/ml isolated DNA polymerase
50 mM TrisHCl, pH 8
0.05% Tween20
water to 47 µL
2. incubate the mixture at 45° C.
3. Add 4 mM MgSO$_4$ and 2 µM 3' modified nucleotide to the reaction mixture from 2, such that the total reaction volume is 50 µL
4. at various time intervals remove 5 µL aliquots from the reaction tube and mix with 5 µL gel loading buffer (described in Example 2)
5. Heat samples and load on acrylamide gels as described in Example 2.

EXAMPLE 4—INCORPORATION OF 3' BLOCKED NUCLEOTIDES, WITH ALL FOUR BASES AND DIFFERENT FLUORESCENT REPORTER GROUPS

To determine if the DNA polymerases described in previous examples were capable of incorporating 3' modified nucleotide derivatives of A, G, C and T bases, and also of incorporating such nucleotide derivatives further modified by different fluorescent reporter groups, a single incorporation reaction (as described in Example 3) was performed with the following 3' O-azido methyl nucleotide derivatives:

TABLE IV

| Base | Dye |
| --- | --- |
| T | Cy3 |
| T | Alexa 647 |
| G | Alexa 594 |
| G | Cy3 |
| C | Alexa 488 |
| C | Cy3 |
| A | Cy3 |
| A | Alexa 594 |
| A | Alexa 594 |
| A | Alexa 488 |
| C | Alexa 488 |
| G | Cy3 |
| T | Alexa 647 |
| T | Alexa 488 |
| T | Alexa 594 |

In each case, the 9° N ED polymerase variant was capable of greater than 90% substrate conversion at a 2 µM concentration of nucleotide within 3 minutes at 45° C.

EXAMPLE 5—ACTIVITY OF DNA POLYMERASES THAT HAVE A SINGLE MUTATION IN REGION A

Figure 4:
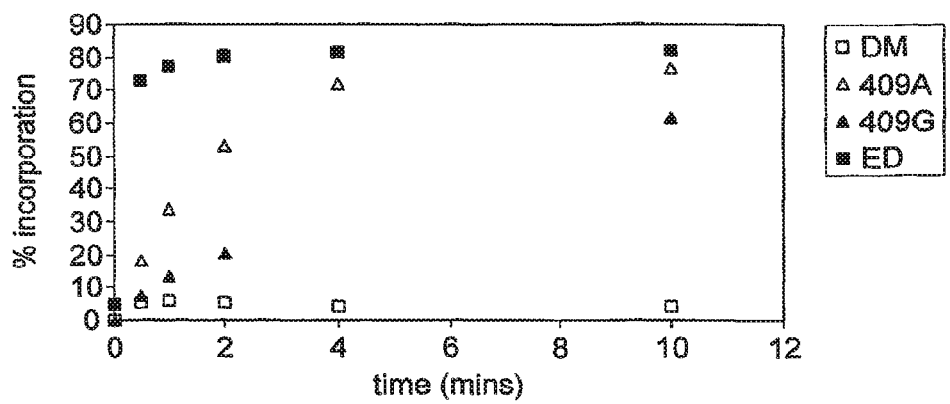

To determine if a single mutation in region A was capable of conferring improved activity upon a control polymerase, point mutations were introduced into the 9° N DM polymerase to change codon 409 into Alanine (9° N DM V409A) or Glycine (9° N DM V409G). Mutations were introduced into the 9° N DM gene using the Quikchange XL site-directed mutagenesis procedure (Stratagene) following the manufacturer's instructions using 9° N DM DNA as template, and mutagenic primer pairs V409A 5' GATGATT-GACGGCGCCAGCGAGCGGAAG 3' (SEQ ID NO: 33) and V409Areverse 5' CTTCCGCTCGCTGGCGCCGT-CAATCATC 3' (SEQ ID NO: 34) for the 9° N DM V409A mutation, and 9DM 409G 5' GATGATTGAAGGGCCCA-GCGAGCGGAAG 3' (SEQ ID NO: 35) and 9DM 409G reverse 5' CTTCCGCTCGCTGGGCCCTTCAATCATC 3° (SEQ ID NO: 36) for the 9° N DM V409G mutation. Positive clones were verified by DNA sequencing and purified preparations of each polymerase were prepared using protocols described in Example 2. To determine the activity of the different polymerases, two cycles of incorporation was performed using a 3' O-azido methyl-modified nucleotide as described in Example 2. The data demonstrates that both 9° N DM V409A and 9° N DM V409G polymerases are capable of incorporation of 3' modified nucleotides to a greater extent than the 9° N DM control polymerase when using a nucleotide that bears a large 3' modification on the sugar (FIG. 4).

EXAMPLE 6—INCORPORATION OF 3' BLOCKED NUCLEOTIDE ANALOGUES BY MODIFIED DNA POLYMERASES AT 30° C.

To measure the incorporation of 3' blocked nucleotide analogues at different temperatures, a modified version of the microtitre-based incorporation assay (described in Example 2) was developed. In this assay, a mixture of biotinylated DNA substrate at 10 nM concentration and purified polymerase enzyme at 50 nM concentration was mixed in a buffer comprising 50 mM Tris, 0.05% Tween 20 and 10 mM KCl. In a separate reaction tube, a mixture of 0.2 µM ffT-DIG (as described in Example 2) and 4 mM MgSO4 was made in an identical buffer to that described for the first mixture. Reaction volumes were adjusted so that the mixture in tube 1 comprised 40 µL, and in tube 2, 10 µL. Depending on the number of timepoints required in the experiment, the reaction volumes were scaled appropriately. All tubes were prewarmed at the appropriate temperature and the contents of tube 2 was added to tube 1 to initiate the incorporation reaction. At various time intervals, 50 µL of the combined reaction mixture was removed and the incorporation reaction terminated by the addition of 100 mM EDTA (final concentration). The different aliquots of stopped reaction mixture were then added to separate wells of a streptavidin-coated microtitre plate, and the extent of ffT-DIG incorporation was assessed as described in Example 2.

Figure 5:
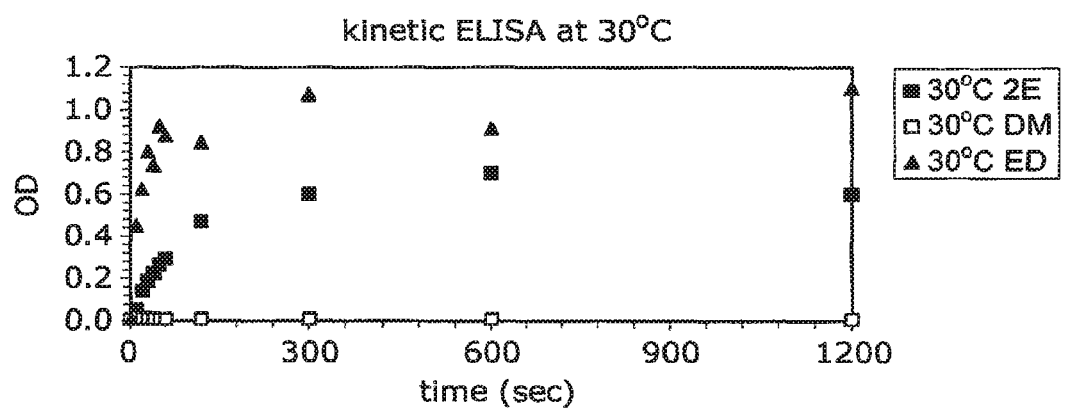
FIG. 5 illustrates the activity (% product conversion vs time (minutes)) of various polymerases at 30° C.

The results of the incorporation of a ffT-DIG nucleotide analogue with the 9° N DM ED and 2E polymerase variants at 30° C. are shown in FIG. 5, together with a comparison of the activity of 9° N DM control polymerase.

EXAMPLE 7—INCORPORATION OF DIFFERENT CONCENTRATIONS OF MODIFIED NUCLEOTIDES BY MODIFIED DNA POLYMERASES

Figure 6:
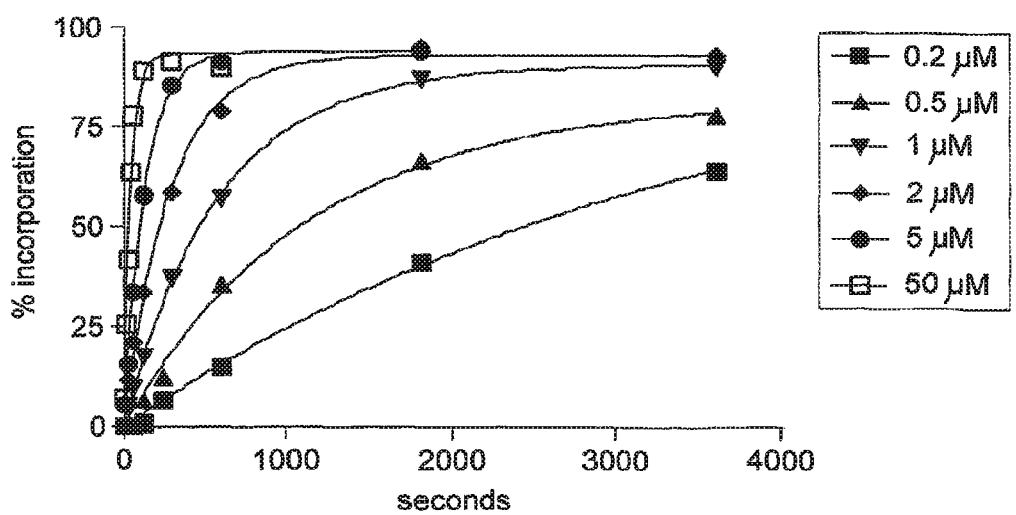
FIG. 6 illustrates incorporation (% incorporation vs time (minutes)) of 3 blocked nucleotide by a 9° N (exo–) mutant polymerase having the amino acid sequence YAV in the motif A region at various different substrate concentrations.

To determine over what range of nucleotide concentrations the modified DNA polymerases were capable of efficient incorporation of the 3' modified nucleotide analogues, a two cycle incorporation experiment was performed as described in Example 2. The incorporation rates for a 3' O-azido methyl-modified nucleotide (described in Example 2) were measured over a range of nucleotide concentrations from 0.2 µM to 50 µM of ffT, and the results for the 9° N YAV variant polymerase (exo−) are shown in FIG. 6. These data demonstrate that the modified polymerases described herein are capable of incorporation of 3' modified nucleotides over a wide range of nucleotide concentrations on the second cycle of enzymatic incorporation. Indeed, these data also suggest that these modified polymerases would be capable of incorporation of 3' blocked nucleotides at concentration in excess of 50 µM, and below 0.2 µM. Furthermore, it has been possible to determine the rates of nucleotide incorporation at the first cycle of enzymatic incorporation with 3' modified nucleotide analogues by using a single cycle experiment as described in example 3. Under those conditions, it is possible to measure the incorporation of a 3° blocked nucleotide at a concentration as low as 50 nM with the 9° N YAV polymerase variant at 45° C.

The invention claimed is:

1. An altered family B archaeal DNA polymerase, wherein the second amino acid of the motif A region is mutated to alanine (A); and the third amino acid of the motif A region is mutated to an amino acid selected from the group consisting of serine (S), alanine (A), glycine (G), and the amino acids having beta-branched side chains, whereby the altered family B archaeal DNA polymerase is capable of incorporating a 3' O-azidomethyl-modified nucleotide.

2. The polymerase of claim 1, wherein the polymerase is selected from the group consisting of a Vent polymerase, a 9° N polymerase, a Pfu polymerase and a JDF-3 polymerase.

3. The polymerase of claim 2, wherein the polymerase is a Pfu polymerase comprising the following mutation: Y410A.

4. The polymerase of claim 2, wherein the polymerase is a JDF-3 polymerase comprising the following mutation: Y409A.

5. The polymerase of claim 1, which exhibits an increased rate of incorporation of the modified nucleotide, compared to a control polymerase selected from wild type polymerase and a variant thereof lacking exonuclease activity.

6. The polymerase of claim 5, wherein the control polymerase is selected from wild type Pfu polymerase and a Pfu polymerase comprising the following mutation: A486Y.

7. The polymerase of claim 5, wherein the control polymerase is selected from wild type JDF-3 polymerase and a JDF-3 polymerase comprising one of the following mutations: A485T, P410L or A485T/P410L.

8. The polymerase of claim 1, wherein the third amino acid of the motif A region is mutated to serine (S), alanine (A) or glycine (G).

9. The polymerase of claim 1, wherein the third amino acid of the motif A region is mutated to isoleucine (I), threonine (T), valine (V) or leucine (L).

10. The polymerase of claim 1, further comprising an amino acid substitution mutation at the first amino acid of the motif A region selected from tyrosine (Y), phenylalanine (F), isoleucine (I), alanine (A), valine (V), glutamine (Q), cysteine (C) or serine (S).

11. The polymerase of claim 10, wherein the motif A region has one of the following mutant amino acid sequences: YST, FAI, AAA, YAS, YAV, YGI, YSG, SGG, CST, IAL, CGG, SAL, SAA, CAA, YAA, QAS, VSS, VAG, VAV, FAV, AGI, YSS, AAT, FSS or VAL.

12. The polymerase of claim 11, wherein the motif A region has the amino acid sequence YAV or YAS.

13. The polymerase of claim 12, wherein the polymerase is a Pfu polymerase having one of the following triple mutations: L409Y/Y410A/P411V or L409Y/Y410A/P411S.

14. The polymerase of claim 12, wherein the polymerase is a JDF-3 polymerase having one of the following triple mutations: L408Y/Y409A/P410V or L408Y/Y409A/P410S.

15. The polymerase of claim 1, further comprising at least one amino acid substitution mutation in the motif B region, whereby the activity of the polymerase is enhanced.

16. The polymerase of claim 15, wherein the substitution mutation in the motif B region is to the second amino acid.

17. The polymerase of claim 16, wherein the substitution mutation is to an amino acid selected from the group consisting of L, F, I, S, V and C.

18. The polymerase of claim 17, wherein the substitution mutation is to L.

19. The polymerase of claim 15, wherein the motif B substitution mutations are to G at the first amino acid position and L at the third.

20. The polymerase of claim 15, wherein the motif B substitution mutations are to N at the first amino acid position and Q at the third.

21. The polymerase of claim 15, wherein the motif B region has one of the following mutant amino acid sequences: SKN, GRD, KHN, ISN and THH.

* * * * *